(12) United States Patent
Blanchard et al.

(10) Patent No.: US 10,859,569 B2
(45) Date of Patent: Dec. 8, 2020

(54) SMFRET WITH MEMBRANE PROTEINS

(71) Applicants: Cornell University, Ithaca, NY (US); THE TRUSTEES OF COLUMBIA UNIVERSITY IN THE CITY OF NEW YORK, New York, NY (US)

(72) Inventors: Scott Blanchard, New York, NY (US); Harel Weinstein, New York, NY (US); Jonathan Javitch, New Rochelle, NY (US)

(73) Assignees: Cornell University, Ithaca, NY (US); THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

(21) Appl. No.: 15/355,819

(22) Filed: Nov. 18, 2016

(65) Prior Publication Data
US 2017/0138933 A1 May 18, 2017

Related U.S. Application Data

(63) Continuation of application No. 13/697,469, filed as application No. PCT/US2011/036459 on May 13, 2011, now abandoned.
(Continued)

(51) Int. Cl.
*G01N 33/542* (2006.01)
*G01N 33/58* (2006.01)
(Continued)

(52) U.S. Cl.
CPC ......... *G01N 33/542* (2013.01); *C07K 14/001* (2013.01); *C07K 14/195* (2013.01);
(Continued)

(58) Field of Classification Search
None
See application file for complete search history.

(56) References Cited

FOREIGN PATENT DOCUMENTS

| WO | 2009/097587 A2 | 8/2009 |
|----|----------------|--------|
| WO | 2010/096720 A2 | 8/2010 |

OTHER PUBLICATIONS

You, M. et al. Forster resonance energy transfer in liposomes: Measurements of transmembrane helix dimerization in the native bilayer environment, Analytical Biochemistry, vol. 340, pp. 154-164 (Year: 2005).*

(Continued)

*Primary Examiner* — Xiaoyun R Xu
(74) *Attorney, Agent, or Firm* — Scully Scott Murphy & Presser

(57) ABSTRACT

This disclosure is directed to methods of conducting dynamic single-molecule fluorescence studies such as smFRET on a membrane protein which permits observation and quantification of conformational dynamics of a membrane protein. Also disclosed herein are mutant membrane proteins in which one or more mutations have been introduced for affixing a fluorophore, as well as reagents and kits containing such mutant membrane proteins for conducting dynamic single-molecule fluorescence studies. The methods and compositions disclosed herein can be used in screening for compounds that enhance or reduce the activity of a membrane protein, useful for treating diseases associated with the malfunction of the membrane protein or alterations in membrane protein conformation.

22 Claims, 19 Drawing Sheets
Specification includes a Sequence Listing.

Related U.S. Application Data

(60) Provisional application No. 61/334,483, filed on May 13, 2010, provisional application No. 61/382,721, filed on Sep. 14, 2010.

(51) Int. Cl.
    C07K 14/195    (2006.01)
    C07K 14/00    (2006.01)
    G01N 21/64    (2006.01)
    C07K 14/245    (2006.01)

(52) U.S. Cl.
    CPC ....... *C07K 14/245* (2013.01); *G01N 21/6428* (2013.01); *G01N 33/582* (2013.01); *G01N 2500/04* (2013.01)

(56) References Cited

OTHER PUBLICATIONS

Gutmann, D.A.P. et al, A high-throughput method for membrane protein solubility screening: The ultracentrifugation dispersity sedimentation assay, Protein Science, vol. 16, pp. 1422-1428 (Year: 2007).*

Wang, L et al., "Addition of the keto Functional Group to the Genetic Code of *Escherichia coli*" Proc. Natl. Acad. Sci. USA (Jan. 7, 2003) pp. 56-61, vol. 100, No. 1.

Williams, A. et al., "Relative Fluorescence Quantum Yields Using a Computer-Controlled Luminescence Spectrometer" Analyst (Sep. 1983) pp. 1067-1071, vol. 108.

Yamashita, A. et al., "Crystal Structure of a Bacterial Homologue of Na+/Cl—Dependent Neurotransmitter Transporters" Nature (Sep. 8, 2005) pp. 215-223, vol. 437.

Zhao, Y. et al., "Single-Molecule Dynamics of Gating in a Neurotransmitter Transporter Homolog" Nature (May 13, 2010) pp. 188-193, vol. 465, No. 7295.

Neubauer, H.A. et al., "Dissection of an Allosteric Mechanism on the Serotonin Transporter: A Cross-Species Study" Molecular Pharmacology (2006) pp. 1242-1250, vol. 69, No. 4.

Zhou, Z. et al., "Antidepressant Specificity of Serotonin Transporter Suggested by Three LeuT-SSRI Structures" Nature Struct. Mol. Biol. (Jun. 2009) pp. 652-657, vol. 16, No. 6.

Zhou, Z. et al., "LeuT-Desipramine Structure Reveals How Antidepressants Block Neurotransmitter Reuptake" Science (Sep. 7, 2007) pp. 1390-1393, vol. 317.

U.S. Appl. No. 61/437,203, filed Jan. 28, 2011, related to International Application No. PCT/US12/22875, Titled "Software Platform for Single-Molecule Fret Imagining and Kinetic Analysis", First Named Inventor Daniel Terry.

Bannerjee, S. et al., "Rapid Incorporation of Functional Rhodopsin into Nanoscale Apolipoprotein Bound Bilayer (NABB) Particles" Journal of Molecular Biology (Apr. 4, 2008) pp. 1067-1081, vol. 377, No. 4.

Beckett, D. et al., "A Minimal Peptide Substrate in Biotin Holoenzymes Synthetase-Catalyzed Biotinylation" Protein Science (1999) pp. 921-929,vol. 8.

Bennett, E.R. et al., "Mutation of Arginine 44 of GAT-1, a (Na++ Cl-)-Coupled u-Amniobutyric Acid Transported from Rat Brain, Impairs Net Flux but not Exchange" The Journal of Biological Chemistry (2000) pp. 34106-34113, vol. 275, No. 44.

Beuming, T. et al., "A Comprehensive Structure-Based Alignment of Prokaryotic and Eukaryotic Neurotransmitter/Na+ Symporters (NSS) Aids in the Use of the LeuT Structure to Probe NSS Structure and Function" Molecular Pharmacology (2006) pp. 1630-1642, vol. 70, No. 5.

Blanchard, S.C. et al., "tRNA Dynamics on the Ribosome During Translation" Proc. Natl Acad. Sci. USA (Aug. 31, 2004), pp. 12893-12898, vol. 101, No. 35.

Borch, J. et al., "The Nanodisc: a Novel Tool for Membrane Protein Studies" Biol Chem. (Aug. 2009) pp. 805-814, vol. 390, No. 8.

Brizzard, B., "Epitope Tagging" BioTechniques (Apr. 2008) pp. 693-695, vol. 44.

Caplan, D.A., et al., "Molecular Mechanism of Ion-Ion and Ion-Substrate Coupling in the Na+-Dependent Leucine Transporter LeuT" Biophysical Journal (Nov. 2008) pp. 4613-4621, vol. 95.

Cheng, F. et al., "XPS, TOF-SIMS, NEXAFS, and SPR Characterization of Nitrilotriacetic Acid-Terminated Self-Assembled Monolayers for Controllable Immobilization of Proteins" Anal Chem. (Apr. 1, 2008) pp. 2564-2576, vol. 80, No. 7.

Chin, J.W. et al., "An Expanded Eukaryotic Genetic Code" Science (Aug. 15, 2003) pp. 964-967, vol. 301.

Claxton, D.P. et al., "Ion/substrate-dependent Conformational Dynamics of a Bacterial Homolog of Neurotransmitter: Sodium Symporters" Nat Struct Mol Biol (Jul. 2010) pp. 822-829, vol. 17, No. 7.

Dave, R. et al., "Mitigating Unwanted Photophysical Processes for Improved Single-Molecule Fluorescence Imaging" Biophysical Journal (Mar. 2009) pp. 2371-2381, vol. 96.

Feldman, M.B. et al., "Aminoglycoside Activity Observed on Single Pre-Translocation Ribosome Complexes" Nat Chem Biol. (Jan. 2010) pp. 54-62, vol. 6, No. 1.

Harms, G.S. et al., "Probing Conformational Changes of Gramicidin Ion Channels by Single-Molecule Patch-Clamp Fluorescence Microscopy" Biophysical Journal (Sep. 2003) pp. 1826-1838, vol. 85.

Jardetzky, O., "Simple Allosteric Model for Membrane Pumps" Nature (Aug. 27, 1966) pp. 969-970, vol. 211, No. 5052.

Kaestner, C.N. et al., "The Citrate Carrier CitS Probed by Single-Molecule Fluorescence Spectroscopy" Biophysical Journal (Mar. 2003) pp. 1651-1659, vol. 84.

Karstens, T. et al., "Rhodamine B and Rhodamine 101 as Reference Substance for Fluorescence Quantum Yield Measurements" J. Phys. Chem. (1980) pp. 1871-1872, vol. 84.

Keller, P.C. et al., "Cysteine-Scanning Mutagenesis of the Fifth External Loop of Serotonin Transporter" Biochemistry (2004) pp. 8510-8516, vol. 43, No. 26.

Kniazeff, J. et al., "An Intracellular Interaction Network Regulates Conformational Transitions in the Dopamine Transporter" J. Biol. Chem. (Jun. 20, 2008) pp. 17691-17701, vol. 283, No. 25.

Knowles, T.J. et al., "Membrane Proteins Solubilized Intact in Lipid Containing Nanoparticles Bounded by Styrene Maleic Acid Copolymer" J Am Chem Soc. (Jun. 2009) pp. 7484-7485, vol. 131, No. 22.

Lockless, S.W. et al., "Evolutionarily Conserved Pathways of Energetic Connectivity in Protein Families" Science (1999) pp. 295-299, vol. 286.

Majumdar, D.S. et al., "Single-Molecule FRET Reveals Sugar-Induced Conformational Dynamics in LacY" Proc. Natl Acad. Sci. USA (Jul. 31, 2007) pp. 12640-12645, vol. 104, No. 31.

Margittai, M. et al. "Single-Molecule Fluorescence Resonance Energy Transfer Reveals a Dynamic Equilibrium Between Closed and Open Conformations of Syntaxin 1" Proc. Natl. Acad. Sci. USA (Dec. 23, 2003) pp. 15516-15521, vol. 100, No. 26.

Maurel, D., et al, "Cell-Surface Protein-Protein Interaction Analysis with Time-Resolved FRET and Snap-Tag Technologies: Application to GPCR Oligomerization" Nat. Methods (Jun. 2008) pp. 561-567, vol. 5, No. 6.

Muir, T.W., "Semisynthesis of Proteins by Expressed Protein Ligation" Annu Rev Biochem (2003) pp. 249-289, vol. 72.

Mujumdar, R.B. et al., "Cyanine Dye Labeling Reagents: Sulfoindocyanine Succinimidyl Esters" Bioconjug. Chem. (Mar./Apr. 1993) pp. 105-111, vol. 4, No. 2.

Munro, J.B. et al., "Identification of Two Distinct Hybrid State Intermediates on the Ribosome" Molecular Cell (Feb. 23, 2007) pp. 505-517, vol. 25.

Munro, J.B., et al., "A Fast Dynamic Mode of the EF-G-Bound Ribosome" The EMBO Journal (2010) pp. 770-781, vol. 29, No. 4.

Muralidharan, V. et al., "Protein ligation: an enabling technology for the biophysical analysis of proteins" Nature Methods (Jun. 2006) pp. 429-438, vol. 3, No. 6.

Nie, Y. et al., "The Cys154□Gly Mutation in LacY Causes Constitutive Opening of the Hydrophilic Periplasmic Pathway" J. Mol. Biol. (2008) pp. 695-703, vol. 379.

(56) References Cited

OTHER PUBLICATIONS

Noskov, S.Y. et al., "Control of Ion Selectivity in LeuT: Two Na+ Binding Sites with Two Different Mechanisms" J. Mol. Biol. (2008) pp. 804-818, vol. 377.

Nwe, K., et al., "Growing Applications of "Click Chemistry" for Bioconjugation in Contemporary Biomedical Research" Cancer Biotherapy Radiopharmaceuticals (2009) pp. 289-302, vol. 24, No. 3.

Qin, F. et al., "Estimating Single-Channel Kinetic Parameters from Idealized Patch-Clamp Data Containing Missed Events" Biophysical Journal (Jan. 1996) pp. 264-280, vol. 70.

Qin, F. et al., "Restoration of Single-Channel Currents Using the Segmental k-Means Method Based on Hidden Markov Modeling" Biophysical Journal (Mar. 2004) pp. 1488-1501, vol. 86.

Quick, M. et al., "Monitoring the Function of Membrane Transport Proteins in Detergent-Solubilized Form" Proc. Natl Acad. Sci. USA (Feb. 27, 2007) pp. 3603-3608, vol. 104, No. 9.

Quick, M. et al., "Binding of an Octylglucoside Detergent Molecule in the Second Substrate (S2) Site of LeuT Establishes an Inhibitor-Bound Conformation" Proc. Natl Acad. Sci. USA (Apr. 7, 2009) pp. 5563-5568, vol. 106, No. 14.

Quick, M., et al., "State-dependent Conformations of the Translocation Pathway in the Tyrosine Transporter Tyt1, a Novel Neurotransmitter: Sodium Symporter from Fusobacterium nucleatum" J. Biol. Chem. (Sep. 8, 2006) pp. 26444-26454, vol. 281, No. 36.

Roy, R. et al., "A Practical Guide to Single-Molecule FRET" Nature Methods (Jun. 2008) pp. 507-516, vol. 5, No. 6.

Sakon, J.J. et al., "Detecting the Conformation of Individual Proteins in Live Cells" Nature Methods (Mar. 2010) pp. 203-205, vol. 7, No. 3.

Schaffner, W. et al., "A rapid, Sensitive, and Specific Method for the Determination of Protein in Dilute Solution" Anal. Biochem. (1973) pp. 502-514, vol. 56.

Sen, N. et al., "A Pincer-Like Configuration of TM2 in the Human Dopamine Transporter is Responsible for Indirect Effects on Cocaine Binding" Neuropharmacology (2005) pp. 780-790, vol. 49, No. 6.

Shaffer, P.L. et al., "Structure and Mechanism of a Na+-Independent Amino Acid Transporter" Science (Aug. 21, 2009) pp. 1010-1014, vol. 325.

Shan, J. et al., "The Substrate-Driven Transition to an Inward-Facing Conformation in the Functional Mechanism of the Dopamine Transporter" PLoS One (Jan. 2011) pp. e16350-1-e16350-15, vol. 6, No. 1.

Shi, L. et al., "The Mechanism of a Neurotransmitter: Sodium Symporter-Inward Release of Na+ and Substrate Is Triggered by Substrate in a Second Binding Site" Molecular Cell (Jun. 20, 2008) pp. 667-677, vol. 30.

Singh, S.K. et al., "LeuT A Prokaryotic Stepping Stone on the Way to a Eukaryotic Neurotransmitter Transporter Structure" Channels (Sep./Oct. 2008) pp. 380-389, vol. 2, No. 5.

Singh, S K. et al., "Antidepressant Binding Site in a Bacterial Homologue of Neurotransmitter Transporters" Nature (Aug. 23, 2007) pp. 952-956, vol. 448.

\* cited by examiner

| Labeling Positions | Leu binding activity (% of wild-type) | Ala uptake activity (% of wild-type) |
|---|---|---|
| H7C/R86C | 94±2% | 112±2% |
| H7C/T515C | 107±3% | 110±12% |
| R185C/K271C | 93±2% | 94±4% |
| R185C/T515C | 112±2% | 108±4% |
| R86C/K271C | 96±2% | 96±20% |
| R86C/R185C | 83±3% | 89±4% |
| K239C/H480C | 91±7% | 105±2% |

Figure 8

| Labeling Position | Mutation/ Inhibitor | Ligands | Observed FRET | Corrected FRET | Dye-to-Dye Distance (Å) |
|---|---|---|---|---|---|
| 7+86 | | | 0.51 | 0.59 | 55 |
| | | | 0.75 | 0.88 | 42 |
| | | Na | 0.77 | 0.91 | 40 |
| | | Na+Leu | 0.77 | 0.91 | 40 |
| | R5A | | 0.43 | 0.49 | 59 |
| | | Na | 0.54 | 0.62 | 54 |
| | Y268A | | 0.44 | 0.50 | 58 |
| | | Na | 0.56 | 0.65 | 53 |
| | R30A | | 0.70 | 0.82 | 45 |
| | | Na | 0.71 | 0.83 | 45 |
| | | Na+Leu | 0.71 | 0.83 | 45 |
| | CMI | | 0.69 | 0.81 | 46 |
| | | Na | 0.69 | 0.81 | 46 |
| | OG | | 0.68 | 0.80 | 47 |
| | | Na | 0.68 | 0.80 | 47 |
| 239+480 | | | 0.49 | 0.56 | 56 |
| | | Na | 0.51 | 0.59 | 55 |
| | | Na+Leu | 0.52 | 0.60 | 55 |
| | R5A | | 0.66 | 0.77 | 48 |
| | Y268A | | 0.67 | 0.78 | 47 |
| | R30A | | 0.49 | 0.56 | 56 |
| | | Na | 0.52 | 0.60 | 55 |
| | | Na+Leu | 0.52 | 0.60 | 55 |
| | CMI | | 0.53 | 0.61 | 54 |
| 7+515 | | | 0.43 | 0.49 | 59 |
| | | | 0.73 | 0.86 | 43 |
| | | Na | 0.73 | 0.86 | 43 |
| | | Na+Leu | 0.74 | 0.87 | 43 |
| | Y268A | | 0.40 | 0.46 | 60 |
| | | Na | 0.46 | 0.53 | 57 |
| | R30A | | 0.67 | 0.78 | 47 |
| | | Na | 0.72 | 0.85 | 44 |
| 86+185 | | | 0.58 | 0.67 | 52 |
| | | Na | 0.58 | 0.67 | 52 |
| | | Na+Leu | 0.57 | 0.66 | 52 |
| 185+515 | | | 0.61 | 0.71 | 50 |
| | | Na | 0.61 | 0.71 | 50 |
| | | Na+Leu | 0.61 | 0.71 | 50 |
| 86+271 | | | 0.80 | 0.95 | 36 |
| | | Na | 0.80 | 0.95 | 36 |
| | | Na+Leu | 0.80 | 0.95 | 36 |
| 185+271 | | | 0.70 | 0.82 | 45 |
| | | Na | 0.68 | 0.80 | 47 |
| | | Na+Leu | 0.71 | 0.83 | 45 |

Figure 9

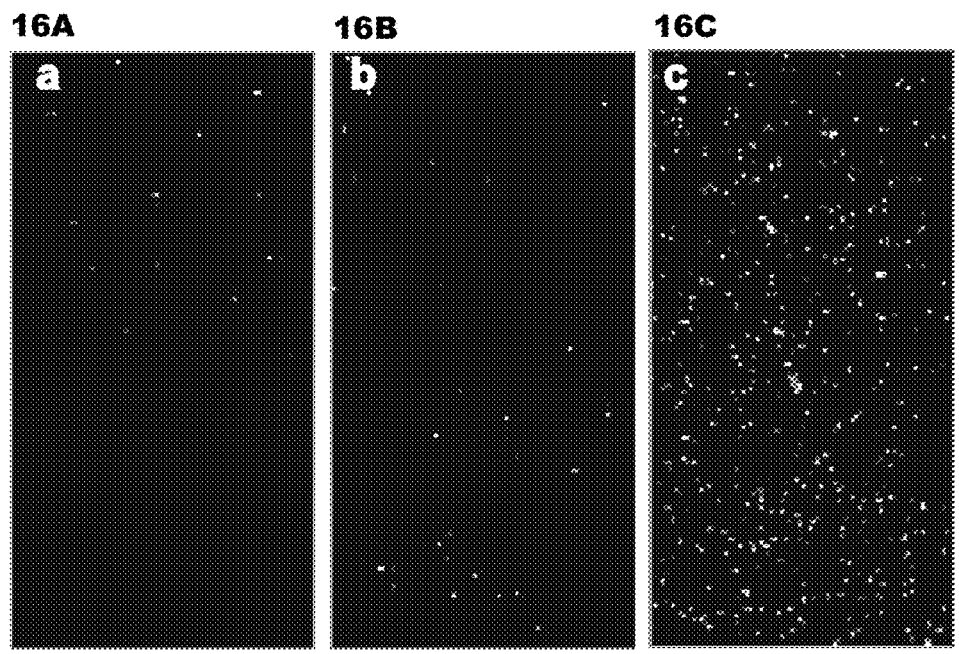
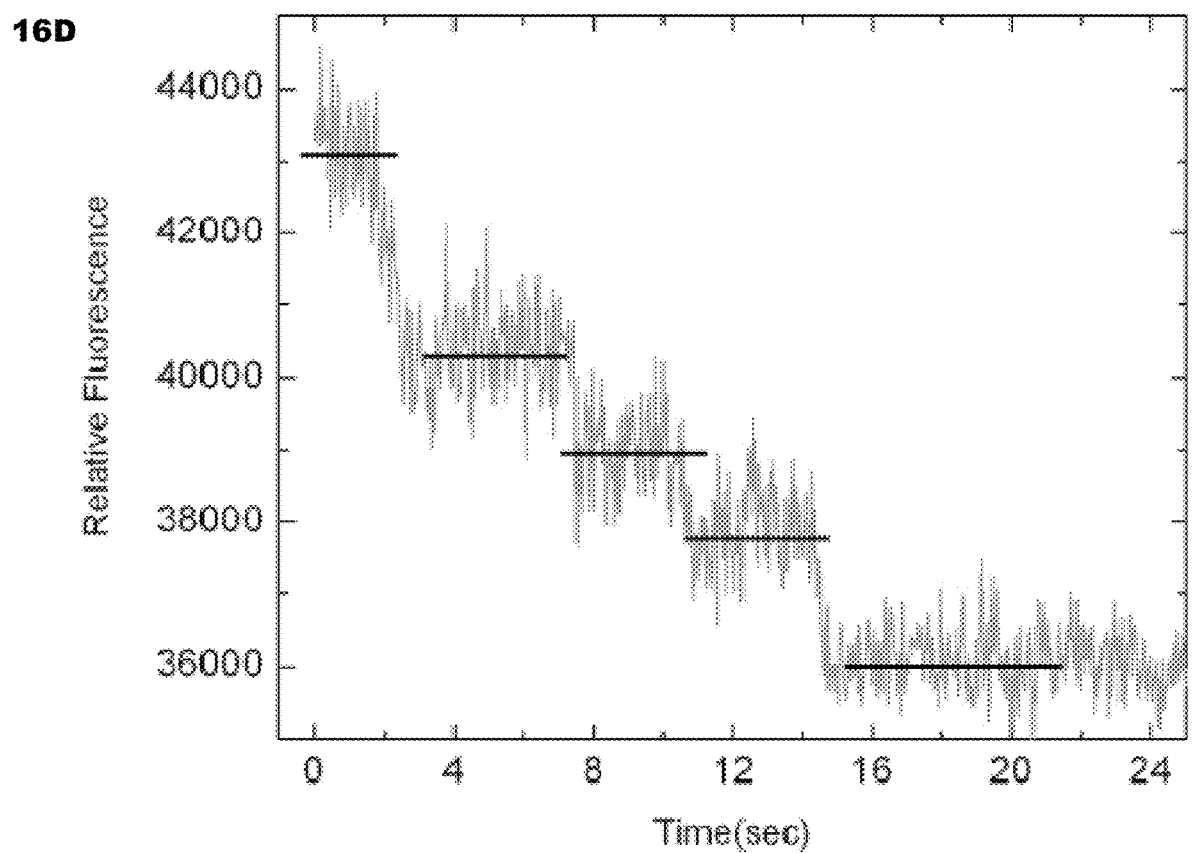
Figures 16A-16D

Figure 18

SEQUENCE LISTING

```
<160> NUMBER OF SEQ ID NOS: 7

<210> SEQ ID NO 1
<211> LENGTH: 15
<212> TYPE: PRT
<213> ORGANISM: Artificial Sequence
<220> FEATURE:
<223> OTHER INFORMATION: Biotin Acceptor Peptide (AP) sequence

<400> SEQUENCE: 1

Gly Leu Asn Asp Ile Phe Glu Ala Gln Lys Ile Glu Trp His Glu
```

<210> SEQ ID NO 2
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 2 tcgagggggct taatgatatc tttgaagctc agaaaattga atggcatgag tgag            54

<210> SEQ ID NO 3
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 3
gatcctcact catgccattc aattttctga gcttcaaaga tatcattaag cccc            54

<210> SEQ ID NO 4
<211> LENGTH: 515
<212> TYPE: PRT
<213> ORGANISM: Aquifex aeolicus

<400> SEQUENCE: 4

Met Glu Val Lys Arg Glu His Trp Ala Thr Arg Leu Gly Leu Ile Leu
1               5                   10                  15

Ala Met Ala Gly Asn Ala Val Gly Leu Gly Asn Phe Leu Arg Phe Pro
            20                  25                  30

Val Gln Ala Ala Glu Asn Gly Gly Gly Ala Phe Met Ile Pro Tyr Ile
        35                  40                  45

Ile Ala Phe Leu Leu Val Gly Ile Pro Leu Met Trp Ile Glu Trp Ala
    50                  55                  60

Met Gly Arg Tyr Gly Gly Ala Gln Gly His Gly Thr Thr Pro Ala Ile
65                  70                  75                  80

Phe Tyr Leu Leu Trp Arg Asn Arg Phe Ala Lys Ile Leu Gly Val Phe
                85                  90                  95

Gly Leu Trp Ile Pro Leu Val Val Ala Ile Tyr Tyr Val Tyr Ile Glu
            100                 105                 110

Ser Trp Thr Leu Gly Phe Ala Ile Lys Phe Leu Val Gly Leu Val Pro
        115                 120                 125

Glu Pro Pro Asn Ala Thr Asp Pro Asp Ser Ile Leu Arg Pro Phe
    130                 135                 140

Lys Glu Phe Leu Tyr Ser Tyr Ile Gly Val Pro Lys Gly Asp Glu Pro
145                 150                 155                 160

Ile Leu Lys Pro Ser Leu Phe Ala Tyr Ile Val Phe Leu Ile Thr Met
                165                 170                 175

Phe Ile Asn Val Ser Ile Leu Ile Arg Gly Ile Ser Lys Gly Ile Glu
            180                 185                 190

Arg Phe Ala Lys Ile Ala Met Pro Thr Leu Phe Ile Leu Ala Val Phe
        195                 200                 205

Leu Val Ile Arg Val Phe Leu Leu Glu Thr Pro Asn Gly Thr Ala Ala
    210                 215                 220

Asp Gly Leu Asn Phe Leu Trp Thr Pro Asp Phe Glu Lys Leu Lys Asp
225                 230                 235                 240

-continued

```
Pro Gly Val Trp Ile Ala Ala Val Gly Gln Ile Phe Phe Thr Leu Ser
                245                 250                 255

Leu Gly Phe Gly Ala Ile Ile Thr Tyr Ala Ser Tyr Val Arg Lys Asp
            260                 265                 270

Gln Asp Ile Val Leu Ser Gly Leu Thr Ala Ala Thr Leu Asn Glu Lys
        275                 280                 285

Ala Glu Val Ile Leu Gly Gly Ser Ile Ser Pro Ala Ala Val Ala
    290                 295                 300

Phe Phe Gly Val Ala Asn Ala Val Ala Ile Ala Lys Ala Gly Ala Phe
305                 310                 315                 320

Asn Leu Gly Phe Ile Thr Leu Pro Ala Ile Phe Ser Gln Thr Ala Gly
            325                 330                 335

Gly Thr Phe Leu Gly Phe Leu Trp Phe Leu Leu Phe Phe Ala Gly
        340                 345                 350

Leu Thr Ser Ser Ile Ala Ile Met Gln Pro Met Ile Ala Phe Leu Glu
    355                 360                 365

Asp Glu Leu Lys Leu Ser Arg Lys His Ala Val Leu Trp Thr Ala Ala
370                 375                 380

Ile Val Phe Phe Ser Ala His Leu Val Met Phe Leu Asn Lys Ser Leu
385                 390                 395                 400

Asp Glu Met Asp Phe Trp Ala Gly Thr Ile Gly Val Val Phe Phe Gly
            405                 410                 415

Leu Thr Glu Leu Ile Ile Phe Phe Trp Ile Phe Gly Ala Asp Lys Ala
        420                 425                 430

Trp Glu Glu Ile Asn Arg Gly Gly Ile Ile Lys Val Pro Arg Ile Tyr
    435                 440                 445

Tyr Tyr Val Met Arg Tyr Ile Thr Pro Ala Phe Leu Ala Val Leu Leu
450                 455                 460

Val Val Trp Ala Arg Glu Tyr Ile Pro Lys Ile Met Glu Glu Thr His
465                 470                 475                 480

Trp Thr Val Trp Ile Thr Arg Phe Tyr Ile Ile Gly Leu Phe Leu Phe
            485                 490                 495

Leu Thr Phe Leu Val Phe Leu Ala Glu Arg Arg Arg Asn His Glu Ser
        500                 505                 510

Ala Gly Thr
        515

<210> SEQ ID NO 5
<211> LENGTH: 620
<212> TYPE: PRT
<213> ORGANISM: Homo sapiens

<400> SEQUENCE: 5

Met Ser Lys Ser Lys Cys Ser Val Gly Leu Met Ser Ser Val Val Ala
1               5                   10                  15

Pro Ala Lys Glu Pro Asn Ala Val Gly Pro Lys Glu Val Glu Leu Ile
            20                  25                  30

Leu Val Lys Glu Gln Asn Gly Val Gln Leu Thr Ser Ser Thr Leu Thr
        35                  40                  45

Asn Pro Arg Gln Ser Pro Val Glu Ala Gln Asp Arg Glu Thr Trp Gly
    50                  55                  60

Lys Lys Ile Asp Phe Leu Leu Ser Val Ile Gly Phe Ala Val Asp Leu
65                  70                  75                  80

Ala Asn Val Trp Arg Phe Pro Tyr Leu Cys Tyr Lys Asn Gly Gly Gly
            85                  90                  95
```

```
Ala Phe Leu Val Pro Tyr Leu Phe Met Val Ile Ala Gly Met Pro
            100                 105                 110
Leu Phe Tyr Met Glu Leu Ala Leu Gly Gln Phe Asn Arg Glu Gly Ala
            115                 120                 125
Ala Gly Val Trp Lys Ile Cys Pro Ile Leu Lys Gly Val Gly Phe Thr
            130                 135                 140
Val Ile Leu Ile Ser Leu Tyr Val Gly Phe Phe Tyr Asn Val Ile Ile
145                 150                 155                 160
Ala Trp Ala Leu His Tyr Leu Phe Ser Ser Phe Thr Thr Glu Leu Pro
                165                 170                 175
Trp Ile His Cys Asn Asn Ser Trp Asn Ser Pro Asn Cys Ser Asp Ala
                180                 185                 190
His Pro Gly Asp Ser Ser Gly Asp Ser Ser Gly Leu Asn Asp Thr Phe
                195                 200                 205
Gly Thr Thr Pro Ala Ala Glu Tyr Phe Glu Arg Gly Val Leu His Leu
            210                 215                 220
His Gln Ser His Gly Ile Asp Asp Leu Gly Pro Pro Arg Trp Gln Leu
225                 230                 235                 240
Thr Ala Cys Leu Val Leu Val Ile Val Leu Leu Tyr Phe Ser Leu Trp
                245                 250                 255
Lys Gly Val Lys Thr Ser Gly Lys Val Val Trp Ile Thr Ala Thr Met
                260                 265                 270
Pro Tyr Val Val Leu Thr Ala Leu Leu Leu Arg Gly Val Thr Leu Pro
            275                 280                 285
Gly Ala Ile Asp Gly Ile Arg Ala Tyr Leu Ser Val Asp Phe Tyr Arg
            290                 295                 300
Leu Cys Glu Ala Ser Val Trp Ile Asp Ala Ala Thr Gln Val Cys Phe
305                 310                 315                 320
Ser Leu Gly Val Gly Phe Gly Val Leu Ile Ala Phe Ser Ser Tyr Asn
                325                 330                 335
Lys Phe Thr Asn Asn Cys Tyr Arg Asp Ala Ile Val Thr Thr Ser Ile
                340                 345                 350
Asn Ser Leu Thr Ser Phe Ser Ser Gly Phe Val Val Phe Ser Phe Leu
            355                 360                 365
Gly Tyr Met Ala Gln Lys His Ser Val Pro Ile Gly Asp Val Ala Lys
            370                 375                 380
Asp Gly Pro Gly Leu Ile Phe Ile Ile Tyr Pro Glu Ala Ile Ala Thr
385                 390                 395                 400
Leu Pro Leu Ser Ser Ala Trp Ala Val Val Phe Phe Ile Met Leu Leu
                405                 410                 415
Thr Leu Gly Ile Asp Ser Ala Met Gly Gly Met Glu Ser Val Ile Thr
                420                 425                 430
Gly Leu Ile Asp Glu Phe Gln Leu Leu His Arg His Arg Glu Leu Phe
            435                 440                 445
Thr Leu Phe Ile Val Leu Ala Thr Phe Leu Leu Ser Leu Phe Cys Val
            450                 455                 460
Thr Asn Gly Gly Ile Tyr Val Phe Thr Leu Leu Asp His Phe Ala Ala
465                 470                 475                 480
Gly Thr Ser Ile Leu Phe Gly Val Leu Ile Glu Ala Ile Gly Val Ala
                485                 490                 495
Trp Phe Tyr Gly Val Gly Gln Phe Ser Asp Asp Ile Gln Gln Met Thr
            500                 505                 510
```

```
Gly Gln Arg Pro Ser Leu Tyr Trp Arg Leu Cys Trp Lys Leu Val Ser
            515                 520                 525

Pro Cys Phe Leu Leu Phe Val Val Val Ser Ile Val Thr Phe Arg
    530                 535                 540

Pro Pro His Tyr Gly Ala Tyr Ile Phe Pro Asp Trp Ala Asn Ala Leu
545                 550                 555                 560

Gly Trp Val Ile Ala Thr Ser Ser Met Ala Met Val Pro Ile Tyr Ala
                565                 570                 575

Ala Tyr Lys Phe Cys Ser Leu Pro Gly Ser Phe Arg Glu Lys Leu Ala
            580                 585                 590

Tyr Ala Ile Ala Pro Glu Lys Asp Arg Glu Leu Val Asp Arg Gly Glu
            595                 600                 605

Val Arg Gln Phe Thr Leu Arg His Trp Leu Lys Val
            610                 615                 620

<210> SEQ ID NO 6
<211> LENGTH: 617
<212> TYPE: PRT
<213> ORGANISM: Homo sapiens

<400> SEQUENCE: 6

Met Leu Leu Ala Arg Met Asn Pro Gln Val Gln Pro Glu Asn Asn Gly
1               5                   10                  15

Ala Asp Thr Gly Pro Glu Gln Pro Leu Arg Ala Arg Lys Thr Ala Glu
                20                  25                  30

Leu Leu Val Val Lys Glu Arg Asn Gly Val Gln Cys Leu Leu Ala Pro
            35                  40                  45

Arg Asp Gly Asp Ala Gln Pro Arg Glu Thr Trp Gly Lys Lys Ile Asp
50                  55                  60

Phe Leu Leu Ser Val Val Gly Phe Ala Val Asp Leu Ala Asn Val Trp
65                  70                  75                  80

Arg Phe Pro Tyr Leu Cys Tyr Lys Asn Gly Gly Gly Ala Phe Leu Ile
                85                  90                  95

Pro Tyr Thr Leu Phe Leu Ile Ile Ala Gly Met Pro Leu Phe Tyr Met
                100                 105                 110

Glu Leu Ala Leu Gly Gln Tyr Asn Arg Glu Gly Ala Ala Thr Val Trp
            115                 120                 125

Lys Ile Cys Pro Phe Phe Lys Gly Val Gly Tyr Ala Val Ile Leu Ile
            130                 135                 140

Ala Leu Tyr Val Gly Phe Tyr Tyr Asn Val Ile Ile Ala Trp Ser Leu
145                 150                 155                 160

Tyr Tyr Leu Phe Ser Ser Phe Thr Leu Asn Leu Pro Trp Thr Asp Cys
                165                 170                 175

Gly His Thr Trp Asn Ser Pro Asn Cys Thr Asp Pro Lys Leu Leu Asn
                180                 185                 190

Gly Ser Val Leu Gly Asn His Thr Lys Tyr Ser Lys Tyr Lys Phe Thr
            195                 200                 205

Pro Ala Ala Glu Phe Tyr Glu Arg Gly Val Leu His Leu His Glu Ser
    210                 215                 220

Ser Gly Ile His Asp Ile Gly Leu Pro Gln Trp Gln Leu Leu Leu Cys
225                 230                 235                 240

Leu Met Val Val Val Ile Val Leu Tyr Phe Ser Leu Trp Lys Gly Val
                245                 250                 255

Lys Thr Ser Gly Lys Val Val Trp Ile Thr Ala Thr Leu Pro Tyr Phe
                260                 265                 270
```

Val Leu Phe Val Leu Val His Gly Val Thr Leu Pro Gly Ala Ser
    275                 280                 285

Asn Gly Ile Asn Ala Tyr Leu His Ile Asp Phe Tyr Arg Leu Lys Glu
290                 295                 300

Ala Thr Val Trp Ile Asp Ala Thr Gln Ile Phe Phe Ser Leu Gly
305                 310                 315                 320

Ala Gly Phe Gly Val Leu Ile Ala Phe Ala Ser Tyr Asn Lys Phe Asp
                325                 330                 335

Asn Asn Cys Tyr Arg Asp Ala Leu Leu Thr Ser Ser Ile Asn Cys Ile
                340                 345                 350

Thr Ser Phe Val Ser Gly Phe Ala Ile Phe Ser Ile Leu Gly Tyr Met
    355                 360                 365

Ala His Glu His Lys Val Asn Ile Glu Asp Val Ala Thr Glu Gly Ala
    370                 375                 380

Gly Leu Val Phe Ile Leu Tyr Pro Glu Ala Ile Ser Thr Leu Ser Gly
385                 390                 395                 400

Ser Thr Phe Trp Ala Val Val Phe Phe Val Met Leu Leu Ala Leu Gly
                405                 410                 415

Leu Asp Ser Ser Met Gly Gly Met Glu Ala Val Ile Thr Gly Leu Ala
                420                 425                 430

Asp Asp Phe Gln Val Leu Lys Arg His Arg Lys Leu Phe Thr Phe Gly
                435                 440                 445

Val Thr Phe Ser Thr Phe Leu Leu Ala Leu Phe Cys Ile Thr Lys Gly
    450                 455                 460

Gly Ile Tyr Val Leu Thr Leu Leu Asp Thr Phe Ala Ala Gly Thr Ser
465                 470                 475                 480

Ile Leu Phe Ala Val Leu Met Glu Ala Ile Gly Val Ser Trp Phe Tyr
                485                 490                 495

Gly Val Asp Arg Phe Ser Asn Asp Ile Gln Gln Met Met Gly Phe Arg
                500                 505                 510

Pro Gly Leu Tyr Trp Arg Leu Cys Trp Lys Phe Val Ser Pro Ala Phe
    515                 520                 525

Leu Leu Phe Val Val Val Ser Ile Ile Asn Phe Lys Pro Leu Thr
    530                 535                 540

Tyr Asp Asp Tyr Ile Phe Pro Pro Trp Ala Asn Trp Val Gly Trp Gly
545                 550                 555                 560

Ile Ala Leu Ser Ser Met Val Leu Val Pro Ile Tyr Val Ile Tyr Lys
                565                 570                 575

Phe Leu Ser Thr Gln Gly Ser Leu Trp Glu Arg Leu Ala Tyr Gly Ile
                580                 585                 590

Thr Pro Glu Asn Glu His His Leu Val Ala Gln Arg Asp Ile Arg Gln
    595                 600                 605

Phe Gln Leu Gln His Trp Leu Ala Ile
610                 615

<210> SEQ ID NO 7
<211> LENGTH: 630
<212> TYPE: PRT
<213> ORGANISM: Homo sapiens

<400> SEQUENCE: 7

Met Glu Thr Thr Pro Leu Asn Ser Gln Lys Gln Leu Ser Ala Cys Glu
1               5                   10                  15

Asp Gly Glu Asp Cys Gln Glu Asn Gly Val Leu Gln Lys Val Val Pro

-continued

```
                20                  25                  30
Thr Pro Gly Asp Lys Val Glu Ser Gly Gln Ile Ser Asn Gly Tyr Ser
            35                  40                  45
Ala Val Pro Ser Pro Gly Ala Gly Asp Asp Thr Arg His Ser Ile Pro
 50                  55                  60
Ala Thr Thr Thr Thr Leu Val Ala Glu Leu His Gln Gly Glu Arg Glu
 65                  70                  75                  80
Thr Trp Gly Lys Lys Val Asp Phe Leu Leu Ser Val Ile Gly Tyr Ala
                85                  90                  95
Val Asp Leu Gly Asn Val Trp Arg Phe Pro Tyr Ile Cys Tyr Gln Asn
            100                 105                 110
Gly Gly Gly Ala Phe Leu Leu Pro Tyr Thr Ile Met Ala Ile Phe Gly
            115                 120                 125
Gly Ile Pro Leu Phe Tyr Met Glu Leu Ala Leu Gly Gln Tyr His Arg
            130                 135                 140
Asn Gly Cys Ile Ser Ile Trp Arg Lys Ile Cys Pro Ile Phe Lys Gly
145                 150                 155                 160
Ile Gly Tyr Ala Ile Cys Ile Ile Ala Phe Tyr Ile Ala Ser Tyr Tyr
                165                 170                 175
Asn Thr Ile Met Ala Trp Ala Leu Tyr Tyr Leu Ile Ser Ser Phe Thr
            180                 185                 190
Asp Gln Leu Pro Trp Thr Ser Cys Lys Asn Ser Trp Asn Thr Gly Asn
            195                 200                 205
Cys Thr Asn Tyr Phe Ser Glu Asp Asn Ile Thr Trp Thr Leu His Ser
    210                 215                 220
Thr Ser Pro Ala Glu Glu Phe Tyr Thr Arg His Val Leu Gln Ile His
225                 230                 235                 240
Arg Ser Lys Gly Leu Gln Asp Leu Gly Gly Ile Ser Trp Gln Leu Ala
                245                 250                 255
Leu Cys Ile Met Leu Ile Phe Thr Val Ile Tyr Phe Ser Ile Trp Lys
            260                 265                 270
Gly Val Lys Thr Ser Gly Lys Val Val Trp Val Thr Ala Thr Phe Pro
            275                 280                 285
Tyr Ile Ile Leu Ser Val Leu Leu Val Arg Gly Ala Thr Leu Pro Gly
            290                 295                 300
Ala Trp Arg Gly Val Leu Phe Tyr Leu Lys Pro Asn Trp Gln Lys Leu
305                 310                 315                 320
Leu Glu Thr Gly Val Trp Ile Asp Ala Ala Gln Ile Phe Phe Ser
                325                 330                 335
Leu Gly Pro Gly Phe Gly Val Leu Leu Ala Phe Ala Ser Tyr Asn Lys
            340                 345                 350
Phe Asn Asn Asn Cys Tyr Gln Asp Ala Leu Val Thr Ser Val Val Asn
            355                 360                 365
Cys Met Thr Ser Phe Val Ser Gly Phe Val Ile Phe Thr Val Leu Gly
    370                 375                 380
Tyr Met Ala Glu Met Arg Asn Glu Asp Val Ser Glu Val Ala Lys Asp
385                 390                 395                 400
Ala Gly Pro Ser Leu Leu Phe Ile Thr Tyr Ala Glu Ala Ile Ala Asn
                405                 410                 415
Met Pro Ala Ser Thr Phe Phe Ala Ile Ile Phe Phe Leu Met Leu Ile
            420                 425                 430
Thr Leu Gly Leu Asp Ser Thr Phe Ala Gly Leu Glu Gly Val Ile Thr
            435                 440                 445
```

-continued

```
Ala Val Leu Asp Glu Phe Pro His Val Trp Ala Lys Arg Arg Glu Arg
    450                 455                 460
Phe Val Leu Ala Val Val Ile Thr Cys Phe Phe Gly Ser Leu Val Thr
465                 470                 475                 480
Leu Thr Phe Gly Gly Ala Tyr Val Val Lys Leu Leu Glu Glu Tyr Ala
                485                 490                 495
Thr Gly Pro Ala Val Leu Thr Val Ala Leu Ile Glu Ala Val Ala Val
                500                 505                 510
Ser Trp Phe Tyr Gly Ile Thr Gln Phe Cys Arg Asp Val Lys Glu Met
            515                 520                 525
Leu Gly Phe Ser Pro Gly Trp Phe Trp Arg Ile Cys Trp Val Ala Ile
        530                 535                 540
Ser Pro Leu Phe Leu Leu Phe Ile Ile Cys Ser Phe Leu Met Ser Pro
545                 550                 555                 560
Pro Gln Leu Arg Leu Phe Gln Tyr Asn Tyr Pro Tyr Trp Ser Ile Ile
                565                 570                 575
Leu Gly Tyr Cys Ile Gly Thr Ser Ser Phe Ile Cys Ile Pro Thr Tyr
            580                 585                 590
Ile Ala Tyr Arg Leu Ile Ile Thr Pro Gly Thr Phe Lys Glu Arg Ile
        595                 600                 605
Ile Lys Ser Ile Thr Pro Glu Thr Pro Thr Glu Ile Pro Cys Gly Asp
    610                 615                 620
Ile Arg Leu Asn Ala Val
625                 630
```

SMFRET WITH MEMBRANE PROTEINS

CROSS REFERENCE TO RELATED APPLICATION

The present application is a continuation application of U.S. Ser. No. 13/697,469, filed Jan. 29, 2013, which is the National Phase of PCT/US2011/036459, filed May 13, 2011, which claims priority to U.S. provisional application 61/334,483, filed May 13, 2010, and U.S. provisional application 61/382,721, filed Sep. 14, 2010, both of which are incorporated herein in their entirety.

GOVERNMENT FUNDING

This invention was made with Government support under Grant Number GM079238, MH054137, DA17293, DA022413, DA023694, and DA12408 awarded by National Institutes of Health. The United States Government has certain rights in the invention.

INCORPORATION BY REFERENCE OF SEQUENCE LISTING

The Sequence Listing in the ASCII text file, named as 26209_SEQ.txt of 22 KB, created on May 13, 2011 and submitted to the United States Patent and Trademark Office via EFS-Web, is incorporated herein by reference.

BACKGROUND

Imaging biological processes at the single-molecule scale using single-molecule FRET (smFRET) techniques (Roy, et al., Nature Methods 5: 507-516 (2008)) enables the direct observation of the temporal and spatial dynamics intrinsic to biopolymers. smFRET provides data that are inaccessible using other methods such as bulk experimental studies and, importantly, bridges the technological gap between current techniques to obtain static information about molecular architecture and the fundamentally dynamic nature of biological processes. As this technology develops, it is likely that smFRET studies of the dynamics of ligand-binding will be industrialized so that drug discovery and development companies can capitalize on them.

smFRET studies have been carried out on many kinds of biopolymers—nucleic acids and proteins, including intracellular and transmembrane proteins (Harms G S., Biophys J. 85: 1826-1838 (2003); Kaestner C N et al. Biophys J. 84:1651-1659 (2003); Margittai, M. et al. Proc. Natl. Acad. Sci. U.S.A. 100(26): 15516-15521 (2003)); single proteins; and protein complexes such as the ribosome and F1-ATPase. Most studies have been performed using surface-tethered molecules in a bath of biological, aqueous solutions. More recently, and to only a limited extent, surface-tethered proteins have been investigated that are sequestered in micelles, a strategy that promotes solubility of membrane proteins outside of the lipid bilayer. More recently, an smFRET study was performed on a soluble protein in a living cell Sakon J J et al., Nat Methods. 7(3):203-5 (2010).

Few studies to date have been performed on the dynamics of ligand-dependent conformational changes in biopolymers (Feldman M B, et al. Nat Chem Biol. 6(3):244. (2010); Munro, J. B., et al. EMBO J. 29(4):770-781 (2010)). However, these studies have not observed conformational, ligand-dependent dynamics of a membrane protein at the single-molecule scale using FRET. For the previous two to three decades, membrane protein dynamics have been inferred from electrophysiology voltage-clamp methods, where current can be measured. However, this approach is an indirect method that only applies to proteins that transport large fluxes of ions; little or no information is provided about the physical basis of the conformational change (e.g. amplitudes of motion and/or elements undergoing conformational changes). Harms G S., Biophys J. 85: 1826-1838 (2003) combines electrophysiology measurements with fluorescence by showing a single fluorescently labeled protein in the clamp. Single, fluorescently-labeled membrane protein fragments have also been visualized in ways similar to that described in Kaestner C N et al. Biophys J. 84:1651-1659 (2003); however, these studies used protein fragments instead of whole protein, and measured only the presence or absence of fluorophores as opposed to protein conformational dynamics. FRET as described in Majumdar, D. S. et al., Proc. Natl Acad. Sci. USA 104, 12640-12645 (2007) was performed using confocal imaging of freely diffusing molecules, where conformational dynamics cannot be measured due to the fast time scale of diffusion (microseconds) through the imaging volume.

smFRET studies are limited by many factors. One major limitation is the tendency of the fluorophores to photobleach (lose fluorescence) in a matter of seconds due to the high light intensity required for smFRET. Also, due to the rapid nature of many biological processes, protein interactions and FRET energy transfer may occur in a fraction of a second. Other factors limit the time scale as well. For example, capturing FRET where molecules are freely diffusing limits the time scale significantly because molecules will move rapidly out of the field of view. Thus, time frames for smFRET studies are generally measured on a scale of microseconds. Such limitations prevent extended study of many protein dynamics, such as the dynamics of a transmembrane transporter protein moving back and forth between an open conformation, allowing transportation across the plasma membrane, and a closed conformation, blocking such transportation.

SUMMARY

In one aspect, this disclosure is directed to a method of conducting dynamic single-molecule fluorescence studies on a membrane protein. The method generally involves obtaining a membrane protein which is labeled with fluorophore at one or more sites, and is placed in a membrane protein carrier; immobilizing the membrane protein or the carrier onto a solid surface; imaging the immobilized membrane protein to acquire fluorescence data over a period of time; and correlating the fluorescence data with conformational changes in the membrane protein.

In specific embodiments, the dynamic single-molecule fluorescence studies are dynamic single-molecule fluorescence resonance energy transfer (smFRET) studies in which a pair of fluorophores are utilized to assess conformational dynamics of a membrane protein.

In another aspect, this disclosure is directed to a method of screening for compounds that affect the conformational dynamics of a membrane protein. Such method generally involves conducting dynamic single-molecule fluorescence studies on the membrane protein in the absence of a test compound and in the presence of a test compound, respectively, and comparing the fluorescence data of said membrane protein in the absence of said test compound with the fluorescence data of said membrane protein in the presence of said test compound. Such comparison provides a basis for determining whether the test compound affects the conformational dynamics or any function or activity of the membrane protein.

In specific embodiments, the dynamic single-molecule fluorescence studies performed for screening a compound are dynamic single-molecule fluorescence resonance energy transfer (smFRET) studies in which a pair of fluorophores are utilized to assess conformational dynamics of a membrane protein.

In still another aspects, the disclosure is directed to mutant membrane proteins made for affixing one or more fluorophores suitable for conducting dynamic single-molecule fluorescence studies. Reagents and kits including, for example, a composition containing a mutant membrane protein together with a membrane protein carrier, optionally immobilized on a solid surface, are also disclosed.

BRIEF DESCRIPTION OF DRAWINGS

FIG. 8: Substrate binding and transport activity for double-labeled LeuT. Several double cysteine mutant LeuT samples were labeled with Cy3 and Cy5 (1:1 molar ratio) and purified in detergent. Binding activity was assessed by measuring of 3H-Leu binding to LeuT using a scintillation proximity assay (SPA). Dye-labeled LeuT was reconstituted into liposomes, and transport activity was assessed by measuring the rate of 3H-Ala (1 μM) accumulation in proteoliposomes in 50 mM Tris/Mes (pH 8.5), 50 mM NaCl at room temperature for 10 min. Errors are the standard deviation of three separate experiments.

FIG. 9: Estimation of distances from FRET values. For each dye-labeled sampled under each solution condition, FRET data were summed into histograms (bin size=0.015) and fit to a sum of Gaussian distribution functions. The observed FRET values are distorted by spectral bleed-through (also referred to as crosstalk) that arises from imperfections in the spectral separation using dichrioic mirrors. As a result, some fraction ($\alpha$) of Cy3 emission appears as Cy5 intensity and some fraction ($\beta$) of Cy5 emission appears as Cy3 intensity. To arrive at estimated distances for each FRET value the following correction for bleed-through was applied to the uncorrected FRET values:

Figures 1A, 1B, 1C, 1D:
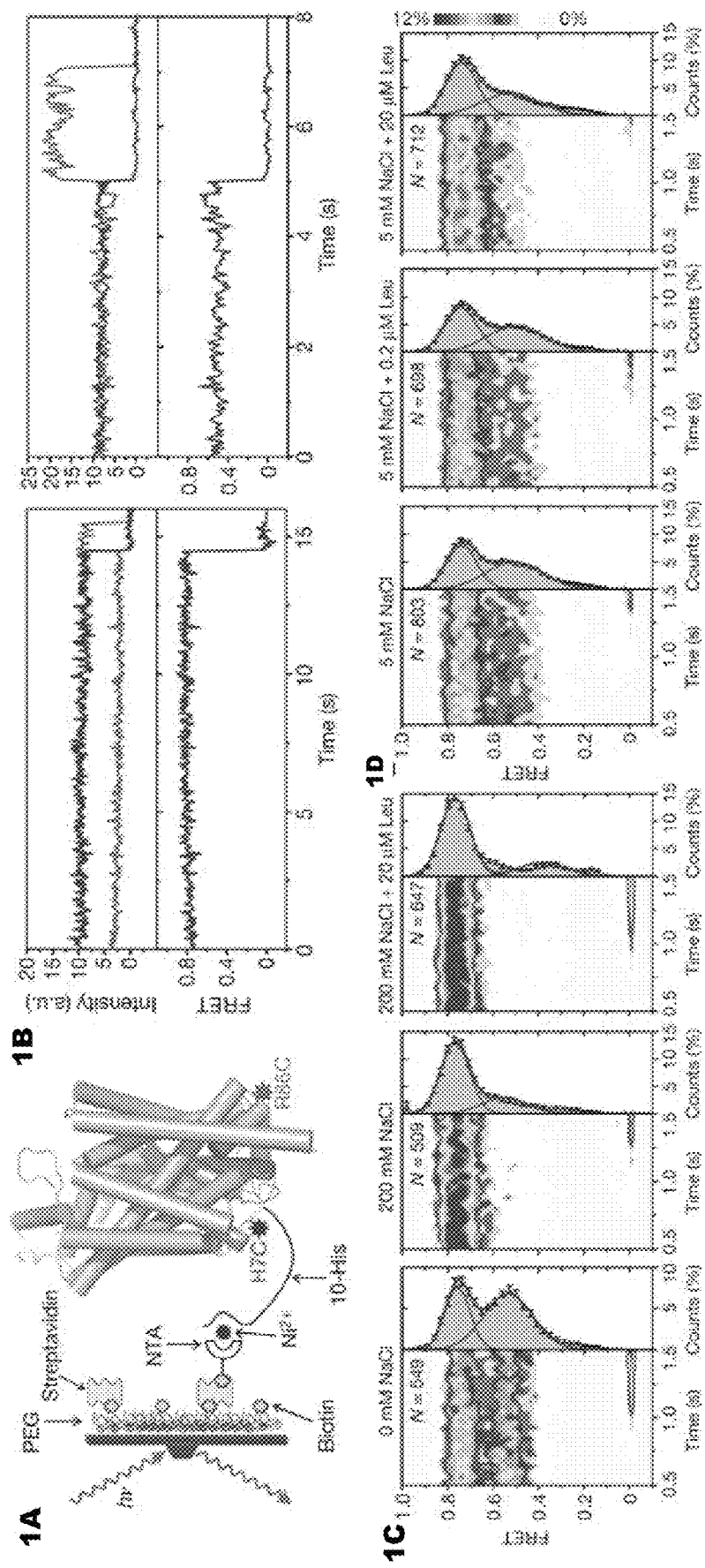
FIG. 1A-1D: Single-molecule imaging of LeuT. (A) His-tagged, dye-labeled LeuT-H7C/R86C was immobilized by biotin-NTA-Ni2+ to the streptavidin-treated surface. (B) Representative fluorescence (Cy3 donor in green, Cy5 acceptor in red) and FRET (grey) time traces from experiments in 200 mM KCl. (C) FRET traces and histograms for experiments performed in 0 mM NaCl (left), 200 mM NaCl (centre), and 200 mM NaCl with 20 μM leucine (right). Each two-dimensional histogram was summed over time, filtered to remove fluorophore dark states (see Examples), and fit to the sum (red) of two Gaussian distributions (blue) to estimate the mean value and relative occupancies of each FRET state. (D) FRET traces and histograms are shown for experiments performed in 5 mM NaCl with no substrate (left), 5 mM NaCl with 0.2 μM leucine (centre) and 5 mM NaCl with 20 μM leucine (right). Scale on right indicates the relative population.

$$E = \frac{E_{obs} - \alpha}{1 - \beta - \alpha},$$

where $\alpha=0.075$ and $\beta=0.155$ were estimated from the fluorescence emission spectra of Cy3 and Cy5 and the transmission spectra of optical components in the light path. Corrected FRET values were then used to calculate an average distance (R) between Cy3 and Cy5 in each experiment (Examples). The inventors estimate the upper limit of the error in the distances to be ±5 Å.

FIG. 10A-10F: Effect of Na$^+$ on LeuT dynamics. smFRET imaging of surface-immobilized Cy3/Cy5-labeled LeuT (H7C/R86C) was performed in buffer containing various concentrations of Na$^+$. Experiments were performed with 160 ms time resolution, except for 30 and 50 mM Na$^+$, where the integration time was increased to 400 ms to reduce photobleaching and better estimate the long dwell times in these conditions. (A) H7C/R86C-LeuT labeled with Cy3 and Cy5 (stars) was immobilized via a biotin acceptor peptide (BAP) on a passivated glass surface and illuminated using total internal reflection. FRET traces (>110 per condition) were collected with varying concentrations of $Na^+$ (160-ms time resolution for all, except 30-50 mM with 400 ms). (B) The FRET data were filtered to remove fluorophore dark states (see Methods) and summed into a histogram to compare occupancy in specific FRET states. (C) The FRET traces were idealized with a two state model. The fraction of time spent in the lower-FRET open state (squares) and the high-FRET closed state (circles) was calculated from the idealization. (D) Transition density plots were created by plotting the average FRET value before (x-axis) and after (y-axis) each transition between distinct FRET states. Transitions to dark states were computationally removed for clarity. (E) Average dwell times in the open state (squares) and the closed state (circles) were estimated using maximum likelihood fitting. (F) A representative single-molecule trajectory is shown (Cy3 intensity in green, Cy5 intensity in red, FRET in blue, and idealized FRET in red) where imaging started in the absence of $Na^+$ followed by solution exchange to 200 mM $Na^+$ at the 2 minute time point.

FIG. 11A-11E: Effect of leucine on LeuT dynamics. smFRET imaging of surface-immobilized Cy3/Cy5-labeled LeuT (H7C/R86C) was performed at 160 ms time resolution in buffer containing 2 mM NaCl and various concentrations of L-leucine (Leu). (A) The FRET data were filtered to remove fluorophore dark states and summed into a histogram to compare occupancy in specific FRET states. (B) The FRET traces were idealized with a two state model. The fraction of time spent in the lower-FRET open state (squares) and the high-FRET closed state (circles) was calculated from the idealization. (C) Average dwell times in the open state (squares) and the closed state (circles) were estimated using maximum likelihood fitting. (D) Transition density plots were created by plotting the average FRET value before (x-axis) and after (y-axis) each transition between distinct FRET states. Transitions to dark states were computationally removed for clarity. (E) A representative single-molecule trajectory is shown from an experiment where imaging started in 2 mM $Na^+$ followed by solution exchange to 2 mM $Na^+$ and 250 μM Leu at the 2 minute time point.

FIG. 12A-12F: Effect of alanine on LeuT dynamics. smFRET imaging of surface-immobilized Cy3/Cy5-labeled LeuT (H7C/R86C) was performed at 160 ms time resolution in buffer containing 2 mM Na+ and various concentrations of L-alanine (Ala). (A) The FRET data were filtered to remove fluorophore dark states (see Examples) and summed into a histogram to compare occupancy in specific FRET states. (B) The FRET traces were idealized with a two state model. The fraction of time spent in the lower-FRET open state (squares) and the high-FRET closed state (circles) was calculated from the idealization. (C) Average dwell times in the open state (squares) and the closed state (circles) were estimated using maximum likelihood fitting. (D) Transition density plots were created by plotting the average FRET value before (x-axis) and after (y-axis) each transition between distinct FRET states. Transitions to dark states were computationally removed for clarity. (E) A representative single-molecule trajectory is shown from an experiment where imaging started in 2 mM $Na^+$ followed by solution exchange to 2 mM $Na^+$ and 2 mM Ala at the 2 minute time point. (F) A representative single-molecule trajectory is shown from an experiment where imaging started in 2 mM $Na^+$ followed by solution exchange to 2 mM $Na^+$ and transport inhibitor clomipramine (CMI) at the 2 minute time point.

FIG. 13A-13D: Effect of transport inhibitors on LeuT dynamics. (A) Transition density plots were created by plotting the average FRET value before (x-axis) and after (y-axis) each transition between distinct FRET states. (B-C) The fold change in the rate of transitioning from the open state to the closed state (open bars) and from the closed state to the open state (filled bars) is shown for Cy3/Cy5-labeled LeuT (H7C/R86C) in 10 mM $Na^+$ with 250 μM Ala alone or with 0.1 mM CMI, or 35 mM OG versus without Ala. (D) A representative single-molecule trajectory is shown from an experiment where imaging started in 10 mM Na+ and 2 mM Ala and was exchanged to buffer including 10 mM $Na^+$, 2 mM Ala, and 0.1 mM CMI at the 2 minute time point.

FIG. 14A-14D: Effect of S1 and S2 site mutations and of $Li^+$ on inward-open and inward-closed dwell times. (A) Binding of $^3$H-alanine in buffer containing 50 mM $Na^+$ was measured for wild-type (WT, squares), L400S (grey circles), and F253A (triangles) LeuT. Binding measurements were also performed in buffer containing 150 mM $Li^+$ with wild-type LeuT (black circle). (B) Alanine uptake was measured for LeuT-WT, F253A and L400s in buffer containing 100 mM NaCl as well as in buffer containing 150 mM $Li^+$. (C-D) The fold change in the rate of transitioning from the open state to the closed state (C) and from the closed state to the open state (D) induced by 250 μM Ala is shown for WT, F253A, and L400S LeuT in 10 mM Na+ or for WT in 40 mM $Li^+$.

FIG. 15A-15D: smFRET imaging of surface-immobilized Cy3/Cy5-labeled H7C/R86C-LeuT was performed in buffer containing 250 μM alanine over a range of NaCl concentrations. (A) FRET traces were idealized using a two-state, hidden Markov model and the fraction of time spent in the low-FRET (squares) and high-FRET (circles) states is shown. Error bars are the standard deviation of 1000 bootstrap samples. (B) Maximum likelihood analysis was performed on the idealizations to estimate the average lifetime of the open (squares) and closed (circles) states. Error bars are the standard deviation of 100 bootstrap samples. (C) Transition density plots of each condition, (D) A representative single-molecule trajectory is shown (Cy3 donor intensity in green, Cy5 acceptor intensity in red, FRET in blue and idealization in red), where the experimental conditions started in 0 mM NaCl and 2 mM Ala, followed by exchange to 2 mM NaCl and 2 mM Ala at the 2 minute time point.

FIG. 16A-16E: Fluorophore-labeled Tyt1 and $Glt_{Ph}$ can be immobilized via biotinylated liposomes and measured. Upper panel: Liposomes specifically immobilize at the quartz surface via a biotin-streptavidin bridge: (A) no liposomes; (B) non-biotinylated liposomes; (C) biotinylated liposomes. Lower panel: Individual Cy3 fluorophores, encapsulated within liposomes can be counted and their lifetime measured; (D) Four Cy3 molecules within a single liposome; (E) photobleaching rates measured by field analysis with and without oxygen scavenging.

Figures 17A, 17B:
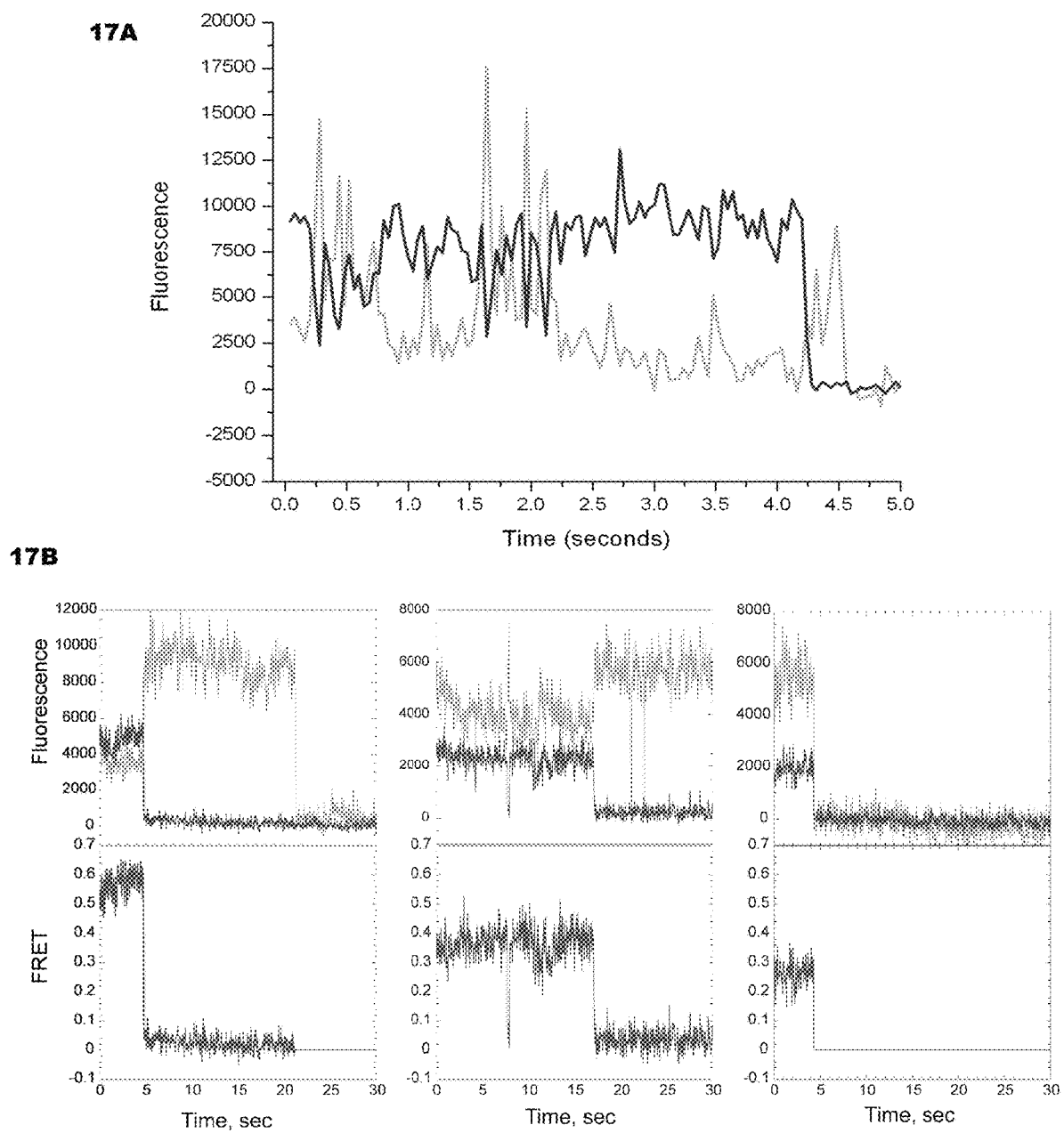

FIG. 17A-17B: smFRET data from donor- and acceptor-labeled Tyt1 and $Glt_{Ph}$. (A), Tyt1 in detergent; (B), liposome-embedded $Glt_{Ph}$. Representative single-molecules from each system are shown to illustrate time-dependent changes in smFRET on the millisecond time scale: Cy3 (green) and Cy5 (red). FRET efficiencies (blue). Step-wise loss of signal corresponds to the photobleaching of each single dye.

Figure 18:
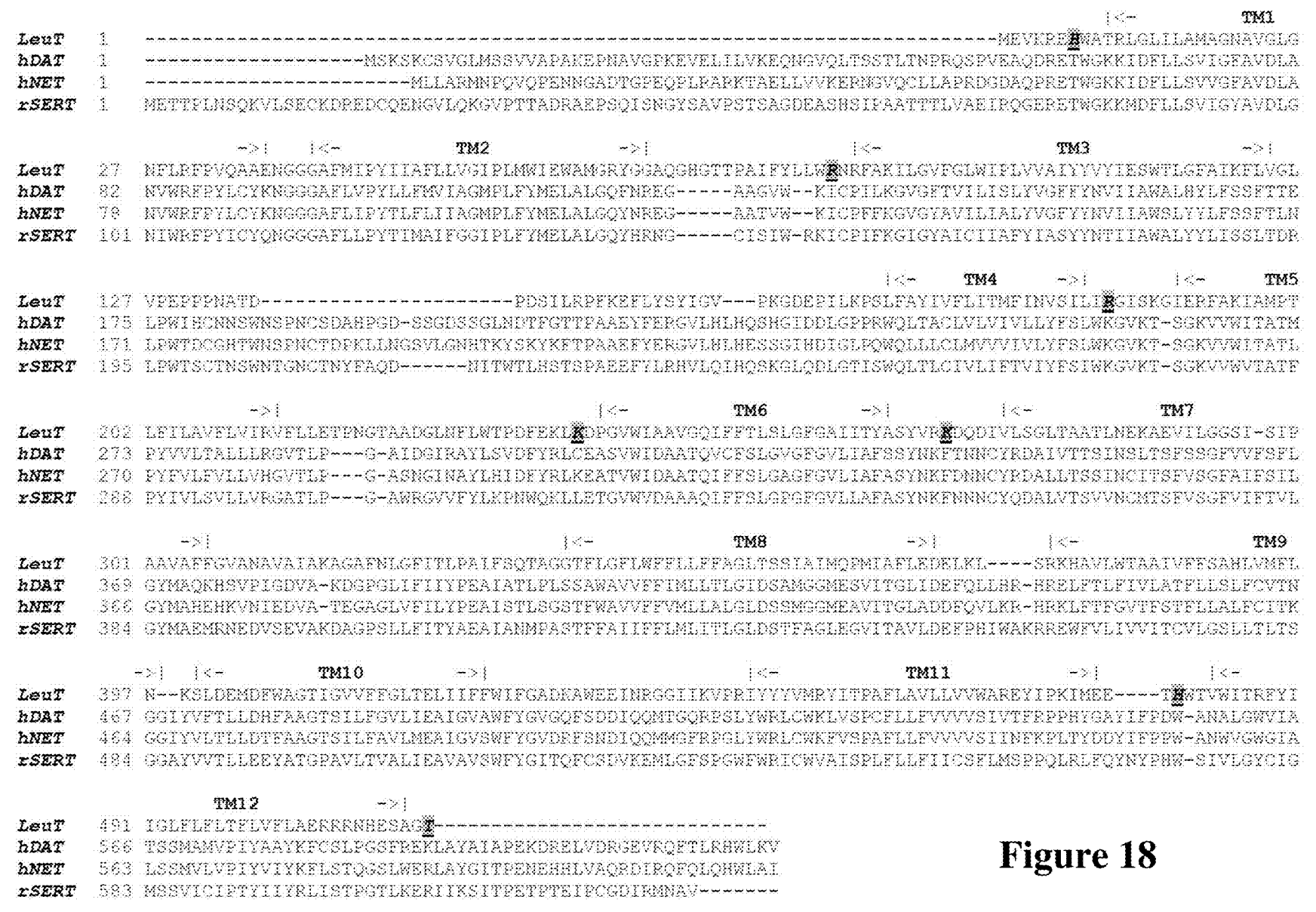

FIG. 18: Alignment of NSS proteins. NSS proteins aligned according to structural homology with LeuT (SEQ ID NO: 4; the last two amino acids of SEQ ID NO: 4, Gly-Thr, were part of the tag introduced into the native LeuT for crystallization). hDAT: SLC6A3 (human solute carrier family 6 (neurotransmitter transporter, dopamine) member 3), aka DAT1 or DAT (SEQ ID NO: 5); hNET is SLC6A2 (solute carrier family 6 (neurotransmitter transporter, noradrenalin) member 2), aka NET1 aka NAT1 aka SLC6A5 located on chromosome 16q12 (SEQ ID NO: 6); rSERT is SLC6A4 (solute carrier family 6 (neurotransmitter transporter, serotonin), member 4), located on 17q11.2 (SEQ ID NO: 7).

DETAILED DESCRIPTION

The inventors have, for the first time, successfully applied single-molecule fluorescence resonance energy transfer (smFRET) techniques to study the dynamics of a transmembrane protein and have overcome significant technical hurdles to do so. Without limiting to any particular theory, it is believed that the success results from, for example, the choice of sites on the membrane protein for labeling; the choice of solubilization, protein carrier, and purification conditions; the surface-immobilization strategy where for example, an epitope tag is linked to the C- or N-terminus of the membrane protein; the extension of fluorophore lifetime and the dampening of fluorophore photophysics; the implementation of computational strategies to sort the heterogeneous population of single-molecule FRET data; or a combination thereof.

As demonstrated herein, the inventors were able to observe and quantify ligand-dependent changes in conformational dynamics of a membrane protein at extended imaging time scale using smFRET techniques, which could be masked by ensemble averaging in bulk measurements or suppressed through crystallographic conditions.

Accordingly, this disclosure is directed to methods of conducting dynamic single-molecule fluorescence studies on a membrane protein which permits observation and quantification of conformational dynamics of a membrane protein. Also disclosed herein are mutant membrane proteins in which one or more mutations have been introduced for affixing a fluorophore, as well as compositions and reagents containing such mutant membrane proteins for conducting dynamic single-molecule fluorescence studies. The methods and compositions disclosed herein can be used in screening for compounds that enhance or reduce the activity of a membrane protein, useful for treating diseases associated with the malfunction of the membrane protein or alterations in membrane protein conformation.

In the following description, reference is made to the accompanying drawings that form a part hereof, and in which is shown by way of illustration specific embodiments which may be practiced. These embodiments are described in detail to enable those skilled in the art to practice the invention, and it is to be understood that other embodiments may be utilized and that changes may be made without departing from the scope of the present invention. The following description of example embodiments is, therefore, not to be taken in a limited sense.

Definitions

A "membrane protein" is a protein molecule that is attached to, integral to, or associated with the membrane of a cell or an organelle. More than half of all proteins interact with membranes. The genus of membrane proteins may be broken into species based on function of the membrane protein; for example, (i) structural proteins are attached to microfilaments in the cytoskeleton which ensures stability of the cell; (ii) cell adhesion molecules allow cells to identify each other and interact; (iii) membrane enzymes produce a variety of substances essential for cell function; (iv) membrane receptor proteins serve as connection between the cell's internal and external environments; (v) transport proteins play an important role in the maintenance of concentrations of ions and come in two forms: carrier proteins and channel proteins.

The genus of membrane proteins may also be grouped by the way the protein is related to a membrane, for instance: (i) integral membrane proteins that are attached to the membrane, including (a) transmembrane proteins that span the entire membrane and (b) integral monotopic proteins that are attached to the membrane from only one side; and (ii) peripheral membrane proteins that are attached either to the lipid bilayer or to integral proteins by a combination of hydrophobic, electrostatic, and other non-covalent interactions; and (iii) polypeptide toxins such as colicin A or alpha-hemolysin, and certain proteins involved in apoptosis, which are water-soluble but can aggregate and associate irreversibly with the lipid bilayers.

Transmembrane proteins can be further classified into four main types based on the position of the N- and C-terminal domains. Types I, II, and III are single pass molecules, while type IV are multiple pass molecules. Type I transmembrane proteins are anchored to the lipid membrane with a stop-transfer anchor sequence and have their N-terminal domains targeted to the ER lumen during synthesis (and the extracellular space, if mature forms are located on plasmalemma). Type II and III are anchored with a signal-anchor sequence, with type II being targeted to the ER lumen with its C-terminal domain, while type III have their N-terminal domains targeted to the ER lumen. Type IV is subdivided into IV-A, with their N-terminal domains targeted to the cytosol and IV-B, with a N-terminal domain targeted to the lumen. G protein-coupled receptors (GPCRs) are a particularly important subtype of Type IV transmembrane proteins and can be grouped into 6 classes based on sequence homology and functional similarity: Class A (or 1) (Rhodopsin-like); Class B (or 2) (Secretin receptor family); Class C (or 3) (Metabotropic glutamate/pheromone); Class D (or 4) (Fungal mating pheromone receptors); Class E (or 5) (Cyclic AMP receptors); Class F (or 6) (Frizzled/Smoothened). The very large rhodopsin A group has been further subdivided into 19 subgroups (A1-A19). More recently, an alternative classification system called GRAFS (Glutamate, Rhodopsin, Adhesion, Frizzled/Taste2, Secretin) has been proposed.

A "protein" is a compound made of naturally-occurring or artificial amino acids arranged in a chain. The natural amino acids in a polymer are generally joined together by the peptide bonds between the carboxyl and amino groups of adjacent amino acid residues. The amino acids in a polypeptide chain are linked by peptide bonds. Once linked in the protein chain, an individual amino acid is called a residue, and the linked series of carbon, nitrogen, and oxygen atoms are known as the main chain or protein backbone. The end of the protein with a free carboxyl group is known as the C-terminus or carboxy terminus, whereas the end with a free amino group is known as the N-terminus or amino terminus. The word "protein" also includes protein domains, protein fragments, peptides, and polypeptide. "Protein" is generally used to refer to the complete biological molecule in a stable conformation, whereas peptide is generally reserved for a short amino acid oligomer usually 20-30 residues in length or less. Polypeptide can refer to any single linear chain of amino acids, usually regardless of length, but often implies an absence of a defined conformation.

"Protein purification" means the process of removing a protein from a cell or solution in which it was expressed and isolating it so that it can be studied. Many techniques exist in the art for protein purification. Processes and reagents especially amenable for use with membrane proteins include NABB-based techniques (Bannerjee S et al., J Mol Biol. 2008 Apr. 4;377(4):1067-81. Epub 2008 Feb. 2. and Published PCT Application WO2009097587); styrene maleic acid lipid particles (SMALPs) (Knowles T J et al., J Am Chem Soc. 2009 Jun. 10;131(22):7484-5); and nanodisks (see for example Borch J et al., Biol Chem. 2009 August; 390(8):805-14). Liposomes and micelles also may be used in a protein purification process. Further, if cell-free or in vitro expression systems are employed, as are known in the art, to express a membrane protein, they may be more readily purified and incorporated into a vehicle for imaging. See examples section as well.

A "vehicle" or "protein carrier" is a carrier for a protein such as a membrane protein, and may be reagents used in protein purification including detergents and lipids, or nanoparticles such as NABBs and SMALPs. Other proteins, macromolecular complexes such as ribosomes, or liposomes can also be used as carriers of a membrane protein. A cell can also be used as a carrier of a membrane protein. The choice of membrane protein carrier, such as the type of detergent used, and the conditions under which purification is conducted, is made so as to not affect protein function.

"Immobilization" means attaching a vehicle or protein to an inert, insoluble material. There are different ways in which one can immobilize, including but not limited to: adsorption on glass, alginate beads or matrix; entrapment; imbedding in a matrix such as agarose or polyacrylimide; and cross-linkage. Use of a spacer molecule like poly (ethylene glycol) may help reduce the steric hindrance when a vehicle or protein is immobilized. Common reagents used for immobilization include biotin-avidin pairings. Biotin can be incorporated into lipids used in reconstitution or onto the protein using a noncovalent linkage such as biotin-NTA interacting with a His epitope tag on the protein, or can be incorporated covalently either through addition of a biotin acceptor sequence and treatment with biotin ligase or by direct chemical modification with biotin through cysteine or lysine directed reactions. Biotin can also be incorporated into a protein by reacting a non-natural amino acid residue introduced in the protein with a biotin hydrazide, for example, as described by Wang et al. (Proc. Natl. Acad. Sci. USA, 2003 Jan. 7; 100(1):56-61. Epub 2002 Dec. 23). Tris-NTA biotin (see, e.g., Cheng et al., Anal Chem. 2008 Apr. 1; 80(7):2564-73. Epub 2008 Feb. 27) is also well suited for protein immobilization for dynamic studies. Epitope tagging or click chemistry can also be used for immobilization of the protein or protein carrier to a solid support.

"Single-molecule fluorescence resonance energy transfer" (or "smFRET") is the application of FRET techniques to study a single molecule with at least two fluorescent labels, or the interaction of at least two molecules, each with a label. Fluorescence Resonance Energy Transfer (FRET) is a nonradiative pathway by which a molecule in an electronic excited state may relax back to the more stable ground state. The transfer of energy occurs through space via dipole-dipole interaction: energy from the excited-state molecule (the donor fluorophore) may transfer to a neighboring molecule (the acceptor fluorophore) given significant degree of spectral overlap between donor emission and acceptor absorption, properly oriented dipole moments of the interacting dye molecules, and the appropriate distance between the two fluorophores. In smFRET the donor and receptor fluorophores are on the same molecule, or are on different molecules that interact, bringing the two fluorophores into proximity. The detection of FRET at the single-molecule scale enables the direct measurement of conformational events and/or binding processes on biologically-relevant time scales.

Dynamic smFRET refers to the use of smFRET techniques to interrogate biological samples of interest over extended periods of time in order to quantify changes in the amount of time that the sample spends in its various conformational states, i.e., the sample's conformational dynamics. By measuring time-dependent conformational dynamics in a biomolecule, insights into the physical parameters of motion are obtained that relate to regulation and function. An extended period of time for smFRET studies can be a period from 100 milliseconds, or 2-3 seconds, up to at least a minute or over several minutes, depending on the conformational time dynamics of the protein under interrogation.

A "fluorophore" is a component of a molecule which causes a molecule to be fluorescent. It is a functional group in a molecule which will absorb energy of a specific wavelength and re-emit energy at a specific wavelength. The amount and wavelength of the emitted energy depend on both the fluorophore and the chemical environment of the fluorophore. Fluorescein isothiocyanate (FITC), a reactive derivative of fluorescein, has been one of the most common fluorophores chemically attached to other, non-fluorescent molecules to create new fluorescent molecules for a variety of applications. Other common fluorophores are derivatives of rhodamine (TRITC), coumarin, pyrene, and cyanine. Newer generations of fluorophores such as maleimide derivative dyes, CF dyes, the FluoProbes dyes, the DyLight Fluors, the Oyester dyes, the Atto dyes, the HiLyte Fluors, and the Alexa Fluors are believed to perform better (more photostable, brighter, and/or less pH-sensitive) than other standard dyes of comparable excitation and emission. In specific embodiments, fluorophores from the cyanin family and alexa family are used in the method disclosed herein. Fluorophores combined with one or more fluorophore-protective agents, such as TSQs (triplet state quenchers), in particular Cyclooctatetraene, Trolox and NBA, which are particularly useful for practicing the present invention, are described in International Application PCT/US10/24824 (published as US 2010/096720), which is incorporated herein by reference in its entirety. A protective agent, which may be a molecule or moiety, has the ability to alter the photophysical properties of a fluorophore, particularly by altering the light state-dark state (i.e., singlet-triplet) occupancy distribution or relaxation pathway of excited and relaxing electrons. The protective agent may be attached adjacent to or directly to the fluorophore, or it may be free in the solution surrounding the fluorophore. The ability of a molecule to function as a protective agent is often evidenced by its ability to alter the blinking and/or photobleaching characteristics of a fluorophore, thereby improving fluorescent quality.

One aspect of this disclosure pertains to a method of conducting dynamic single-molecule fluorescence studies on a membrane protein.

The single-molecule fluorescence approach disclosed herein applies to any membrane protein as defined herein above, i.e., including but not limited to integral membrane proteins that attached to the membrane (such as transmembrane proteins and integral monotopic proteins that are attached to the membrane from one side), peripheral membrane proteins that are temporarily attached to the lipid bilayer or to an integral membrane protein, and proteins which are water-soluble but can aggregate and associate irreversibly with the lipid bilayers.

In some embodiments, single-molecule fluorescence studies are conducted on a transmembrane protein. Examples of transmembrane proteins include, but are not limited to, neurotransmitter:sodium symporters (NSS), G-protein coupled receptors (GPCR), Tyt1, and excitatory amino acid transporters (EAAT (such as Gltph)).

In specific embodiments, single-molecule fluorescence studies are conducted on an NSS protein. NSS proteins terminate neuronal signaling by recapturing neurotransmitter released into the synapse. These secondary active transporters mediate the accumulation of their substrates across the plasma membrane in a co-transport (symport) mechanism driven by the $Na^+$ electrochemical gradient. NSS for the biogenic amines dopamine, norepinephrine, and serotonin, are targeted by numerous drugs, including the widely abused psychostimulants cocaine and amphetamine, as well as antidepressants.

The superfamily of proteins utilizing $Na^+$ co-transport (symport) mechanisms includes the neurotransmitter: sodium symporters (NSS) and the excitatory amino acid transporters (EAAT) sub-families. The substrates of EAAT proteins include biogenic amines such as sugars, amino acids, and osmolytes. This NSS family of transporters includes the dopamine transporter (DAT), the major molecular target responsible for both the rewarding properties and abuse potential of cocaine and related psychostimulants. The homologous neurotransmitter transporters for serotonin and norepinephrine, SERT and NET, are primary targets of antidepressant drugs. Other family members that transport GABA and glycine are targets for drugs in development to treat epilepsy and schizophrenia, respectively.

Genes encoding more than 200 putative NSS homologs have been identified in prokaryotic genomes (Beuming, T. et al., Mol. Pharmacol. 70, 1630-1642 (2006)), including LeuT, a prokaryotic NSS homolog from the thermophile *Aquifex aeolicus*. The crystal structure of LeuT revealed an occluded conformation in which one leucine (Leu) substrate and two $Na^+$ are bound deep within the protein (Yamashita, A. et al., Nature 437, 215-223 (2005)). The existence of two additional LeuT conformations, outward-facing and inward-facing, has been proposed on the crystal structure (Yamashita, A. et al., Nature 437, 215-223 (2005)), in accordance with the alternating access model for transporters proposed earlier (Jardetzky, O., Nature 211 (5052), 969 (1966)). As illustrated herein, the inventors have conducted single-molecule fluorescent studies, including single-molecule FRET analysis, on LeuT. These studies have elucidated informative sites for labeling and permitted observation and quantification of conformational dynamics of LeuT at extended imaging time scales, which reveal both structural and mechanistic insights previously difficult or impossible to discern using other methods.

In other specific embodiments, single-molecule fluorescence studies are conducted on a GPCR. Examples of GPCRs include the dopamine D2 receptor, adenosine A2A receptor, metabotropic glutamate receptors, and beta1 and beta2 adrenergic receptors.

As disclosed herein, the present method of conducting dynamic single-molecule fluorescence studies typically involves providing a membrane protein labeled with one or more fluorophores, wherein the membrane protein is placed in a membrane protein carrier, and immobilized directly or indirectly to a solid support. The immobilized membrane protein is then imaged to acquire fluorescence data, which can then be analyzed to determine membrane protein dynamic activity such as but not limited to protein conformational changes, dimerization, ligand binding, and/or interactions with other membrane or soluble proteins.

In some embodiments, the membrane protein is labeled with a single fluorophore, and the fluorescence data (e.g., intensity, blinking) acquired from imaging the immobilized membrane protein can reveal and correlate with conformational changes of the membrane protein. Binding can be measured by co-localization of fluorescence.

When a fluorescent molecule is excited, such molecule can relax in one of three ways: fluorescence, entering into the triple state (aka "quenching" or "blinking"), or heat dissipation. Because the environment of the fluorophore can influence the choice of relaxation, and because the conformational change of the membrane protein can affect the environment of the fluorophore, the measurement of the fluorescence intensity or frequency of blinking from a singularly labeled membrane protein can reflect or correlate with the conformation of the membrane protein. For example, when a membrane protein changes its conformation such that the fluorophore is more exposed to water, the excited fluorescent molecule is more likely to relax through heat dissipation hence weaker fluorescence emission. Alternatively, a change in conformation, which may result in an interaction or increased interaction of the fluorophore with other molecules in the environment (such as a micelle), may cause more blinking in some instances, or less blinking in other instances.

In embodiments where the membrane protein is labeled with a single fluorophore for studying conformational changes, flurophores which have relatively long excited-state lifetimes are generally preferred. Such flurophores are typically environmentally sensitive to quenching or heat dissipation relative to flurophores which have short excited-state lifetimes. In this context, excited-state lifetimes of at least 0.5 nanoseconds are considered to be sufficiently long for use in the present method. Flurophores that have relatively long excited-state lifetimes include cy5, pyrene, coumarin, and many others known in the art. On the other hand, an example of a fluorophore with a relatively short excited-state lifetime is cy3. In other embodiments, instead of labeling a membrane protein with a single fluorophore, two fluorophores are used to label the membrane protein, with one being the donor and the other one the acceptor. The fluorescence data acquired from imaging the immobilized membrane protein, as a result of fluorescence resonance energy transfer (FRET) from the donor to the acceptor, or as a result of co-localization of fluorescence, can reveal and correlate with conformational changes of the membrane protein.

In one embodiment, a membrane protein and one or more other proteins such as ligands, soluble proteins, or additional membrane proteins, are each labeled with a fluorophore, and the fluorescence data acquired from imaging the proteins can reveal and correlate with membrane protein oligomerization, ligand binding, and/or interactions with other proteins.

When a pair of fluorophores are utilized, in some embodiments, a single molecule of a membrane protein is labeled with the pair of fluorophores, while in other embodiments, two separate molecules or preparations of a membrane protein or alternatively, two different proteins (e.g., two different membrane proteins, or a membrane protein and a soluble protein) which interact with each other (e.g., in a homo or hetero dimer) are labeled with the donor and the acceptor fluorophores, respectively.

Fluorophores may be attached to a target protein by a number of means. For example, epitope tags are introduced into a target protein by genetic engineering of the epitope of interest into the protein, which allows labeling by covalent or other attachment of the fluorophore to the protein following recombinant protein expression and purification. A specific example is a fluorophore (e.g., Cy5) that binds non-covalently to a membrane protein through a Nickel-NTA or tris NTA interaction via a His-6 tag. Examples of epitope tags include FLAG, snap, clip, halo, and his-tags. For additional epitope tags see, ie, Brizzard, B., BioTechniques 44:693-695 (2008). Snap-tagging for FRET study of membrane protein heteroassembly is detailed in Maurel, D., et al, Nat. Methods 5(6):561-567 (2008). The fluorophore can also be incorporated by engineering fluorescent fusion proteins, such as green fluorescent protein (GFP), into the protein of interest. For fluorophore labeling within a cell, membrane permeant fluorophores can be used or a fluorophore can be injected into the cell interior for studies of intracellular protein activities. Additional means of labeling include expressed protein ligation, as described by e.g., Muralidharan and Muir in Nat Methods 3(6):429-38 (2006), and by Muir in Annu Rev Biochem 72:249-89 (2003). Essentially, a target protein is expressed with one half of the intein. A synthetic peptide, labeled with a fluorophore, serves as the second half of the intein and will react and ligate to the first half of the intein with the target protein.

Labeling can be also achieved through attachment, e.g., covalent linkage, of a fluorophore to an amino acid which is present in the native protein, or alternatively an amino acid which is introduced into the protein. Because selection of the amino acid position(s) for labeling is important to the effectiveness of the single-molecule fluorescence studies, labeling is often achieved through attachment of a fluorophore to an amino acid which is introduced to a selected position in a membrane protein.

The introduced amino acid can be a natural amino acid or an unnatural amino acid. A "natural amino acid" refers to an amino acid that is naturally incorporated into polypeptides in organisms. There are 22 natural amino acids, 20 of which are encoded by the universal genetic code. A "non-natural amino acid" refers to an amino acid that is not naturally incorporated into proteins by cellular machinary. Non-natural amino acids include amino acids that are in proteins but are are formed by post-translational modification (e.g., hydroxyproline), as well as amino acids that are not found in naturally occurring proteins.

The choice of amino acid being introduced for purposes of labeling may depend on the fluorophore to be attached. For example, if a maleimimide dye is used, a cysteine will be introduced for covalent attachment of the dye. If the membrane protein includes one or more native cysteines, these may be used for labeling. Alternatively, the cysteine residue(s) present in the native membrane protein can be substituted with other suitable amino acids so as not to interfere with the labeling through an introduced cysteine at a selected site. For attachment of other fluorophores, other amino acids mutations can be introduced, including substitution mutations using an unnatural amino acid, using techniques known in the art; see, e.g., Munro, J. B., et al. EMBO J. 29 (4):770-781 (2010). Fluorophores may also be attached using other chemistries, such as click chemistry (for review of click applications for covalent attachment in biomolecules, see Nwe, K., et al., Cancer Biother. Radiopharm. 24(3):289-302 (2009)).

An amino acid can be introduced into a selected position in a membrane protein by well known mutagenesis techniques, resulting an insertion mutation or a substitution mutation. Methods to mutate a native protein to introduce an unnatural amino acid are also known in the art; see, e.g., Munro et al. (supra); Chin et al., Science 301: 964-967, 2003).

The site(s) or position to which an amino acid is introduced for purposes of fluorophore attachment is selected based on several considerations.

Generally speaking, the introduced mutation ideally does not substantially affect the tertiary structure or function of the membrane protein such that the fluorescent data observed reflects the conformational dynamics of the wild type protein without the mutation. Therefore, the mutation site (the labeling site) is typically selected to be outside of an activity domain of the membrane protein, and in specific embodiments, distal to an activity domain of the membrane protein. By "an activity domain" it is meant a domain that performs at least one aspect of the functions or actions of the membrane protein, including, e.g., a ligand binding domain, a catalytic domain, or the like. In other embodiments, mutations for labeling are introduced within or near an activity domain; for example, His7 in LeuT which is near the intracellular gate where the observed dynamics occur.

Sites that do not not substantially affect the tertiary structure or function of a membrane protein can be found within sequences or segments of the protein that are not conserved across homologous species or members of the family to which the membrane protein belong; or alternatively, the sites can be amino acids that are not conserved across homologous species or members of the family. As used herein, a "conserved amino acid sequence" refers to a sequence which includes identical amino acids, or functionally or structurally equivalent, though not necessarily identical, amino acids at analogous parts of proteins across homologous species or members of a protein family. For a given part or fragment of a protein family, the sequence identity or similarity should be at least 30% across the full length of a given fragment to be considered conserved, with possible identities or similarities of at least 40%, 50%, 60%, 70%, 80%. 90% or greater. A "conserved amino acid" refers to an amino acid that is either identical or functionally or structurally equivalent at analogous positions across homologous species or members of a protein family. Where an identical amino acid or functionally or structurally equivalent amino acid is found in at least 50%, 60%, 70%, 80% or more of the members of a family, such amino acid can be considered as highly conserved.

To illustrate, NSS family members have regions of high homology and regions of low (or no) homology. Alignment of prokaryotic and eukaryotic NSS proteins (Beuming, T. et al., Mol. Pharmacol. 70, 1630-1642 (2006)) finds that some transmembrane (TM) domains show low conservation (for example, TM4/5 shows only 11% sequence identity between LeuT and dopamine transporter) while amino acid residues surrounding substrate binding sites show high conservation (for example, LeuT residue L25 shows 94% conservation with all eukaryotic equivalent residues and 100% conservation with dopamine, norepinephrine, and serotonin receptors; LeuT residue G26 shows 85% conservation with all eukaryotic proteins and is identical in the serotonin receptor but differs in norepinephrine and dopamine receptors). Y268 in LeuT and Y335 in the dopamine receptor are considered functionally or structurally homologous or equivalent residues; a mutation in either residue interferes with transport capacity (Kniazeff, J. et al., J. Biol. Chem. 283, 17691-

17701 (2008)). On the other hand, mutations in amino acids which show low conservation (such as LeuT residues H7, R86, and H480, which show no homology to human NSS equivalent residues, and LeuT residue K239, which is conserved with human norepiniphrine receptor but not other equivalent human NSS residues) can be mutated without affecting protein function (see Examples).

To maintain the tertiary structure and function of the membrane protein under interrogation as much as possible, substitution mutations can be made at amino acids which are similar in size and hydrophobicity to the amino acid being introduced for labeling. For example, for making cysteine substitutions, amino acids such as serine, threonine, among others, can be considered as target positions, whereas proline may not be an ideal target position due to its unique propensity to distort the polypeptide backbone.

Additional considerations are given in selecting a labeling site to optimize smFRET signals, including selecting sites having accessibility to solvent, facing the intracellular or extracellular space rather than facing the lipid membrane bilayer, sites associated with significant conformational changes between active and inactive states or conformations of the membrane protein, and sites that provide efficient fluorophore coupling, low nonspecific labeling, low anisotropy parameters, and that permit free spinning of fluorophores.

In cases where a pair of fluorophores are utilized in labeling, the labeling sites are selected such that the distance between the fluorophores depends on the conformation of the membrane protein; therefore an increase or decrease in distance between the fluorophores reflects a change in conformation of the membrane protein.

In some embodiments, a pair of fluorophores are attached to amino acid positions that are separated from one another in the protein tertiary structure by a distance approximating the $R_0$ for the donor fluorophore and acceptor fluorophore. The Forster relationship defining the efficiency of FRET as a function of distance is unique for each dye pair. For any pair of fluorophores, the distance between the pair wherein 50% energy transfer is achieved is called the $R_0$ ($R_{zero}$). The $R_0$ for Cy3 and Cy5 is approximately 50 Angstroms; that is, when Cy3 and Cy5 molecules are separated by 50 Angstroms, 50% of energy will be transferred between donor and acceptor molecules. When a pair of fluorophores is closer than the $R_0$ for that pair, there will be greater than 50% energy transfer, which will be seen as an increase in fluorescence (also called a high-FRET state). When a pair of fluorophores is farther apart than the $R_0$ for that pair, there will be a reduction in energy transfer and fluorescence (also called a low-FRET state). By "approximating the $R_0$" it is meant that the distance between the donor and acceptor is within 5-10% of deviation from the R0. If FRET is centered at $R_0$, then small distance changes can be measured. For example, a 10% change in FRET (e.g. 0.4 or 0.6) corresponds to about a 5-10 Angstrom change in distance (given low anisotropy and free spinning of the fluorophore).

Given the above considerations for selecting labeling sites, and taking LeuT as an example of a membrane protein, suitable labeling sites in accordance with this disclosure include, for example, His 7 in the amino terminus, Arg 86 in IL1, Arg 185 in IL2, Lys 271 in IL3, Thr 515 at the cytoplasmic end of TM12, Lys 239 in EL3, and His 480 in EL6. Suitable pairs of labeling sites including pairs of sites on the intracellular side of the transporter, or pairs of sites on the extracellular surface of LeuT.

In specific embodiments, a pair of fluorophores are attached to a pair of cysteine substitutions introduced on the intracellular side of the transporter, e.g., a pair of cysteine substitutions at two of the sites: His 7 in the amino terminus, Arg 86 in IL1, Arg 185 in IL2, Lys 271 in IL3, and Thr 515 at the cytoplasmic end of TM12. In particular embodiments, the pair of cysteine substitutions is selected from the group consisting of H7C/R86C, H7C/T515C, R185C/K271C, R185C/T515C, R86C/K271C, and R86C/R185C. In other specific embodiments, a pair of fluorophores are attached to a pair of cysteine substitutions introduced on the extracellular surface of LeuT, e.g., K239C/H480C.

Additional sites in LeuT which may be suitable for labeling include, for example, amino acid residues 25, 29, 33, and 34 in TM1, amino acid residues 111 and 114 in TM3, amino acid residues 136-150 in EL2, amino acid residues 243, 246, 249 and 253 in TM6, amino acid residues 305, 307, 309, 311, 314, 315, 317, 320, 324, 325 and 333 in EL4, amino acid residues 397, 400, 404 and 405 in TM10, and amino acid residue 480 in EL6. Labeling at these sites has also revealed dynamic changes in LeuT.

Similar mutations can be made to human NSS proteins targeted for study. For example, the sequence of a human NSS protein can be aligned with the sequence of LeuT or another member of the family for which suitable labeling sites have been determined, can be used to identify the positions analogous to those in LeuT or the other family member that have been shown as suitable for labeling and smFRET analysis. Alternatively, the three dimensional structure of human NSS protein, if available, can be compared with the three dimensional structure of LeuT or another member of the family to identify the analogous amino acid positions suitable for labeling and smFRET analysis. Once the molecular model of the target cognate protein is available on this basis, molecular dynamics simulations can be performed with this model structure to identify yet other suitable labeling sites based on the same criteria, thus taking into consideration any subtle changes produced by the differences in sequence in structure between the template and the target.

In specific embodiments, a structure-based sequence alignment, which is generated taking into consideration of both sequence information and available structural information (e.g., three-dimensional structure), is used as the basis to identify sites analogous to those which have been identified in LeuT. For example, a structure-based sequence alignment of LeuT with NSS proteins hDAT (also referred to as SLC6A3), hNET (also referred to as SLC6A2), and rSERT (also referred to as SLC6A4) (FIG. 18) has been generated (see, e.g., Thijs Beuming et al., Molecular Pharmacology November 2006 vol. 70 no. 5 1630-1642) and provides information on structurally homologous regions and analogous sites which should be useful in practicing the methods of the invention in other NSS proteins. In this alignment, to illustrate, sites that are analogous to LeuT site H7 are the amino acids that align with it, i.e., site T72 in hDAT, T68 in hNET, and T81 in rSERT (each residue being directly below H7 in FIG. 18). As a practical matter, any residues within a few (e.g., 1, 2 or 3) amino acid positions of an identified labeling site in LeuT or its analogous counterpart may be useful for fluorophore labeling of the NSS protein. To further illustrate, any of hDAT residues 68-74, hNET residues 66-72, and rSERT residues 79-83, being within a few residues of the structurally homologous LeuT residue 7, may be appropriate to mutate for labeling studies. Other suitable sites analogous to other labeling sites in LeuT disclosed herein above can be determined based on the alignment in FIG. 18.

In addition to mutations introduced for purposes of labeling, other mutations can be introduced, including mutations which mimic those found in established diseases or disorders, or mutations which result in a loss of function or gain of function. In the case of LeuT, mutations in R5 or Y268 disrupt substrate binding and protein function, as does the Y335 mutation in the dopamine transporter (Kniazeff, J. et al., J. Biol. Chem. 283, 17691-17701 (2008)). Gain of function and loss of function in human NSS proteins has been implicated in a variety of neuroaffective disorders including Parkinson's disease, depression, psychiatric and personality disorders, anxiety, attention deficit/hyperactivity disorder, as well as in sympathetic nervous system and cardiovascular dysregulation.

The membrane protein is typically first solubilized in a membrane protein carrier such as a detergent, then purified, followed by labeling. Alternatively, the protein may be first labeled and then loaded into a membrane protein carrier. A membrane protein carrier is a carrier for a membrane protein, which may be reagents used in membrane protein purification as defined hereinabove such as detergents and lipids, or structures composed of lipids and/or detergents (for example, in the form of liposome or micelle), or nanoparticles (such as NABBs and SMALPs) and nanodiscs. In a specific embodiment, micelles formed by DDM are used as a carrier. A cell is also considered a protein carrier. When a cell is used as a carrier, membrane proteins can be expressed in the cell with an extracellular tag, such as a SNAP tag, and then treated with with a dye to label; and intracellular proteins can be expressed in the cell as a fluorescent fusion protein or fused to a carrier, then can be labeled by employing a membrane permeant dye or injecting a reactive dye into the cell interior. Expression of a desired protein in a cell can be controlled by various know techniques, including through the use of inducible promoters and crippled kozak sequences.

The membrane protein, together with its carrier, is then immobilized to a solid plane or surface for single-molecule fluorescence studies. Suitable solid materials for use herein include glass, alginate beads or matrix, among others. The protein itself may be immobilized or attached to the solid surface, or alternatively, the vehicle carrying the protein may be attached to the solid surface (hence the protein being indirectly immobilized). A cell may be immobilized onto a glass surface, such as a glass slide, that has been treated with a substance (for example, fibronectin) that facilitates attachment and immobilization of the cell to the glass surface.

It has been determined by the inventors that spontaneous dissociation of the membrane protein from the image plane can virtually be eliminated by immobilizing the membrane protein or its carrier through strong affinity interactions such as a biotin-streptavidin interaction, which attributes at least in part to an extended imaging time scale for smFRET studies disclosed herein. Another strong affinity interaction is Biotin-Tris-NTA, where the Tris-NTA moiety binds to a His6 epitope in the membrane protein.

A biotin-streptavidin interaction can be created by passivating the solid surface with streptavidin, and incorporating biotin into lipids used in reconstitution or onto the membrane protein. Biotin can be incorporated into the membrane protein using a noncovalent linkage such as biotin-NTA interacting with a His epitope tag on the protein, or can be incorporated covalently either through addition of a biotin acceptor sequence and treatment with biotin ligase or by direct chemical modification with biotin through cysteine or lysine directed reactions. In a specific embodiment, a 15-amino-acid biotinylation domain GLNDIFEAQKIE-WHE (SEQ ID NO:1) (Beckett, D. et al., Protein Sci. 8, 921-929 (1999)) is introduced, e.g., to the N-terminus or C-terminus of a membrane protein under investigation.

The density of surface immobilization can be controlled through dilution and using a prism-based, wide-field configuration, to permit simultaneously imaging of low-density arrays of specifically tethered, individual membrane protein molecules. When a cell is used as a vehicle, density of protein expression on or in the cell is controlled by limiting protein expression via, for example, inducible promoters.

After the labeled membrane protein is immobilized, directly or indirectly, to a solid surface, imaging is performed under conditions, e.g., the illumination intensity of the laser, the exposure time, among other parameters, that support extended imaging time scale. By "extended imaging time scale" it is meant a period of time sufficient to capture and observe multiple or preferably all conformations of the membrane protein and transitions between different conformations. In some embodiments, an extended imaging time covers at least the dwell time of a specific conformation, and in particular embodiments, at least the sum of the dwell times (or excited-state lifetimes) of multiple or all conformations. Given that proteins differ in their conformational kinetics (some slow while other fast), the imaging time period needed to capture multiple conformations vary depending on the protein, and can be a period from 2-3 seconds up to at least a minute or over several minutes. Conditions that support extended imaging time scales include reducing the laser illumination intensity to minimize the photobleaching, and increasing the exposure time to maintain signal-to-noise ratios adequate to detect FRET changes at a reduced laser intensity. Fluorophores with extended lifetimes are also important to extended imaging times. In addition, inclusion of oxygen scavenging methods and protective agents such as TSQs in solution, particularly a TSQ such as Cyclooctatetraene, Trolox and/or NBA, is highly desirable.

Given the benefit of an extended observation period, it has been demonstrated herein that individual LeuT-H7C/R86C molecules undergo multiple transitions between the high- and low-FRET configurations in the absence of $Na^+$. With the reduced illumination intensity, the low-FRET state showed short-lived photophysical 'blinking' events that would have been masked under intense illumination by rapid, Cy3-mediated photoresurrection. Taking this into consideration, the average dwell time in high ($\tau \approx 18$ s) and low ($\tau \approx 25$ s) FRET states can be determined, indicating that a full opening-closing cycle of LeuT requires ~60 s.

From the imaging experiments, fluorescence data are acquired over time, which can include, for example, any of fluorescence intensity from one or more fluorphores, FRET traces determined from instantaneous fluorescence intensities of the donor and the acceptor fluorophores, the number of fluorophore blinking events for each FRET trace, and/or the occurrence of photobleaching event.

The collected data can be analyzed to determine the number of different conformations present (based on different FRET states observed, for example), the distribution among different conformations under a given condition, the dwell time for each conformation, and the transition time from one conformation to another. That is, the collected fluorescence data, acquired over an extended period of time, permits identification and quantification of changes in the amount of time that the protein molecule spends in its various conformational states, hence referred to herein as dynamic fluorescent studies. By measuring time-dependent conformational dynamics in a biomolecule, insights into the physical parameters of motion are obtained that relate to regulation and function.

The dynamic single-molecule fluorescence approach disclosed herein reveal useful information about the interaction of membrane proteins and ligands. The methods described herein can be used to test candidate compounds for effects on the conformation dynamics of a membrane protein.

Accordingly, in another aspect, the disclosure is directed to a method of screening for compounds that affect the activity of a membrane protein based on assessing the effects of a test compound on the conformational dynamics of the protein using the single-molecule fluorescence approach disclosed herein. The identified compounds are useful for treatment of diseases and conditions associated with the activity or otherwise malfunction of the membrane protein.

For example, dynamic smFRET studies can be conducted on a membrane protein as described herein, in the presence and in the absence of a test compound, respectively. FRET data can be collected and compared to determine whether the test compound changes the conformational dynamics of the membrane protein, e.g., a change in the FRET values, in the dwell time for one or more conformations, in the transition time from one conformation to another, or a change in the distribution among different conformations. A change observed indicates that the test compound affects the conformational dynamics of the protein, which can be correlated with effects on the activity of the membrane protein. For example, a specific conformation can be determined in smFRET studies to be associated with a particular activity of the membrane protein (such as ligand binding or gate opening). For instance, in the cases of H7C/R86C LeuT, the high FRET state represents an inward-closed conformation, and a low FRET state represents an inward-open conformation which creates space for leucine to be released to the cytoplasm. Therefore, an increase in the relative population of the specific conformation associated with a particular activity of the membrane protein, as a result of the presence of a test compound, indicates that this test compound likely enhances the indicated activity. A decrease in the relative population of the specific conformation associated with a particular activity of the membrane protein, as a result of the presence of a test compound, indicates that this test compound likely reduces the indicated activity. This type of study can also be performed to test competitive binding of multiple compounds. For instance, in the presence of Na+ and the LeuT substrate alanine, LeuT intracellular conformation switches rapidly between open and closed states, consistent with substrate transport activity. This can be seen in FRET studies as increased frequency of transition between high and low FRET states. However, the LeuT inhibitor CMI, which binds the S2/alanine binding site, inhibits these conformational dynamics, which stabilizes conformation of LeuT in a open/high FRET state (Example 2). Thus, CMI competes with alanine for binding to the S2 site. In a similar way, compounds can be screened for competitive effects on conformational dynamics of a membrane protein.

In another example, a change in the absolute FRET value(s) of a specific FRET state or conformation, as a result of the presence of a test compound, may indicate that the test compound may have changed certain structural elements for that specific conformation (e.g., the gate is wider, therefore the distance of the two fluorophores is greater), which can also be correlated with effects on the activity of the membrane protein. As an example, in LeuT, opening of the intracellular gate is required for substrate release into the cytoplasm. Thus, a compound, like the LeuT inhibitor CMI, that reduces formation of the lower-FRET state assigned to an open intracellular gate conformation, would be characterized as a LeuT inhibitor. Similarly, if the extracellular gate must be open (or outward facing) to bind ligand in the extracellular space, then a compound that prevents the formation of this state would be an inhibitor of the protein.

The dynamic single-molecule fluorescence approach disclosed herein can also be applied to compare a target protein with a variant form of the target protein. For example, a bacterial protein and its human homolog can be analyzed and compared in the presence or absence of drugs for purposes of identifying new antibiotics. Proteins encoded by different human alleles can also be studied and compared for the purpose of developing drugs that target specific populations. Additionally, drug sensitive and drug resistant forms of a target protein can also be studied and compared.

In a further aspect, this disclosure provides mutant membrane proteins which contains one or more mutations for affixing one or more fluorophores. Mutant proteins which contain additional mutation or mutations, introduced for purposes other than fluorophore attachment, are also disclosed herein. Such mutations can result in a loss of function or gain of function, or mimic those found in established diseases or disorders, can also be used in dynamic single-molecule fluorescence studies.

Reagents or compositions containing a mutant membrane protein described herein, either alone or loaded into a carrier, are also embodiments of the disclosure.

EXAMPLES

The present description is further illustrated by the following examples, which should not be construed as limiting in any way. The contents of all cited references (including literature references, issued patents, published patent applications as cited throughout this application) are hereby expressly incorporated by reference. These examples could be readily adapted to testing drugs and other therapies.

Example 1

Fluorescence Studies with Membrane Proteins.

LeuT mutants were expressed in *Escherichia coli*, purified, and labeled on targeted engineered cysteines with Cy3 and Cy5 maleimide. The inventors determined the functional properties of the labeled constructs by measuring leucine binding using a scintillation proximity assay, and measured alanine transport after reconstitution of the protein into proteoliposomes. The inventors studied the fluorescence properties of labeled proteins to establish specific and efficient labeling and to confirm that the observed FRET changes probably arise from inter-dye distance rather than photophysical phenomena. The inventors created various constructs, each with two cysteine residues strategically placed for labeling. Purified, labeled protein was immobilized onto a passivated-glass surface with a streptavidin-biotin linkage.

The inventors acquired fluorescence data using a prism-based TIR microscope. The inventors calculated FRET efficiency and analysed fluorescence and FRET traces using automated analysis software as described in U.S. application No. 61/437,203, which is herein incorporated by reference in its entirety. The inventors analyzed the single-molecule traces for LeuT in the presence and absence of the substrates $Na^+$ and Leu, upon addition of the transport inhibitors clomipramine and octylglucoside, and in response to mutations of the extracellular vestibule and the network of intracellular residues that is proposed to stabilize the inward closed state. The inventors carried out molecular dynamics simulations of the protein immersed in an explicit membrane and solvated with water molecules, ions and ligands, and ran long equilibrations (>500 ns) to assess conformational changes.

Preparation of Labeling Sites

The inventors removed an existing BamHI restriction site from the PET16b plasmid by silent modification (ACG to ACA) at position 135. The inventors used the Stratagene Quikchange mutagenesis kit to mutate the stop codon (TGA) to GGA. The inventors then introduced the biotin Acceptor Peptide (AP) sequence GLNDIFEAQKIEWHE (SEQ ID NO:1) (Beckett, D. et al., Protein Sci. 8, 921-929 (1999)) and a stop codon (TGA) using XhoI and BamHI restriction sites and primers AP-F (TCGAGGGGCTTAATGATATCTTTGAAGCTCAGAA-AATTGAATGGCATGAGTGAG) (SEQ ID NO:2) and AP-R (GATCCTCACTCATGCCATTCAATTTTCTGAGCTTC-AAAGATAT CATTAAGCCCC) (SEQ ID NO:3).

The inventors co-transformed pBirAcm (AVIDITY LLC) and AP-tagged PET16b into *E. coli* C41 (DE3). At OD600=0.5, The inventors added 10 mM D-biotin, induced expression with 0.3 mM IPTG, and grew cells overnight at 20° C.

The inventors performed site-directed replacement of single residues by cysteine using the Stratagene Quikchange mutagenesis kit. To confirm the fidelity of all plasmids, the inventors used DNA sequencing (Agencourt Bioscience Corporation).

Site-directed replacement of single residues by cysteine was performed using the Stratagene (La Jolla, Calif.) Quikchange™ mutagenesis kit. The fidelity of all plasmids was confirmed by DNA sequencing (Agencourt Bioscience Corporation).

Creation of biotin acceptor peptide tagged PETO18G-AP: An existing BamHI restriction site was removed from the PETO18G-AP plasmid through silent modification (ACG to ACA) at amino acid position 135. The stop codon (TGA) was mutated to GGA using the Stratagene (La Jolla, Calif.) Quikchange™ mutagenesis kit. The biotin Acceptor Peptide (AP) sequence GLNDIFEAQKIEWHE (SEQ ID NO:1) and a stop codon (TGA) was then introduced using XhoI and BamHI restriction sites using primers AP-F (TCGAGGGGCTTAATGATATCTTTGAAGCTCAGAA-AATTGAATGGCATGAGTGAG) (SEQ ID NO:2) and AP-R (GATCCTCACTCATGCCATTCAATTTTCTGAGCTT-CAAAGATAT CATTAAGCCCC) (SEQ ID NO:3).

Biotinylated protein expression: pBirAcm (AVIDITY LLC) and AP tagged PETO18G-AP were co-transformed into *E. coli* C41 (DE3). At OD600=0.5, 0.05 mM D-biotin was added, expression was induced with 0.3 mM IPTG, and cells were grown overnight at 20° C.

Protein Expression and Purification of LeuT Via Affinity Chromatography

Wild-type and mutant LeuT were produced in *E. coli* C41(DE3) harbouring pQO18 or pET16b and purified by immobilized metal (Ni2+) affinity chromatography using a Ni2+ Sepharose 6 FastFlow column (GE Healthcare). The inventors prepared membrane vesicles and purified LeuT variants as described (Quick, M. et al., Proc. Natl Acad. Sci. USA 104, 3603-3608 (2007)). For Cy3 or Cy5 labeled protein, after the protein was immobilized on the Ni2+ Sepharose 6 FastFlow resin, the resin was washed with 5 column volumes of Buffer A: 50 mM Tris/Mes (pH 7.5), 150 mM NaCl, 1 mM TCEP, 20% Glycerol, 0.05% w/v (1 mM) n-dodecyl-β-d-maltopyranoside (DDM), and 50 mM imidazole. The inventors then washed the resin with 5 column volumes of labeling buffer: 50 mM Mes (pH 6.0), 400 mM NaCl, 200 µM lysine, 50 µM TCEP, 1 mM DDM. After the resin was resuspended in labeling buffer, 200 µM Cy3 and 200 µM Cy5 maleimide (GE Healthcare) were added to the solution and reacted for 1 h at 4° C. while rotating the column. To remove free Cy3 and Cy5, the inventors reloaded the resin into the column and washed it with 5 column volumes of buffer A. The protein was eluted in Buffer A with 300 mM imidazole and purified with HPLC-mediated size-exclusion chromatography (Shodex Protein-KW803 column) in Buffer B: 50 mM Tris/Mes (pH 7.5), 150 mM NaCl, 1 mM TCEP, 1 mM DDM.

The inventors estimated the extent of the labeling from absorption spectra of labeled protein by measuring peak maxima at 552 nm and 650 nm for Cy3 and Cy5, respectively, using a Hitachi model 24 UV-VIS scanning spectrophotometer. The inventors determined protein concentration using the amido black method (Schaffner, W. et al., Anal. Biochem. 56, 502-514 (1973)). Under the same conditions, control labeling experiments of wild-type LeuT, which is devoid of cysteine, resulted in no significant incorporation of Cy3 or Cy5 dyes. Final samples were flash frozen and stored at −80° C. before use.

Protein Expression and Purification of Zap1 Via Affinity Chromatography

Zap1 protein expression: PET28-Zap1-TEV (PET28-Zap1 vector was from Thomas P. Sakmar. A PreScission cleavage site was replaced by TEV cutting site) was transformed to BL21 (DE3). One clone was picked from the plate and cultured in 10 ml LB containing 50 ug/ml kanamycin overnight at 37° C. Then transferred to 1 L LB containing Kanamycin, At OD600=0.5, 1 mM IPTG was added. After culturing for 3-4 hours at 37° C., cells were centrifuged at 7500 g for 10 min and the pellet was frozen at −80° C. until you are free to purify the protein. Cells from 1 L culturing were resuspend in 18 ml 20 mM KPi, pH 7.5, 1 mM PMSF. After Adding 0.2 g Triton X-100, cells were Sonicated in icy water until cells were broken and then centrifuged at 30,000 g for 30 min. The supernatant was incubated with Ni-sepharose 6B for 1 h and loaded into column. Then the column was washed with 4 volume of Buffer A (40 mM Tris/Mes, pH8.0, 0.3 M NaCl, 1% Triton X-100), 4 volume of Buffer B (40 mM Tris/Mes, pH8.0, 0.3 M NaCl, 50 mM Cholate), 4 volume of Buffer C (40 mM Tris/Mes, pH8.0, 0.3 M NaCl) and 4 volume of Buffer D (40 mM Tris/Mes, pH8.0, 0.3 M NaCl, 50 mM Imidazole). Then the protein was eluted by buffer E (40 mM Tris/Mes, pH8.0, 0.3 M NaCl, 0.3 M Imidazole) and Dialysed with Buffer F (10 mM Tris/Mes, pH7.4, 0.1 M NaCl) overnight. In order to remove the His Tag from Zap 1, purified Zap1 protein was diluted with 50 mM tris/Mes, pH7.5, 100 mM NaCl, 1 mM DTT, 0.5 mM EDTA to 0.5 mg/ml. Then purified TEV protease was added by 1:20 (mol:mol) to Zap1 protein and incubated for 2 hours at room temperature. Then TEV treated Zap1 protein was dialyzed in cold room overnight with 50 mM Tris/Mes, pH7.5, 100 mM NaCl. The remaining His tag Zap1 protein was removed by Ni-sepharose 6B column.

Protein Expression and Purification Via NABB

NABB particle preparation: *E. coli* total lipids (around 1 ml 20 mg/ml; Avanti polar lipids Inc) were dried by argon and vacuum for 3 h. Then 1 ml buffer containing 0.5% DDM, 100 mM NaCl, 50 mM Tris/Mes, pH7.5 was added and vortexed until soluble and filtered through 0.22 uM Membrane. If particle will be immobilized by botin-lipids, 1% Biotin-Cap-PE (Avanti polar lipids Inc) will be added to the *E. coli* total lipids. Zap1:LeuT:lipids (2:1:75 mol:mol:mol) were mixed and DDM concentration was kept at 0.5%. After rotating at 4° C. for 30 min, the mixture (usually around 200 µl) was loaded to 1 ml Extracti-Gel D slurry (PIERCE). Extracti-Gel D slurry was equilibrated by 150 mM Tris/Mes, pH 7.5) and detergent was removed by adding three to four aliquots of 0.2 mL of detergent free buffer on top and collecting the eluate in equal volumes.

Liposome Preparation

Prepare liposome for single molecule recording: lipids were prepared as in NABB particle preparation (10 mg/ml. liposome will be extruded through 0.1 µm membrane and the size will be around 0.1 µm. By calculation, 10 mg/ml lipids will form liposome around 100 nM). Lipids were diluted with 0.1 M KPi, pH 6.5 to 5 mg/ml with 0.2% (W/V) DDM and then LeuT was added to final concentration 10 nm. This ration will have around 80% liposomes empty without protein on it. Bio-Beads at 60 mg/ml was added and rotated for 1 hour at room temperature two times. After adding the third time of Bio-Beads, the mixture was transferred to cold room and rotated overnight. The supernatant was centrifuged at 323 kg for 45 min. Then re-suspend the pellet in 0.1 M KPi, pH 7.5 and frozen in liquid nitrogen. Before using, thaw the liposome and extrude through 0.1 µM membrane to control the liposome size.

Protein Immobilization:

Microfluidic imaging chambers passivated with a mixture of PEG and biotin-PEG were incubated with 0.8 µM streptavidin (Invitrogen) followed by 20 nM biotin-NTA (Biotium) charged with NiCl2. Cy3/Cy5-labeled His10-LeuT molecules (2 nM) were surface immobilized to surface-bound Ni2+. No significant surface immobilization was observed in the absence of streptavidin. This method can be used to immobilize protein with His Tag in detergent or in nanodisc.

If protein is biotinylated or the nanodisc/liposomes contain Biotin lipids, either can be immobilized to the surface directly after streptavidin incubation.

Scintillation Proximity-Based Binding Studies

The inventors bound $^3$H-leucine (140 Ci mmol-1; Moravek) to purified LeuT-variants using the scintillation proximity assay (SPA) as described (Shi, L. et al., Mol. Cell 30, 667-677 (2008); Quick, M. et al., Proc. Natl. Acad. Sci. USA 104, 3603-3608 (2007)) with 25 ng of purified protein per assay in buffer composed of 50 mM Tris, Mes (pH 8.0), 100 mM NaCl, 1 mM TCEP, 20% glycerol and 1 mM DDM.

Transport and Binding in Proteoliposomes

The inventors prepared liposomes using *E. coli* polar lipid extract and phosphatidylcholine (Avanti) at a 3:1 (w/w) ratio, as described (Shi, L. et al., Mol. Cell 30, 667-677 (2008)). The inventors reconstituted purified LeuT variants at a 1:150 (w/w) ratio in preformed, Triton X-100-destabilized liposomes. The inventors measured the accumulation of 3H-Ala at 23° C. in assay buffer comprising 50 mM Tris/Mes (pH 8.5) and 50 mM NaCl. The inventors assessed binding of 3H-Ala to LeuT proteoliposomes by dissipating the electrochemical NaCl gradient with 25 µg ml-1 gramicidin for 5 min before the start of the reaction. Uptake reactions were stopped by quenching the samples with ice-cold assay buffer followed by rapid filtration through GF/F filters (Advantec MFS).

Steady-State Fluorescence Anisotropy Measurements

The inventors carried out steady-state anisotropy measurements of Cy3-labeled LeuT (10 nM) using a PT1 spectrofluorometer with excitation and emission wavelengths of 532 nm and 560 nm, respectively.

Calculation of Distances from FRET Efficiencies

The inventors estimated distances between Cy3 and Cy5 in specific FRET states using the following equation:

$$R = R_0 \sqrt[6]{\frac{1-E}{E}},$$

where $R_0$ is the distance at which 50% energy transfer is observed. The experimentally determined $R_0$ of 58.4 Å was estimated according to the equation (Lakowicz, J. R. 3rd edn (Springer, 2006)):

$$R_0 = 0.221 \sqrt[6]{\Phi_D \kappa^2 \eta^{-4} J(\lambda)},$$

where the refractive index of the experimental solution ($\eta$) was estimated to be 1.4 and the orientation factor, $\kappa^2$, was assumed to be $\frac{2}{3}$ given isotropic rotation on the millisecond timescale. The spectral overlap integral $J(\lambda)=8.5 \times 1^{-13}$ M$^{-1}$ cm$^{-3}$ was calculated using the normalized fluorescence emission spectrum of Cy3-7C-LeuT and the absorption spectrum of Cy5-7C-LeuT collected using bulk fluorescence instrumentation (Photon Technologies). The Cy3 and Cy5 extinction coefficients used in calculation (Mujumdar, R. B. et al., Bioconjug. Chem. 4, 105-111 (1993)) were:

$$\varepsilon_{550(Cy3)} = 150,000 \text{ M}^{-1} \text{ cm}^{-1}$$

and $$\varepsilon_{650(Cy5)} = 250,000 \text{ M}^{-1} \text{ cm}^{-1}.$$

The donor quantum yield of Cy3-7C-LeuT ($\Phi_{Cy3}=0.23$) was estimated using the comparative method (Williams, A. et al., Analyst (Lond.) 108, 1067-1071 (1983)) using Rhodamine 101 in ethanol as a standard ($\Phi_{R101} \approx 1.0$) (Karstens, T. et al., J. Phys. Chem. 84, 1871-1872 (1980)). The inventors collected the fluorescence emission spectra of both dyes with excitation at 520 nm using constant illumination intensity and slit widths. The inventors calculated the Cy3 quantum yield as follows:

$$\Phi_{Cy3} = \Phi_{Rh101} * \left(\frac{F_{Cy3}}{F_{R101}}\right) * \left(\frac{A_{R101}}{A_{Cy3}}\right) * \left(\frac{\eta_{Cy3}}{\eta_{Rh101}}\right)^2,$$

where $F_{Cy3}$ and $F_{R101}$ are the integrated fluorescence emission spectra; $A_{Cy3}$ and $A_{R101}$ are the absorbances; and $\eta_{Cy3}=1.4$ and $\eta_{R101}=1.36$ are the refractive indices of the solutions used for Cy3-LeuT (the buffer used for single-molecule experiments) and Rhodamine 101 (ethanol), respectively.

Single-Molecule FRET Experiments

The inventors acquired fluorescence data using a prism-based TIR microscope, as described (Munro, J. B. et al., Mol. Cell 25, 505-517 (2007)). All experiments were performed in buffer containing 50 mM Tris/MES (pH 7.5), 10% glycerol, 0.02% w/v DDM, 5 mM 2-mercaptoethanol and 200 mM salt (KCl or NaCl, as specified). The inventors used an oxygen scavenging environment (1 unit per µl glucose oxidase, 8 units per µl catalase, 0.1% v/v glucose) containing 1 mM cyclooctatetraene in all experiments to minimize photobleaching (Dave, R. et al., Biophys. J. 96, 2371-2381 (2009)).

The inventors incubated microfluidic imaging chambers passivated with a mixture of PEG and biotin-PEG (Blanchard, S. C. et al. Proc. Natl Acad. Sci. USA 101, 12893-12898 (2004)) with 0.8 µM streptavidin (Invitrogen), followed by 20 nM biotin-NTA (Biotium) charged with NiCl2. Cy3/Cy5-labeled His10-LeuT molecules (2 nM) were surface-immobilized to surface-bound Ni2+. The inventors observed no significant surface immobilization, measured as described below, in the absence of biotin-NTA.

Cy3 fluorophores were excited by the evanescent wave generated by TIR of a single-frequency light source (Ventus 532 nm, Laser Quanta). Photons emitted from Cy3 and Cy5 were collected using a 1.2 NA 60× water-immersion objective (Nikon), and optical treatments were used to spatially separate Cy3 and Cy5 frequencies onto a cooled, back-thinned CCD (Cascade 128, Photometrics). The inventors acquired fluorescence data using MetaMorph software (Universal Imaging Corporation). The inventors corrected spectral bleed-through of Cy3 intensity on the acceptor channel by subtracting 7.5% of donor signal from the acceptor. FRET traces were calculated as: $FRET=I_{Cy5}/(I_{Cy3}+I_{Cy5})$, where $I_{Cy3}$ and $I_{Cy5}$ are the instantaneous Cy3 and Cy5 fluorescence intensities, respectively. Using an established procedure (Roy, et al., Nature Methods 5: 507-516 (2008)), The inventors estimated the ratio of donor and acceptor quantum yields and detection efficiencies ($\gamma$) to be close to 1; therefore, no correction was applied.

Analysis of smFRET Traces

The inventors analyzed fluorescence and FRET traces using automated analysis, in which traces were selected using algorithms implemented in MATLAB (MathWorks). Algorithms for analyzing smFRET data are found in U.S. 61/437,203, which is herein incorporated by reference in its entirety. Properties were calculated for each trace, and selected for further analysis if they met the following specific criteria: a single photobleaching event, at least 8:1 signal-to-background noise ratio (SNR), <4 donor fluorophore blinking events, a donor-to-acceptor Pearson's correlation coefficient <0.5, and a lifetime of at least 15 frames showing FRET ≥0.15. The inventors detected photobleaching events in each trace as a significant (≥3 standard deviations of background noise) drop in the median-filtered (window size of 9 frames) total fluorescence intensity ($I_{Total}=I_{Cy3}+I_{Cy5}$) without a return to the previous average level. Events in which fluorescence intensity did return were marked as blinking events. Signal-to-noise ratios were calculated as total intensity relative to the standard deviation of background noise: $I_{Total}/stdev(I_{Cy3})+stdev(I_{Cy5})$. The inventors excluded data points corresponding to donor fluorophore dark states from calculation of the correlation coefficient.

To simplify the presentation of FRET histograms, The inventors removed zero-FRET states following idealization of the data to a two-state model (E=0.1±0.1 and E=0.4±0.1) using a segmental k-means algorithm (Qin, F., Biophys. J. 86, 1488-1501 (2004)). Error bars in FRET histograms represent the standard deviation of 100 bootstrap samples of each set of FRET traces examined.

The inventors estimated kinetic parameters for biotinylated H7C-R86C-LeuT samples by manually selecting traces showing at least one transition between clearly distinct states with anti-correlated changes in donor and acceptor fluorescence intensity in each transition. The data were then idealized using a three-state model (E=0±0.1, E=0.49±0.09, and E=0.75±0.07) with FRET parameters estimated by fitting smFRET histograms obtained in the absence of Na+ to Gaussian functions. Initial rates were set to 0.05 s$^{-1}$, as estimated from visual inspection of FRET traces. The inventors estimated average dwell times in each FRET state using a maximum likelihood algorithm (Qin, F. et al., Biophys. J. 70, 264-280 (1996)).

The inventors initially performed smFRET experiments on N-terminally His-tagged, Cy3/Cy5-labeled LeuT in 0.03% DDM, surface immobilized through a biotin-NTA interaction in passivated, streptavidin-coated microfluidic chambers (Munro, J. B. et al., Mol. Cell 25, 505-517 (2007); Roy, et al., Nature Methods 5: 507-516 (2008)) (FIG. 1). By controlling the density of surface immobilization through dilution and using a prism-based, wide-field configuration, the inventors could simultaneously image low-density arrays of specifically tethered, individual LeuT molecules.

In these experiments the inventors used micelles formed by DDM as vehicles. One can also use NABBs, SMALPs, liposomes, cells, or other vehicles known in the art.

The inventors used biotin-NTA to immobilize the molecule on which the inventors were conducting smFRET studies. Other immobilization techniques known in the art can be used, and the protein itself may be immobilized, or the vehicle carrying the protein may be immobilized.

The inventors achieved oxygen scavenging and triplet state quenching conditions for optimal fluorophore performance (low photophysical noise and reduced photobleaching) through screening (Dave, R. et al., Biophys. J. 96, 2371-2381 (2009)). Initial measurements of H7C/R86C- and H7C/T515C-labeled LeuT molecules, performed at 40 ms time resolution and high signal-to-noise ratio (~18:1 on average), showed that both systems, in the presence of 200 mM K+ and the nominal absence of Na+, displayed two readily distinguished FRET states (~0.51 and ~0.75; ~0.43 and ~0.73, respectively; FIG. 1B-D and FIG. 4). These observations indicated that there might be two distinct LeuT conformations in the population, differing by ~13 Å in the distance between each fluorophore pair (FIG. 9; note that the short-lived, zero-FRET state sampling events correspond to transient excursions of the Cy5 fluorophore to non-fluorescent dark states).

Figure 4:
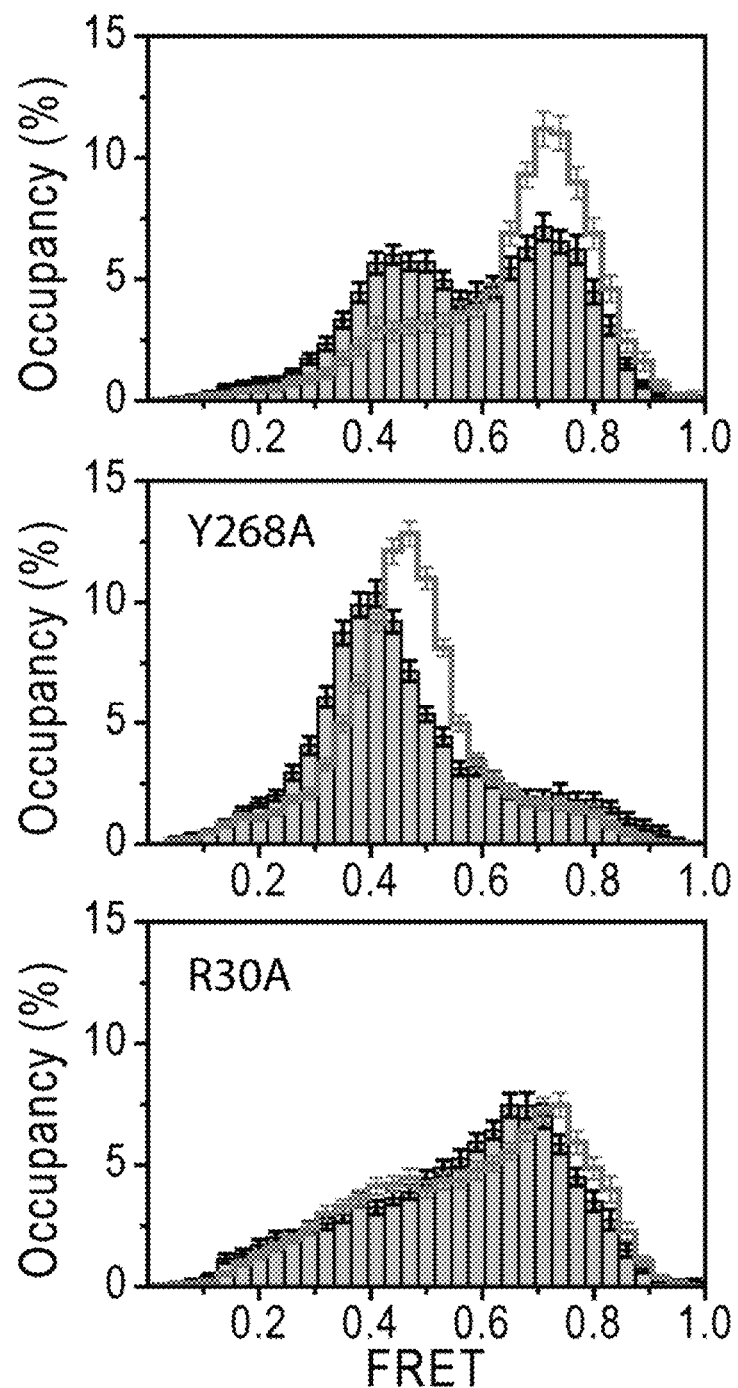
FIG. 4: smFRET imaging experiments performed with intracellularly labeled LeuT-H7C-T515C in wild-type, the Y268A "intracellular gate" mutant, and the R30A "extracellular gate" mutant. Experiments were performed in the absence of Na+ (200 mM KCl) (bars) or in its presence (200 mM NaCl) (line).

Consistent with the half-maximum effective concentration ($EC_{50}$) of Na+ for stimulating binding and transport (~10 mM) (Shi, L. et al., Mol. Cell 30, 667-677 (2008)), and a ligand-dependent transition between these states, the relative populations of low- and high-FRET LeuT conformations depended on Na+ concentration. Addition of saturating Na+ concentrations (200 mM) stabilized higher-FRET states in both systems (~0.77 and ~0.73, for H7C/R86C and H7C/T515C, respectively: FIG. 1, FIG. 4 and FIG. 9), consistent with substrate-bound LeuT crystal structures, in which the intracellular end of the transporter is compact (Yamashita, A. et al., Nature 437, 215-223 (2005); Singh, S. K. et al., Channels (Austin) 2 (5) (2008)). High-FRET state occupancy was saturated at 200 mM Na+. Under such conditions, the inventors did not observe further changes in FRET upon addition of 20 µM leucine (FIG. 1 and FIG. 9). However, at 5 mM Na+, where both low- and high-FRET states remain populated, leucine binding redistributed the two populations in a concentration-dependent fashion in favour of higher-FRET configurations (FIGS. 1E, F). The same results were obtained whether LeuT molecules were immobilized by the N terminus or the carboxyl terminus.

These findings are consistent with spontaneous, ligand-modulated rearrangements in specific elements of LeuT near the intracellular gating region. In the absence of ligands, a low-FRET state would be achieved by an outward and/or downward movement of position 7 (at the N terminus of TM1) with respect to positions 86 (IL1) and 515 (cytoplasmic end of TM12). Correspondingly, a high-FRET state could be achieved spontaneously or upon ligand binding by a reciprocal motion of TM1 with respect to IL1 and TM12, leading to an inward-closed LeuT conformation. By contrast, the inventors observed no substrate-dependent changes for any of the other constructs labeled on the intracellular face of the protein, indicating that these positions do not move substantially during intracellular gating.

The site of labeling at position 7 is adjacent to the highly conserved Trp 8 residue, which is involved in a conserved interaction network among a residue triad that includes Ile 187 (IL2) and Tyr 268 (IL3) at the intracellular face (Kniazeff, J. et al., J. Biol. Chem. 283, 17691-17701 (2008)). Tyr 268 also forms cation-π and ionic interactions with residues Arg 5 (at the N terminus) and Asp 369 (TM8), thereby bringing together NT, IL2 and IL3 and closing the transport pathway at the intracellular surface of LeuT. Mutation of the homologous interaction network in the structurally related dopamine transporter and GABA transporter has been inferred to promote inward-open conformations (Kniazeff, J. et al., J. Biol. Chem. 283, 17691-17701 (2008); Bennett, E. R. et al., J. Biol. Chem. 275, 34106-34113 (2000)).

Figure 2:
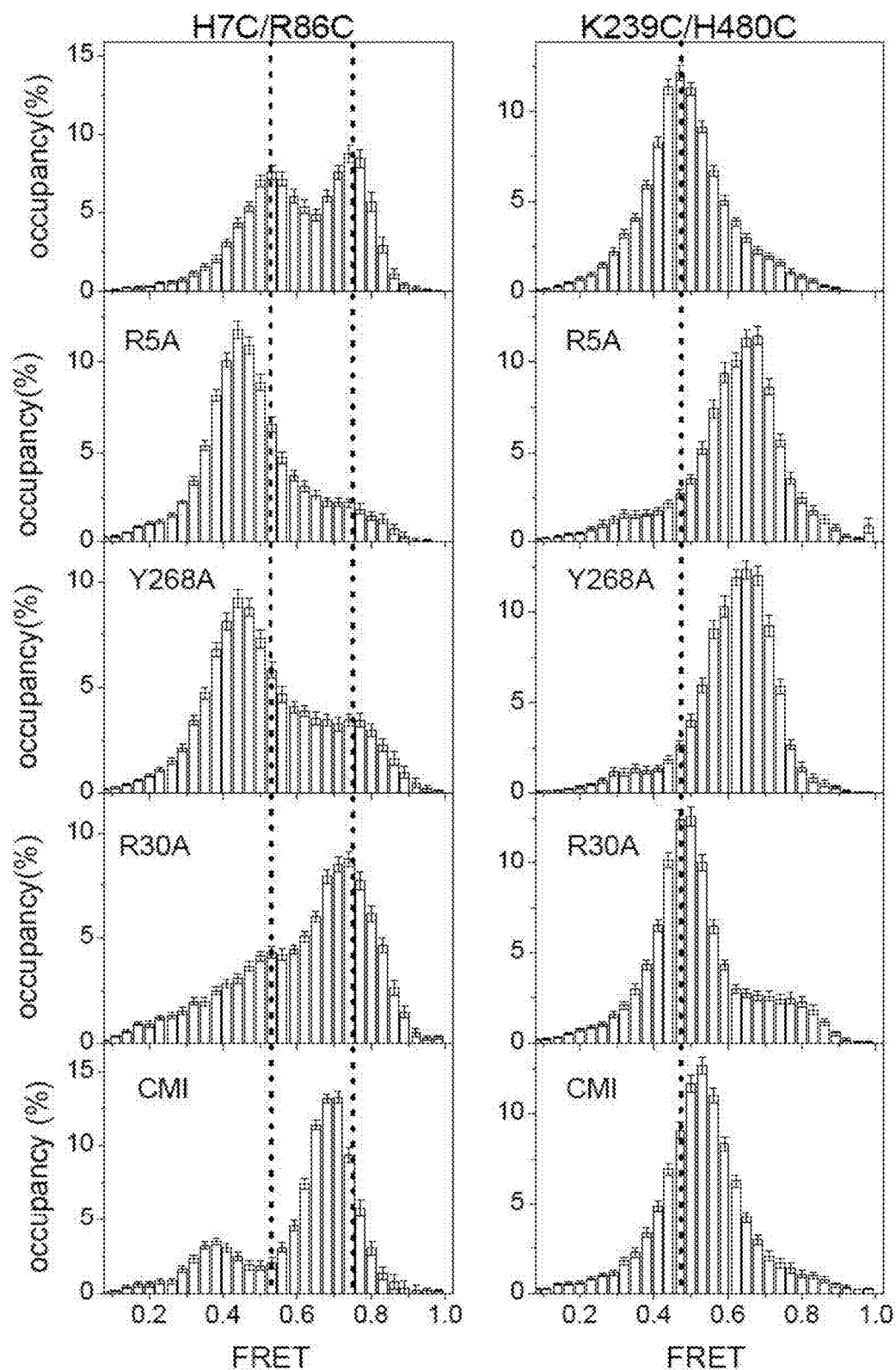
FIG. 2: Effects of mutation and CMI on FRET histograms of LeuT-H7C/R86C and LeuT-239C/480C. FRET histograms from single-molecule traces obtained in the presence of 200 mM KCl for LeuT-H7C/R86C (left) and LeuT-239C/H480C (right) are shown in the context of the mutations R5A, Y268A or R30A, or the presence of 0.5 mM CMI. For clarity, fluorophore dark states have been computationally removed from all histograms (see Examples).

To investigate further how the interaction network at the intracellular end of LeuT contributes to the inward-open conformation, the inventors performed smFRET experiments on H7C/R86C-labeled LeuT constructs in the background of the disruptive mutations R5A or Y268A (Kniazeff, J. et al., J. Biol. Chem. 283, 17691-17701 (2008)). As anticipated, the inventors found lower-FRET states for both mutant constructs in the absence of $Na^+$ (FIG. 2). In both cases, the absolute values of the low-FRET states (~0.43 and ~0.44, respectively) were significantly lower than observed for the wild-type background (~0.51; FIG. 9). These observations indicate that the low-FRET state visited in the wild-type background in the absence of $Na^+$ might represent a time-averaged population of low-FRET configurations that change in the context of the R5A and Y268A mutations.

Both mutations also affected the FRET distributions observed for extracellularly labeled LeuT (K239C/H480C), indicating that the 'inward opening' effects of these mutations are coordinated with 'outside closing'. The inventors also observed allosteric effects in response to the mutation of Arg 30, which lines the S2 site (Shi, L. et al., Mol. Cell 30, 667-677 (2008)) and participates in the formation of cation-π interactions within a proposed extracellular 'gating region' (Yamashita, A. et al., Nature 437, 215-223 (2005)). In the R30A mutant, H7C/R86C-labeled LeuT adopted a high-FRET configuration in the absence of $Na^+$ (~0.70), whereas the distance between extracellular pairs (K239C/H480C) was unchanged (FIG. 2 and FIG. 9). These data, corroborated by evidence from the H7C/T515C construct (FIG. 4), show that mutations in putative intracellular and extracellular gate regions lead to long-range effects on the conformation of LeuT. However, that the R30A mutation affected the conformation of the intracellular network, while leaving the extracellular probes largely unchanged, indicates that the transmission of signal throughout the molecule involves a cascade of flexible interactions and local conformations rather than a single rigid body rearrangement (Shi, L. et al., Mol. Cell 30, 667-677 (2008); Kniazeff, J. et al., J. Biol. Chem. 283, 17691-17701 (2008); Lockless, S. W. et al., Science 286, 295-299 (1999)).

Also consistent with an allosterically mediated modulation of the interaction network in the intracellular side, the TCA inhibitor clomipramine (CMI) stabilized a high-FRET state (~0.69) in wild-type H7C/R86C-labeled LeuT (FIG. 2). This FRET value, which is distinct from that observed in the absence of CMI (~0.75), was unchanged in the presence of $Na^+$ (FIG. 9), consistent with the molecular dynamics simulations of LeuT (>100 ns trajectory) with either CMI or OG in the S2 site (and leucine in the S1 site) (Quick, M. et al., Proc. Natl Acad. Sci. USA 106, 5563-5568 (2009)). These experiments showed that the intracellular network adopted similar and slightly more open configurations when CMI or OG was present in the S2 site, around 30 Å away from residue 7 at the intracellular end of TM1. On the extracellular side, CMI increased FRET between K239C/H480C-labels (from ~0.49 to ~0.53; FIG. 4), consistent with a modest compaction of this region of LeuT when inhibitor was bound.

smFRET dynamic study. To investigate directly whether the conformational changes associated with intracellular gating could be tracked in individual LeuT molecules, the inventors carried out smFRET experiments under conditions that supported extended imaging. First, the inventors reduced the laser illumination intensity to minimize the photobleaching that had previously limited the observation window (~3 s). Second, the inventors increased the exposure time fourfold to 160 ms to maintain signal-to-noise ratios adequate to detect FRET changes at reduced laser intensity. Finally, to eliminate the spontaneous dissociation of LeuT from the image plane that resulted from the relatively low-affinity His-NTA interaction ($k_{off}$>0.25 $min^{-1}$), the inventors introduced a 15-amino-acid C-terminal biotinylation domain (Beckett, D. et al., Protein Sci. 8, 921-929 (1999)) into the LeuT (H7C/R86) construct to allow immobilization by a biotin-streptavidin linkage that is much less prone to dissociation ($k_{off}$<0.25 $h^{-1}$; data not shown).

Figures 3A, 3B, 3C, 3D, 3E, 3F, 3G, 3H, 3I, 3J, 3K, 3L:
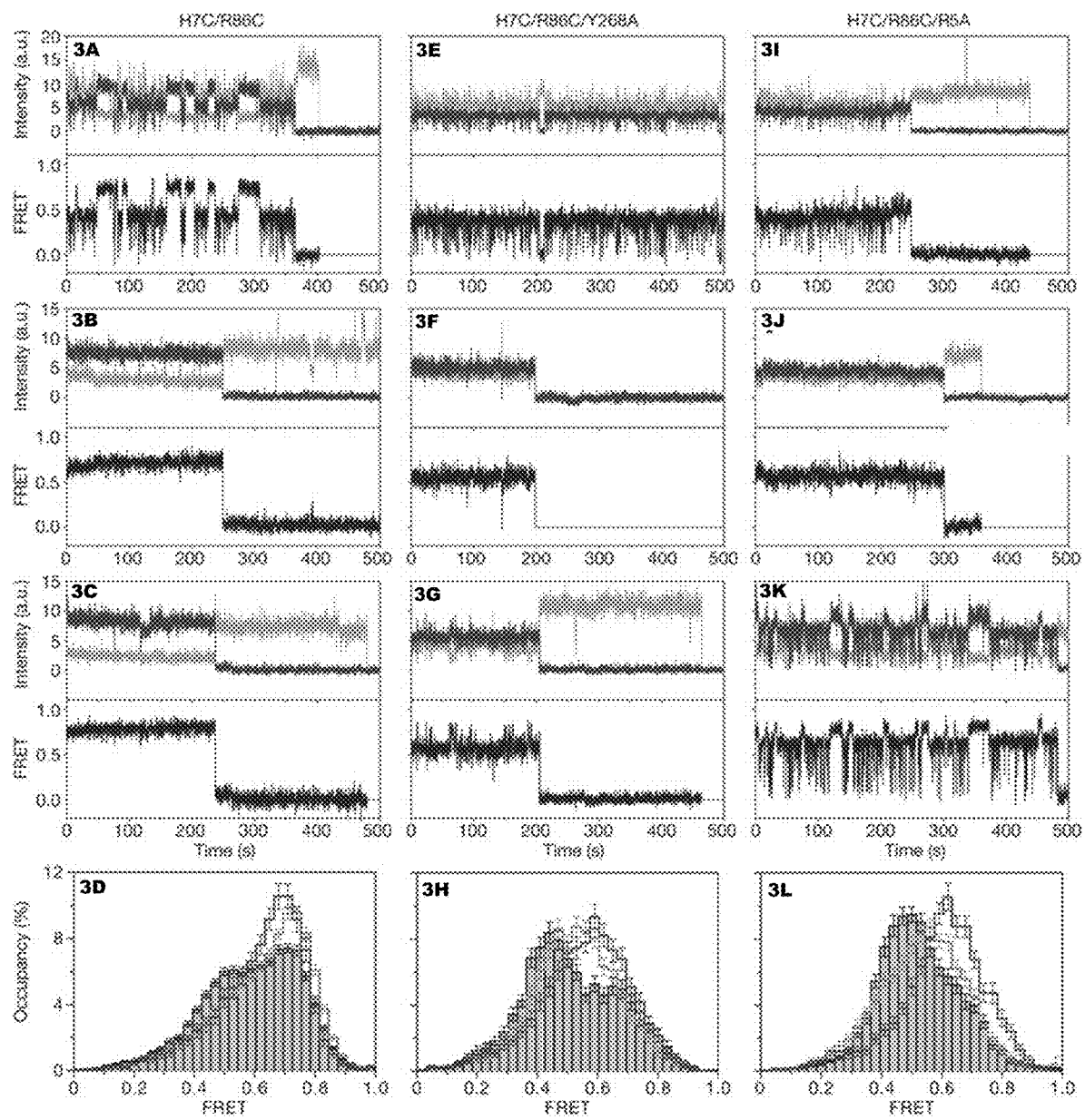
FIG. 3A-3L: Long single-molecule trajectories reveal FRET transitions. Representative single-molecule traces from 160-ms images are shown for LeuT-H7C/R86C (left), LeuT-H7C/R86C/Y268A (centre), and LeuT-H7C/R86C/R5A (right) in 200 mM KCl (A, E, I), 200 mM NaCl (B, F, J) or 200 mM NaCl and 20 μM leucine (C, G, K). Cy3 (donor) and cy5 (acceptor) fluorescence are shown in green and red, respectively. FRET efficiency is shown in blue. One-dimensional histograms (D, H, L) represent the population data obtained in the presence of 200 mM KCl (grey bars), 200 mM NaCl (blue line), or 200 mM NaCl and 20 μM leucine (red line).

Given the benefit of an extended observation period, the inventors could show that individual LeuT-H7C/R86C molecules undergo multiple transitions between the high- and low-FRET configurations in the absence of $Na^+$ (FIG. 3A), consistent with the direct detection of isomerization of the intracellular network. With the reduced illumination intensity, the low-FRET state showed short-lived photophysical 'blinking' events that were probably masked under intense illumination by rapid, Cy3-mediated photoresurrection (Dave, R. et al., Biophys. J. 96, 2371-2381 (2009)). Taking this into consideration, the inventors could estimate the average dwell time in high ($\tau \approx 18$ s) and low ($\tau \approx 25$ s) FRET states, indicating that a full opening-closing cycle required ~60 s. As anticipated from the results of shorter experiments, the high FRET state was highly stabilized in the presence of high $Na^+$ concentrations (>76 s, limited by photobleaching; FIGS. 3B, C).

The inventors could also assess the unique behaviour of R5A and Y268A LeuT mutants in greater detail under long time-scale imaging conditions. In the absence of $Na^+$, LeuT-Y268A mainly showed a single, broadened low-FRET state (FIG. 3E). Transitions to higher-FRET states were rare, both with and without substrates. However, consistent with $Na^+$ binding and partial/incomplete gate closure, the lower-FRET state value increased in the presence of saturating $Na^+$ and Leu (FIGS. 3F, G). In light of the markedly impaired transport activity of LeuT-Y268A (FIG. 7), these data point towards a potential correlation between the ability to achieve a properly closed intracellular interaction network and the efficiency of transport. They also support our previous suggestion that the Y335A dopamine transporter (homologous to LeuT Y268A) has low transport activity because it adopts an inward-open conformation (Kniazeff, J. et al., J. Biol. Chem. 283, 17691-17701 (2008)). Note that in this mutant, zinc, which is thought to help the transporter reach an outward-facing conformation, markedly enhances transport (Kniazeff, J. et al., J. Biol. Chem. 283, 17691-17701 (2008)), presumably by facilitating inward closure.

Figure 7:
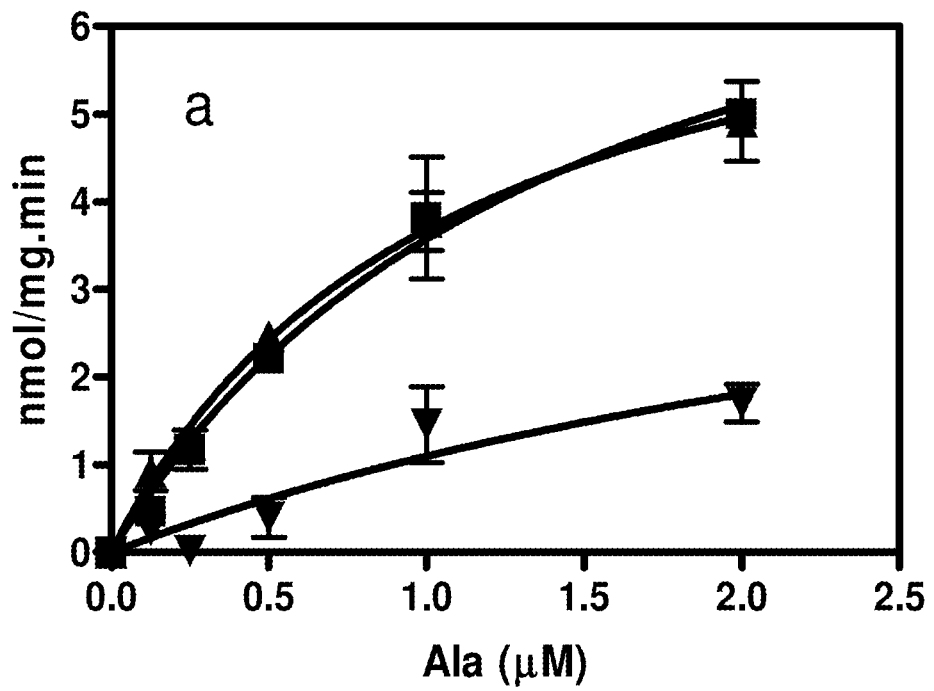
FIG. 7: Activity of intracellular gate mutants. (a) Ala transport and (b) Leu binding activities were measured in wild-type (squares ■), R5A (triangles ▲) and Y268A (inverted triangles ▼) LeuT. Error bars represent the standard deviation from three independent experiments.
Figure 7:
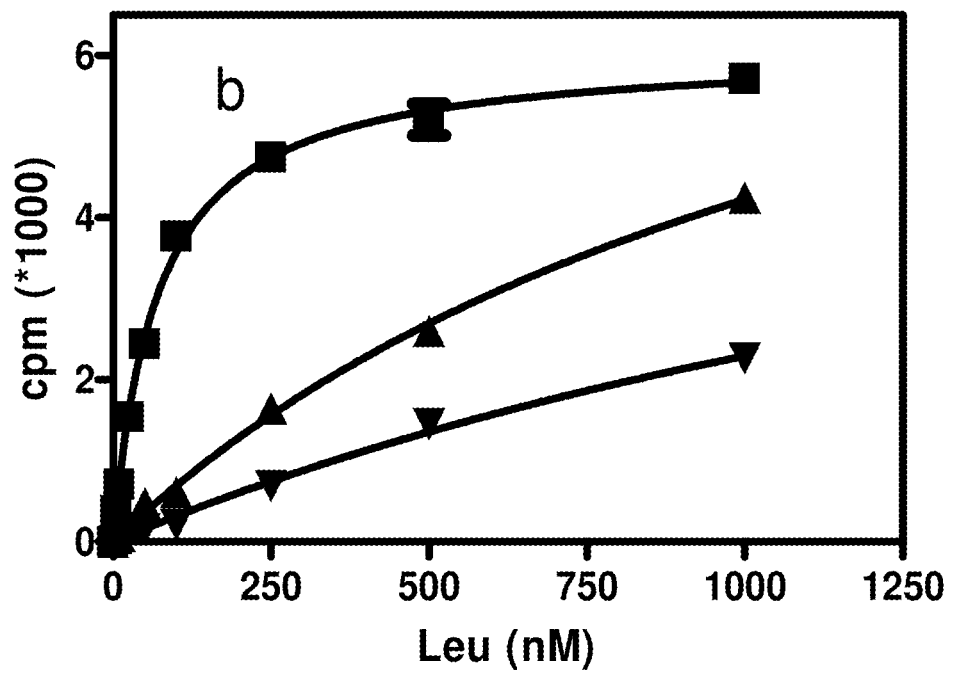

LeuT-R5A showed transient, leucine-dependent isomerization to high-FRET configurations for the 7/86 pair (~0.77), consistent with an inward closed conformation (compare FIGS. 3I, K) and with the finding that its transport activity is much less impaired than that of Y268A (FIG. 7). As for LeuT-Y268A, Na$^+$ alone only shifted the low-FRET state value up slightly. With both substrates present, the lower-FRET state dwell time was similar to that of the wild-type background ($\tau\approx28$ s), whereas the lifetime of the high-FRET state was substantially reduced compared to the wild-type background ($\tau\approx8$ s versus $\tau\approx18$ s, respectively).

Molecular Dynamics

The inventors carried out simulations on the system prepared as described (Shi, L. et al., Mol. Cell 30, 667-677 (2008)). Briefly, it consisted of more than 77,000 atoms, including the explicit membrane model, solvating water molecules, and the various ions and ligands. Each of the simulations was started from the end of the previously described SMD trajectory in which the ligand in the S1 site was pulled towards the intracellular side and had reached 8-10 Å below the S1 binding site (Shi, L. et al., Mol. Cell 30, 667-677 (2008)). The molecular dynamics simulations were carried out with the NAMD program under constant temperature (310 K) and constant pressure (1 atm) (NPT) conditions. The equilibrations were long (150 ns), to achieve a suitable relaxation of the system. The inventors carried out two independent runs for the system, for consistency and convergence check. The results of one run are compared with those of a control run (Shi, L. et al., Mol. Cell 30, 667-677 (2008)) starting from the crystal structure (PDB: 2A65, in an inward-closed state), to illustrate the level of stability and fluctuation of the system under the simulation conditions.

Figures 5A, 5B:
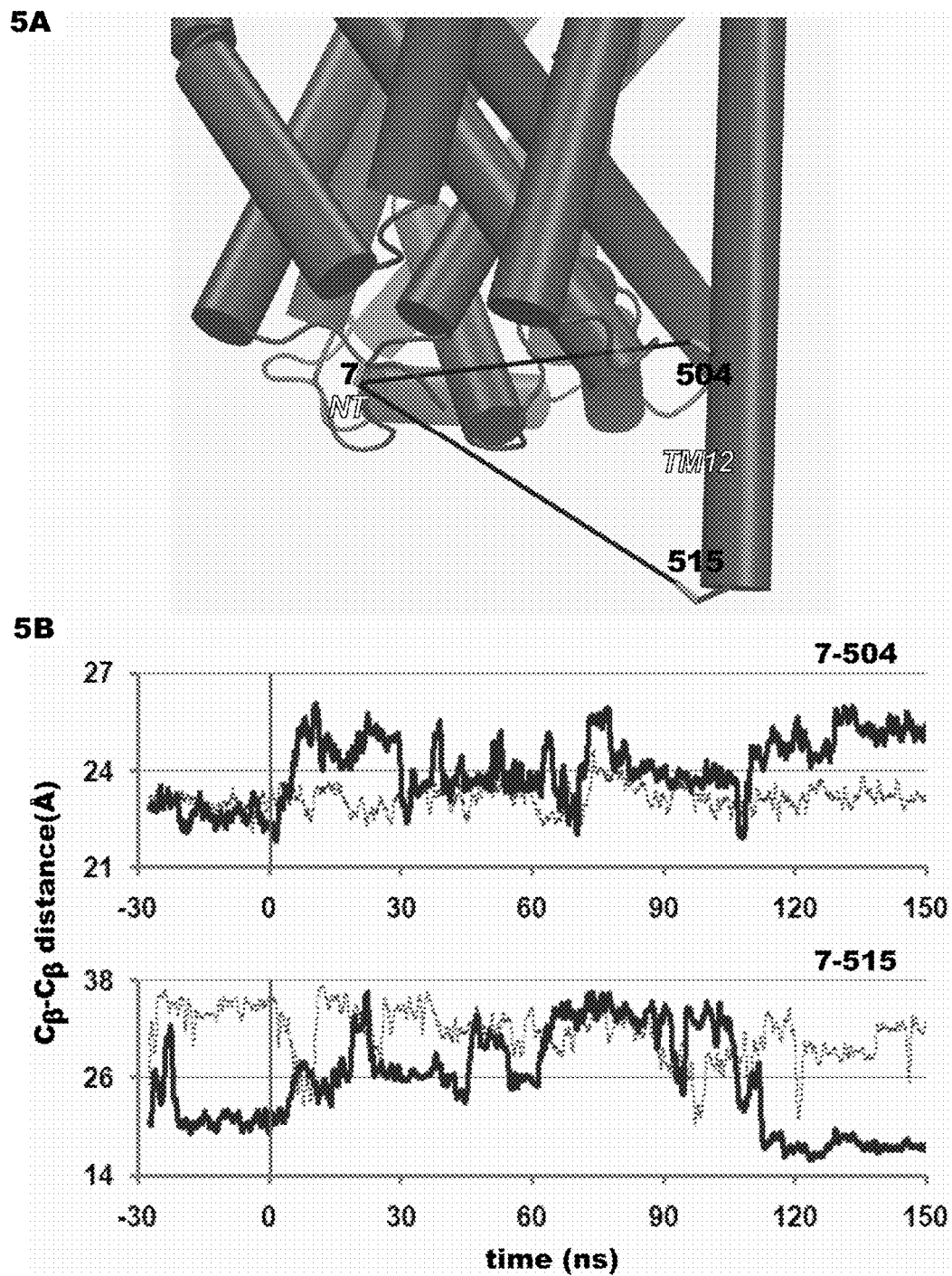
FIG. 5A-5B: Molecular dynamics data for the 7-515 and 7-504 pairs of residues. Since 515 is located at the distal end of TM12, relatively far below the membrane boundary, in the aqueous environment (panel A), the C-terminal segment in which it resides exhibits high flexibility, much greater than that expected in the smFRET experiment where this terminus is anchored and embedded in the surrounding detergent. Thus, the MD data for the 7/515 pair exhibit relatively large fluctuations that exaggerate the actual motions observed experimentally (panel B). However, the relevant motion of TM12 relative to NT-TM1 is reliably described by the distance between 7 and position 504, which is located near the membrane boundary. The 7/504 distance changes during the MD simulation shown in panel b demonstrate a gradual evolution towards a stable increased distance, consistent with the corresponding experimental measurements.
Figure 6:
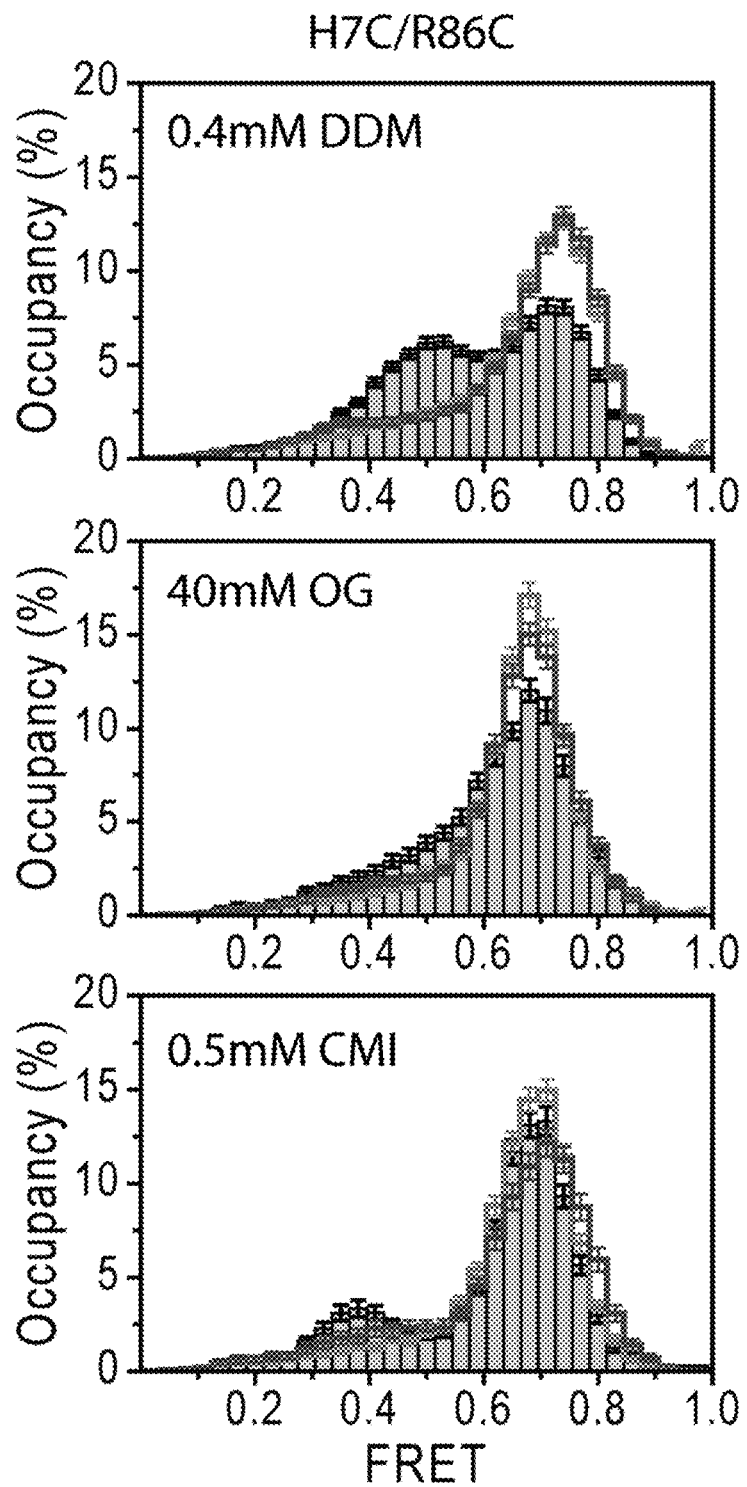
FIG. 6: Effect of detergents on the intracellular conformation and ligand sensitivity of LeuT. Dye-labeled LeuT-H7C/R86C was imaged in the presence of 0.4 mM DDM or after exchanging with buffer containing n-octyl-β-D-glucoside (OG) or with 0.5 mM CMI in 0.4 mM DDM. Experiments were performed in the absence of Na+ (black bars), in 200 mM NaCl (blue lines), or in the presence of 200 mM NaCl and 20 μM Leu (red lines).

To interpret the distance changes identified with smFRET with respect to changes occurring in the intracellular interaction network during the transition from an outward-open to an inward-open conformation, and to investigate how they might pertain to the transport mechanism, the inventors performed molecular dynamics simulations. Inward-open conformations of LeuT generated by computationally 'pulling' the S1 site-bound substrate intracellularly in the presence of S2 and the absence of Na$^2$ (Shi, L. et al., Mol. Cell 30, 667-677 (2008)) were subjected to prolonged MD simulations (two parallel runs of 150 ns each), designed to examine the structural equilibration of LeuT after the simulated substrate transport event. During the extended equilibration period, the inventors observed dissociation of the Trp 8-Ile 187-Tyr 268 interaction network. This resulted in a relative downward and outward movement of TM1 and the region containing the residue at position 7, and a corresponding increase in the distance between positions 7 and 86 and position 7 and the intracellular end of TM12 (FIG. 5). This rearrangement was associated with significant conformational changes in the IL2-TM5 region (including Ile 187), facilitated by changes in the bend angle of the highly conserved proline kink in TM5. By contrast, the distance between residues 86 and 185 was largely unchanged throughout the simulation as the bottom of TM4 maintained a relatively stable position.

The inventors therefore found that the conformational rearrangements in LeuT observed during the simulated transport event leading to the inward-open conformation agreed well with the estimated changes in distance deduced from the smFRET data. A recent analysis of crystal structures sharing a LeuT-like fold prompted Gouaux and colleagues to propose that coordinated rearrangements of TM1a and TM1b are associated with conformational transitions in the protein (Shaffer, P. L. et al., Science 325, 1010-1014 (2009)). Both the simulation and the smFRET data are consistent with a movement of TM1a and illuminate the function-related dynamic elements in these putative rearrangements. Importantly, an outward movement of TM1a is essential to create space for leucine to be released to the cytoplasm. Notably, a parallel molecular dynamics study of a structure homology-based molecular model of the human transporter for dopamine, DAT, produced very similar results (Shan, J, et al, PLoS ONE 6, e16350 (2011)).

Photophysical Transitions to Zero-FRET in 160 ms FRET Trajectories.

The smFRET traces obtained during low-power illumination of dye-labeled H7C/R86C-LeuT undergo frequent, transient zero-FRET state excursions, often referred to as photophysical "blinking" events (FIG. 3). Such events, frequently observed during single-molecule fluorescence imaging, typically result from the intersystem crossing of the acceptor fluorophore (Cy5) to non-fluorescent dark states (Dave, R. et al., Biophys. J. 96, 2371-2381 (2009)). Blinking events are characterized by having a strong laser power dependence on the observed rates entering and exiting dark states. Although the triplet state quenching strategies employed greatly reduce the lifetimes of these states, under low-power illumination the rate of return to the fluorescing state approaches the imaging timescale (160 ms). Consequently, rapid transitions to low and zero FRET states were assigned as Cy5 dark states. In line with the statistical labeling strategy employed for the introduction of fluorophores into LeuT and the environmentally sensitive nature of dye photophysics (Dave, R. et al., Biophys. J. 96, 2371-2381 (2009)), blinking events of this nature were observed for only ~50% of the labeled molecules, predominantly from the lower-FRET ($\leq 0.6$) states. Several of the traces shown in FIG. 3 have this blinking behavior, which serves as additional evidence of conformational transitions between structurally distinct LeuT conformations.

Interpretation of Changes in FRET Efficiency.

Time-dependent fluctuations in FRET efficiency observed in experiments with LeuT labeled at position H7C+R86C and H7C+T515C are interpreted as principally reporting on changes in the distance between donor and acceptor dyes reflecting underlying changes in LeuT structure. For such a FRET-distance relationship to hold, one or both fluorophores must be freely rotating on the timescale of imaging ($\kappa^2=2/3$) and fluorophore quantum yield must remain relatively constant over the imaging period. Both $\kappa^2$ and quantum yield impinge on the FRET-distance relationship via the parameter $R_0$.

To test the possibility that the changes in FRET observed do not simply report on changes in quantum yield, fluorescence quantum yields of Cy3 and Cy5 at position 7 and 86 in LeuT were measured under conditions where FRET changes in LeuT are observed (e.g. +/–ligand as shown in (FIG. 1)). Consistent with the notion that quantum yield remains relatively constant under conditions where substantial changes in FRET were observed, changes in spectral shift were not observed and the fluorescence intensities of Cy3-labeled LeuT in the absence and presence of saturating ligand concentrations (200 mM) and/or Leu (20 µM) were indistinguishable within approximately 10% experimental error. Additionally, the measured fluorescence lifetimes of Cy3-7C-LeuT and Cy5-7C-LeuT samples were independent of ligand concentration.

To test whether the observed fluctuations in FRET efficiency result from changes in the extent of randomization of dye orientation during imaging, Cy3 anisotropy was measured at multiple sites of labeling (FIG. 8). The measured anisotropy values (r=~0.22), while indicative of somewhat restricted or slowed Cy3 motion when the dye is linked to LeuT, is consistent with substantial randomization of orientation on the imaging time scale (40-160 ms), particularly given the dye's relatively short fluorescence lifetime (<1.5 ns). Again, no systematic changes in anisotropy were observed in the absence and presence of Na$^+$ (200 mM) and/or Leu (20 µM).

Although changes in dye quantum yield and/or relative orientation could complicate the FRET-distance relationship interpretation, fluctuations in these parameters are anticipated to occur on the sub-millisecond timescale, substantially more rapid than the timescale of the FRET changes observed (tens of seconds). The likelihood that significant contributions to the measurement result from spurious changes in these parameters is reduced by the number of internally consistent data obtained when examining distinct pairs of labeling sites, ligand-binding and LeuT mutations distal to the site of labeling. Therefore, the evidence supports the interpretation that changes in FRET principally arise from changes in distance between the dyes resulting from changes in LeuT structure.

In summary, molecular dynamics and smFRET data indicate that a movement of TM1a is associated with intracellular gating in LeuT. This movement is regulated by substrate and inhibitor binding, by mutations of the intracellular network that stabilizes an inward-closed state, and by mutations of the S2 site, reflecting the allosteric nature of the transport mechanism. Whereas FRET-based single-molecule studies using confocal imaging have previously identified distinct conformational states in the H$^+$-coupled sugar transporter lactose permease (Majumdar, D. S. et al., Proc. Natl Acad. Sci. USA 104, 12640-12645 (2007); Nie, Y. et al., J. Mol. Biol. 379, 695-703 (2008)), the inventors have obtained minutes-long time-scale FRET trajectories that have directly revealed relatively slow conformational switching events in LeuT, which would be difficult or impossible to observe using other methods.

The extension of imaging times beyond the limit of freely-diffusing molecules using the total internal reflection (TIR) approach, in combination with the surface-immobilization and triplet state quenching strategies, provide a powerful new way to explore the structural and kinetic features of Na$^+$:substrate symport by LeuT. Extension of these single-molecule imaging approaches to other membrane proteins, as well as to LeuT reconstituted into proteoliposomes in which the inventors can control the Na$^+$ gradient, will provide further mechanistic details on how the energy stored in ion gradients can be used to drive uphill substrate accumulation by secondary active transporters.

Example 2

Substrate-Modulated Gating Dynamics in a NSS Homolog.

Protein Expression and Purification.

LeuT variants were expressed in *E. coli* C41(DE3) as described (Shi, L. et al., Mol. Cell 30, 667-677 (2008)). For functional studies LeuT variants were expressed from pQO18 or derivatives thereof carrying the indicated mutations (Quick, M. et al., Proc. Natl Acad. Sci. USA 106, 5563-5568 (2009)), whereas for single-molecule FRET studies biotin acceptor peptide-tagged LeuT variants were expressed in pETO18G and its derivatives (Zhao, Y. et al., Nature 465 (7295), 188 (2010)). Protein was purified by immobilized metal (Ni$^{2+}$) affinity chromatography using a Ni$^{2+}$ Sepharose 6 FastFlow column (GE Healthcare) (Zhao, Y. et al., Nature 465 (7295), 188 (2010)). For fluorescent labeling of LeuT, Cy3 maleimide and Cy5 maleimide (GE Healthcare) were added at an equimolar ratio for 1 hour while the protein was bound to the Ni$^{2+}$ resin. Free dye was removed prior to the elution of LeuT.

Scintillation proximity-based binding studies. Binding of $^3$H-leucine or $^3$H-alanine (146 Ci/mmol and 49.4 Ci/mmol, respectively; Moravek) to purified LeuT-variants was measured with the scintillation proximity assay (SPA) as described (Shi, L. et al., Mol. Cell 30, 667-677 (2008)) with 25 ng of purified protein per assay in buffer composed of 150 mM Tris/Mes, pH 7.5/50 mM NaCl/1 mM TCEP/0.1% n-dodecyl-β-D-maltopyranoside or 50 mM Tris/Mes, pH 7.5/150 mM LiCl/1 mM TCEP/0.1% n-dodecyl-β-D-maltopyranoside. To determine the molar ratio of Leu (or Ala)-to-LeuT binding samples were incubated with increasing concentrations of radioligand and measured in the SPA cpm mode of the MircoBeta™ counter (Perkin Elmer). The efficiency of detection was calculated with standard curves of known concentrations of $^3$H-Leu or $^3$H-Ala. The standard curves were used to transform cpm into the amount of bound substrate (Shi, L. et al., Mol. Cell 30, 667-677 (2008)). The amount of LeuT in the SPA assays was determined (Schaffner, W. et al., Anal. Biochem. 56, 502-514 (1973)). SPA-based binding studies using 2 µM [$^{22}$Na]Cl (1017 mCi/mg; Perkin Elmer) were performed in 200 Tris/Mes, pH 7.5/1 mM TCEP/0.1% n-dodecyl-β-D-maltopyranoside in the presence of 0-50 mM NaCl (equimolar replacement of Tris/Mes to obtain a total molarity of 200 mM) (Shi, L. et al., Mol. Cell 30, 667-677 (2008)). All experiments were repeated at least in duplicate with triplicate determination of all individual data points. Kinetic constants (shown±the SEM of the fit) were obtained by fitting the data of independent experiments to global fitting in Prism or SigmaPlot.

Single-molecule FRET imaging experiments. Fluorescence experiments were performed using a prism-based TIRF microscope as previously described (Zhao, Y. et al., Nature 465 (7295), 188 (2010); Munro, J. B. et al., Mol. Cell 25, 505-517 (2007)). Microfluidic imaging chambers were passivated with a mixture of PEG and biotin-PEG and incubated with 0.8 µM streptavidin (Invitrogen). Cy3/Cy5-labeled, biotinylated LeuT molecules were surface immobilized through biotin-streptavidin interaction. Cy3 fluorophores were excited by the evanescent wave generated by TIR of a single-frequency light source (Ventus 532, Laser Quanta). Photons emitted from Cy3 and Cy5 were collected using a 1.2 N.A. 60× water-immersion objective (Nikon) and optical treatments were used to separate Cy3 and Cy5 frequencies onto a cooled, back-thinned EMCCD camera (Cascade 512, Photometrics). Fluorescence data were acquired using Metamorph (Universal Imaging Corporation).

All experiments were performed in buffer containing 50 mM Tris/MES (pH 7.5), 10% glycerol, 0.02% w/v DDM, 5 mM 2-mercaptoethanol and 200 mM salt (KCl or NaCl, as specified). The inventors used an oxygen scavenging environment (1 unit per ml glucose oxidase, 8 units per ml catalase, 0.1% v/v glucose) containing 2 mM cyclooctatetraene in all experiments to minimize photobleaching.

Analysis of single-molecule fluorescence data was performed using custom software written in MATLAB (The MathWorks). A subset of the acquired traces were selected for further analysis using the following criteria: 1) single-step donor photobleaching, 2) signal-to-background noise ratio (SNR) ≥8, 3) <4 donor blinking events, 4) non-zero FRET efficiency for at least 60 seconds. Additional manual trace selection was performed to refine the data, where each selected trace was required to have: 1) no large fluctuations in total fluorescence intensity ($I_D+I_A$) and 2) at least one transition between clearly defined FRET states with anti-correlated transitions in donor/acceptor intensity or a single dwell in a clearly-defined FRET state. Kinetic analysis was performed to idealize FRET traces and calculate average dwell times using a three state model as previously described (Zhao, Y. et al., Nature 465 (7295), 188 (2010)). Error bars for transition rate estimates and FRET histograms were calculated as the standard deviation of 100 bootstrap samples of the traces. Error bars for state occupancies were calculated from 1,000 bootstrap samples of traces.

Experiments were performed on site-specifically labeled LeuT (H7C/R86C) engineered to contain a 15 amino acid, C-terminal biotinylation domain (Beckett, D. et al., Protein Sci. 8, 921-929 (1999)). Direct biotinylation of LeuT facilitated extended periods of surface immobilization and imaging within passivated, streptavidin-coated microfluidic chambers (Munro, J. B. et al., Mol. Cell 25, 505-517 (2007); Roy, et al., Nature Methods 5: 507-516 (2008)). Direct observations of conformational processes within the intracellular gate region of LeuT were made using a prism-based total internal reflection, wide field imaging strategy. As described in Example 1, LeuT displays two readily-distinguished FRET states (~0.51 and ~0.75) in the presence of 200 mM $K^+$ and the nominal absence of $Na^+$, consistent with the existence of two distinct conformations of the intracellular gate that differ by ~13 Å in the distance separating the fluorophore pair.

Figures 10A, 10B, 10C, 10D, 10E, 10F:
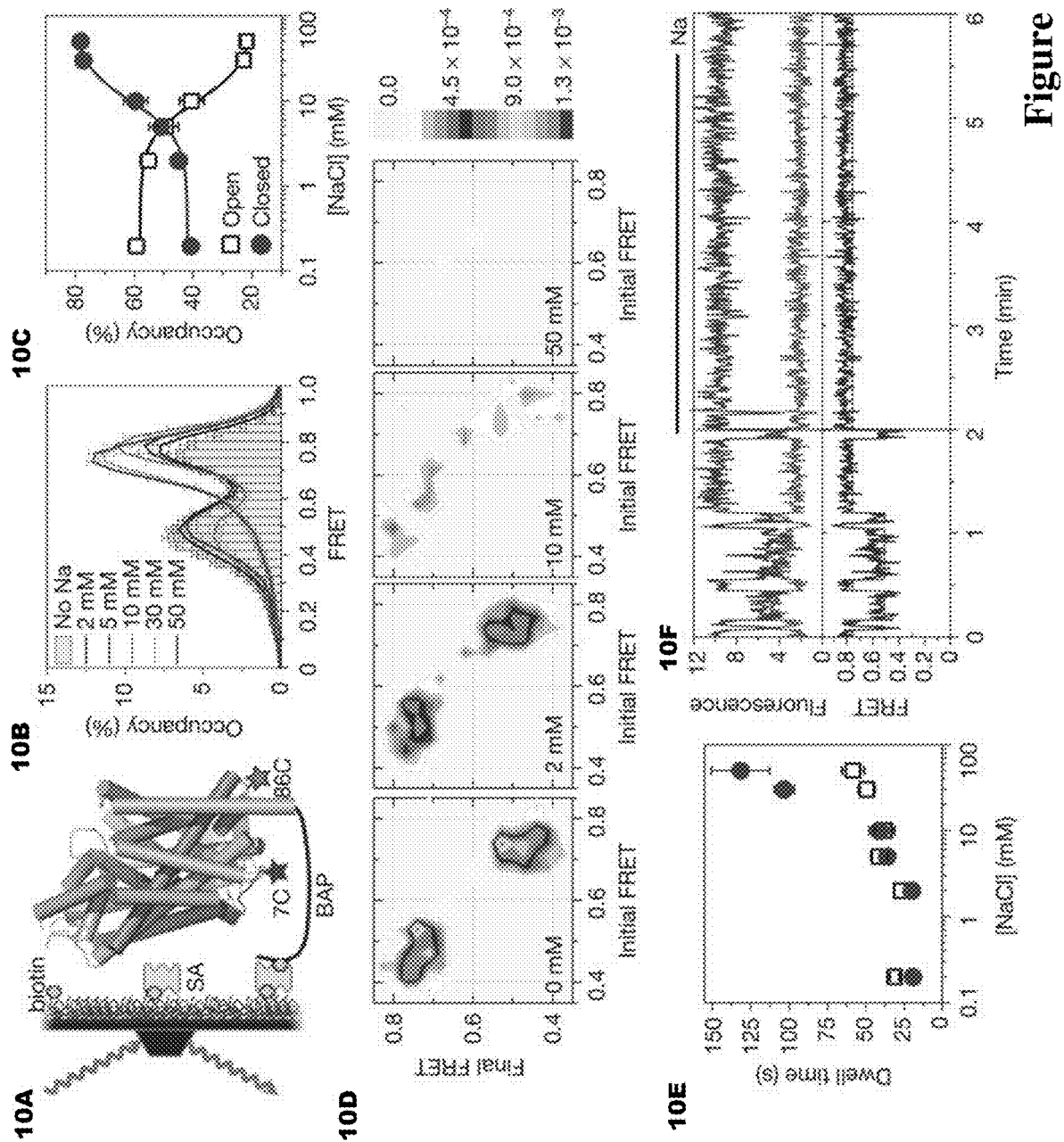

The application of hidden Markov modeling (HMM) methods to analyze the $Na^+$-dependent changes in FRET revealed that the distribution of low- and high-FRET LeuT conformations was altered by $Na^+$ with an $EC_{50}$ of 10.9 mM, consistent with the $EC_{50}$ for $Na^+$-dependent stimulation of substrate binding and transport (Shi, L. et al., Mol. Cell 30, 667-677 (2008)) (FIG. 10A-B). Kinetic analysis revealed that $Na^+$-induced changes in LeuT conformation resulted primarily from the preferential stabilization of the inward-closed state (by ~7-fold) (FIG. 10C), which decreased the frequency of observed transitions (FIG. 10d). Such effects were most clearly demonstrated by perfusing $Na^+$ during the direct imaging of individual LeuT molecules (FIG. 10E). Here, slow, spontaneous transitions between open and closed states, initially observed in 200 mM $K^+$ buffer, were dramatically decreased upon exchange into $Na^+$-containing buffer, leading to the preferential stabilization of the inward-closed state.

Figures 11A, 11B, 11C, 11D, 11E:
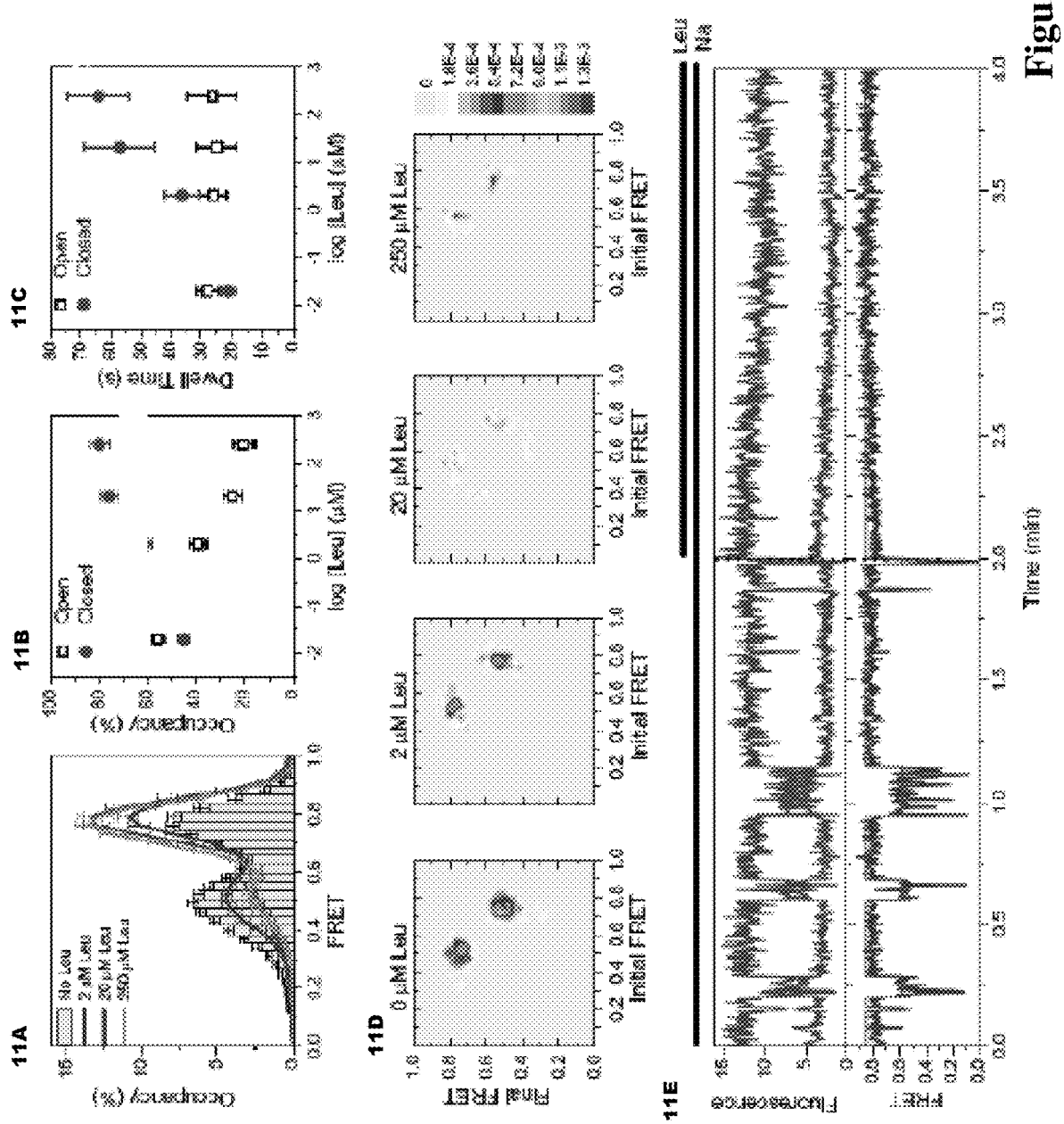

Reasoning that substrate-induced intracellular gating might be observed best under conditions more closely mimicking the cellular context in which intracellular $Na^+$ concentrations are relatively low, the inventors performed experiments at $Na^+$ concentrations sufficient for Leu binding but below the $EC_{50}$ of $Na^+$. However, even at 2 mM $Na^+$, Leu shifted the population toward the closed intracellular gate conformation (FIG. 11A-B) through a ~3.5-fold stabilization of this state (FIG. 11C), which resulted in a global decrease in transition frequency (FIG. 11D). These effects were recapitulated at the level of individual molecules when LeuT in the presence of 2 mM $Na^+$ was exchanged into Leu-containing buffer (FIG. 11E). Thus, while unambiguously demonstrating binding of both $Na^+$ and Leu to LeuT, these results corroborate our earlier finding that Leu binding has the net effect of diminishing the likelihood of intracellular gate opening. One possible explanation for these observations is that Leu's high affinity for the transporter (Shi, L. et al., Mol. Cell 30, 667-677 (2008)) makes it a poor substrate for transport, which in our measurements is manifested in the greatly extended lifetime of the closed state. To test this hypothesis, intracellular gate dynamics were quantitatively assessed in the presence of the more efficiently transported substrate Ala.

$^3$H-Ala Transport in Proteoliposomes.

Proteoliposomes were prepared as described (Shi, L. et al., Mol. Cell 30, 667-677 (2008)). The accumulation of $^3$H-Ala (49.4 Ci mmol$^{-1}$; Moravek) was measured at 23° C. in assay buffer comprised of 150/50 mM Tris/Mes (pH 8.5) and 50 mM NaCl/150 mM LiCl. The reaction was quenched by the addition of ice-cold assay buffer without radiotracer and the proteoliposomes were collected on GF75 glass fiber filters (Advantec) before the determination of the accumulated cpm by liquid scintillation counting.

Figures 12A, 12B, 12C, 12D, 12E, 12F:
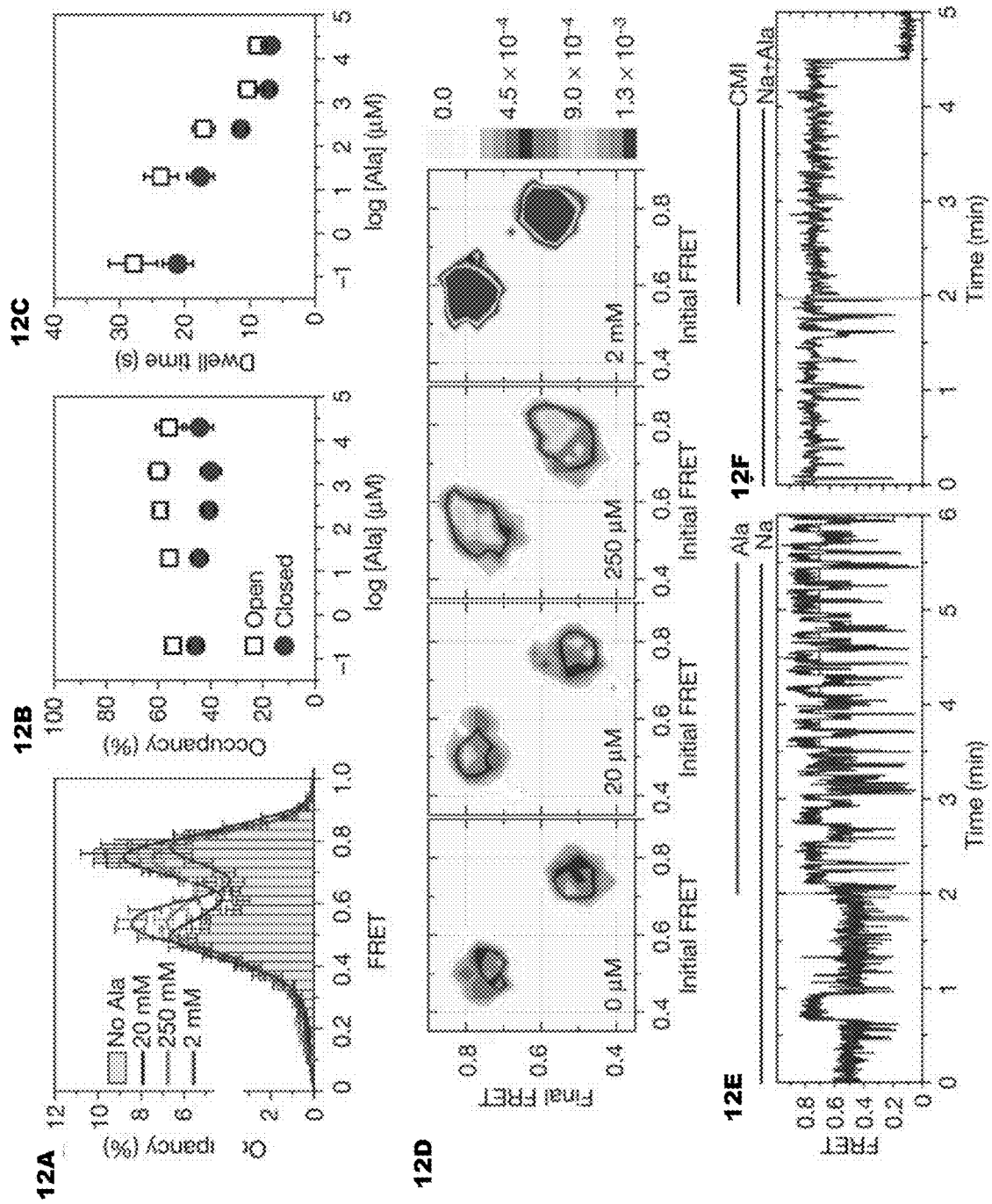

In stark contrast to Leu, under otherwise identical conditions, increasing Ala concentrations did not shift the FRET distribution toward the closed state (FIG. 12A-B), and a strong, Ala concentration-dependent enhancement of transition rates was observed. In 2 mM $Na^+$, Ala enhanced the transition rates between inward-open and inward-closed states by as much as ~4-fold (FIG. 12C-D). This result was directly confirmed at the scale of individual molecules upon exchange into Ala-containing buffer (FIG. 12E). In accordance with such effects requiring both $Na^+$ and Ala, the lifetimes of the inward-open or inward-closed states were not significantly affected by Ala alone (in the nominal absence of $Na^+$); at 250 µM Ala, the transition frequency increased in a $Na^+$ concentration-dependent fashion (FIG. 15). Collectively, these data are consistent with Ala lowering the activation barrier between the open and closed states ($\Delta\Delta G^{\ddagger}$) by as much as ~3 kJ/mol (the equivalent of 1-2 hydrogen bonds) under the conditions of the experiment. By contrast, the slowly transported substrate Leu raised the energy barrier to motion by as much as ~4 kJ/mol, similar to the effect of $Na^+$ (50 mM) alone.

Figures 13A, 13B, 13C, 13D:
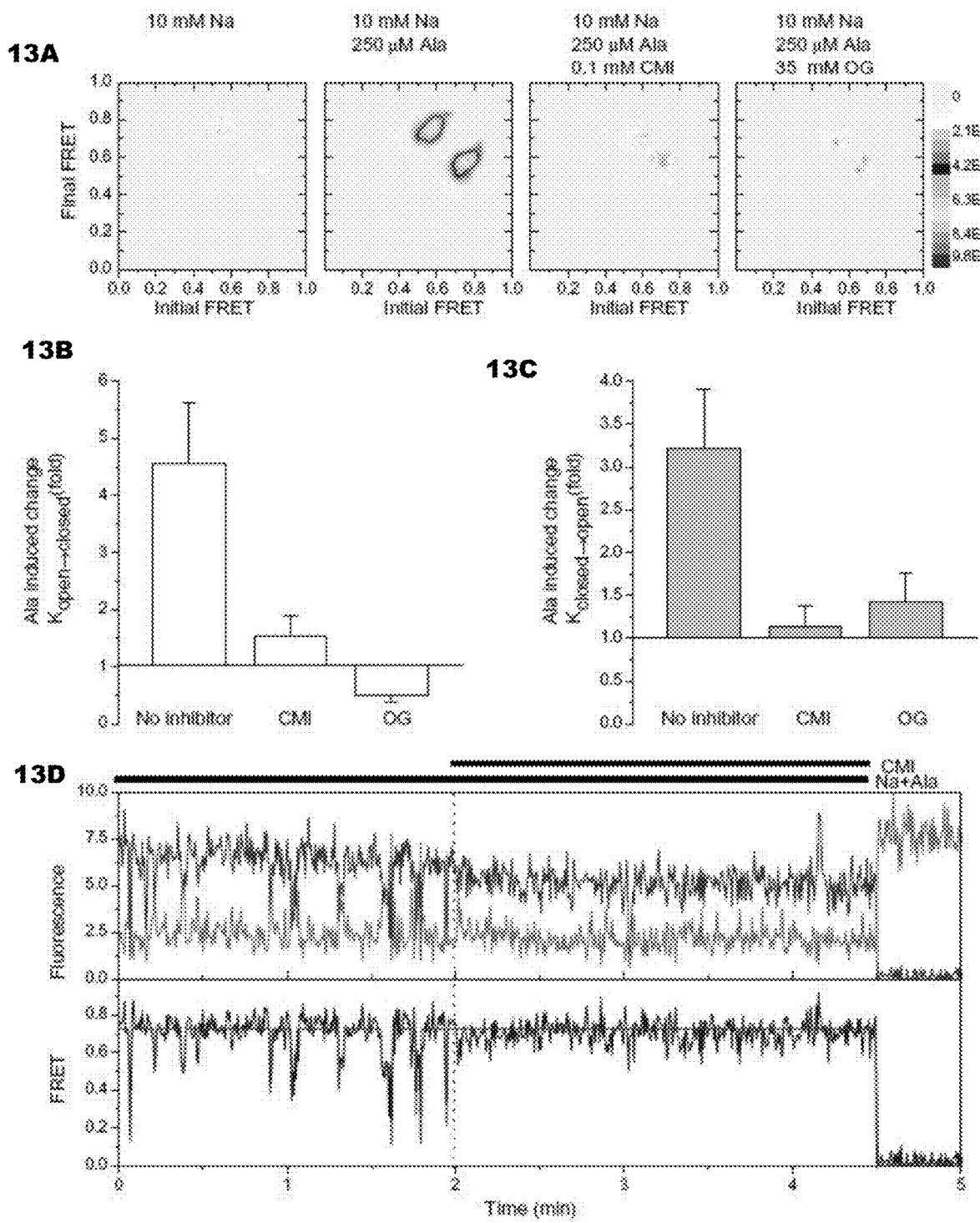

Hypothesizing that the dynamics observed reflect Ala's acceleration of opening-closing cycles of the intracellular gate as required for the transport mechanism, the inventors performed experiments in the presence of the transport inhibitor clomipramine (CMI). CMI, a tricyclic antidepressant, binds in an extracellular vestibule above the $Na^+$ and S1 binding sites. (Zhou, Z. et al., Science 317, 1390-1393 (2007); Zhou, Z. et al. Nature Struct. Mol. Biol. 16, 652-657 (2009); Singh, S. K. et al., Nature 448, 952-956 (2007)). Many of the residues shown to interact with antidepressants are also part of the S2 binding site (Zhou, Z. et al., Science 317, 1390-1393 (2007); Singh, S. K. et al., Nature 448, 952-956 (2007)). As substrate binding in the S2 site is thought to allosterically trigger intracellular release of $Na^+$ and substrate from the S1 site (Shi, L. et al., Mol. Cell 30, 667-677 (2008)), a strong prediction of this model is that CMI should block LeuT intracellular gating dynamics. Indeed, in the presence of both $Na^+$ (10 mM) and Ala (250 µM), where rapid intracellular gating dynamics are observed, CMI essentially eliminated the occurrence of intracellular gate opening, stabilizing LeuT in a high-FRET, inward-closed conformation (FIG. 13A-C). This observation is consistent with CMI competitively blocking substrate binding to the S2 site (Shi, L. et al., Mol. Cell 30, 667-677 (2008)), thereby preventing Ala-induced opening and closing of the intracellular gate and inhibiting transport. This result was again confirmed by direct imaging of individual LeuT molecules in $Na^+$ and Ala-containing buffer upon addition of CMI (FIG. 13D). Similarly, the detergent n-octyl-β-D-glucopyranoside (OG) also inhibited intracellular gating dynamics (FIG. 13A-C) consistent with its documented binding to the S2 site (Quick, M. et al., Proc. Natl Acad. Sci. USA 106, 5563-5568 (2009); Singh, S. et al., Channels (Austin) 2 (5) (2008)) where it also competes with substrate binding to disrupt the Na$^+$-coupled transport mechanism (Quick, M. et al., Proc. Natl Acad. Sci. USA 106, 5563-5568 (2009)).

Figure 14A:
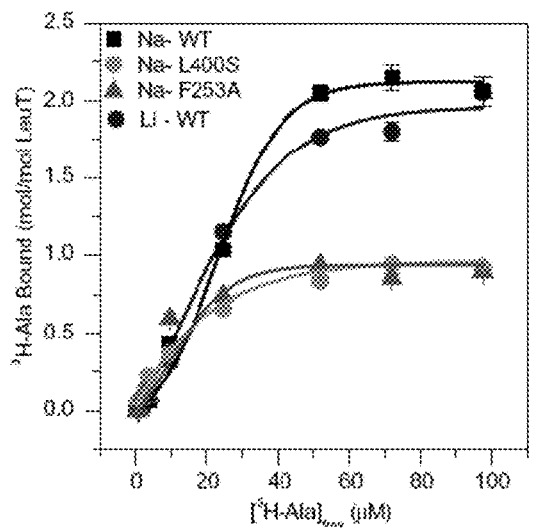
Figure 14B:
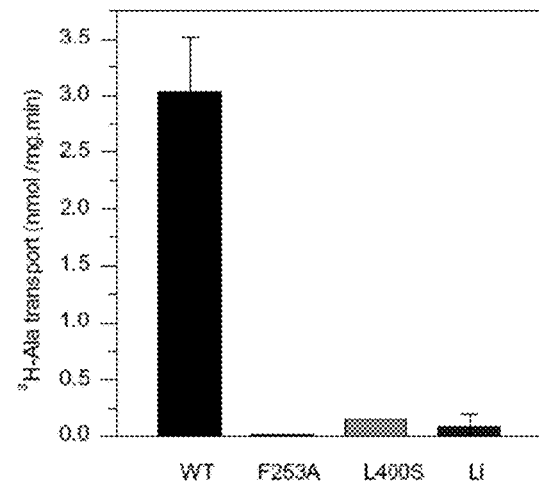
Figure 14C:
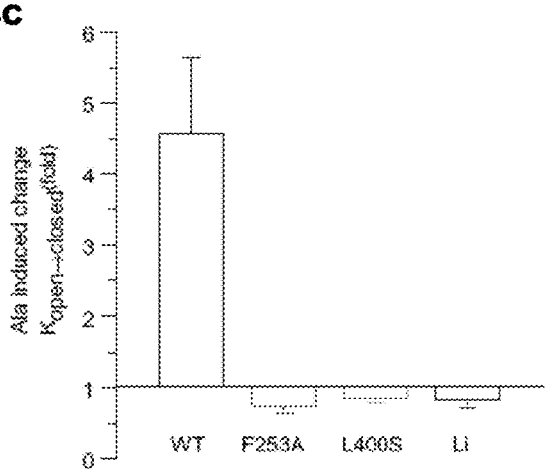
Figure 14D:
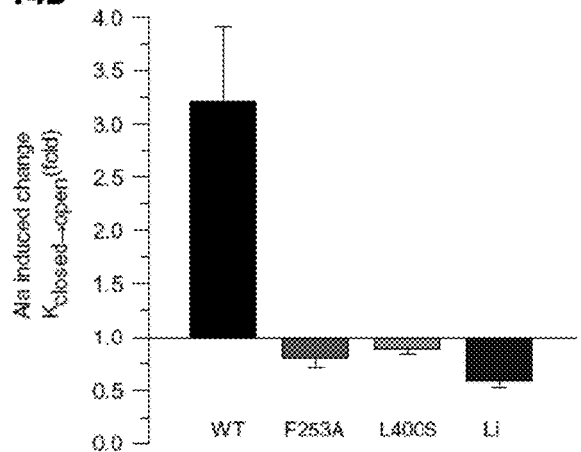
Figures 15A, 15B, 15C, 15D:
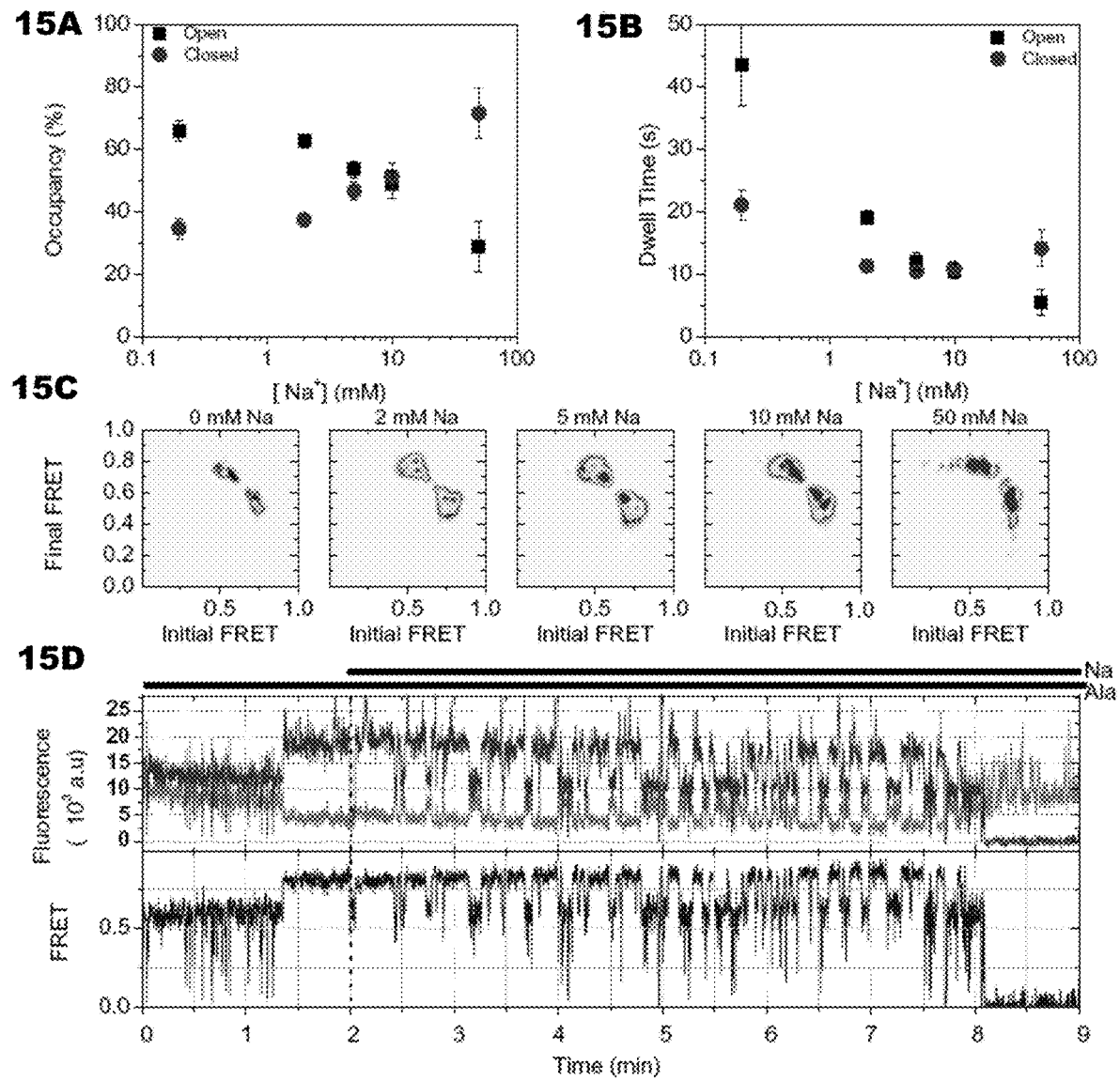

To probe whether Ala binding to the S1 and/or S2 site(s) was responsible for lowering the activation barrier for intracellular gating dynamics, smFRET experiments were repeated in the background of either an F253A or L400S mutation. These mutations within the S1 and S2 sites, respectively disrupt substrate binding to LeuT, decreasing the stoichiometry of substrate binding under saturating conditions from 2 to 1 (FIG. 14A). Mutation of F253 blocks substrate binding to the S1 site but not the S2 site and also abrogates transport (FIG. 14A-B), while having little or no effect on Na$^+$ binding. Despite evidence that Ala bound stoichiometrically to the S2 site in the context of the F253A mutation (FIG. 14A), Ala failed to increase intracellular gating dynamics of the mutant protein (FIG. 14C-D). These data indicate that occupancy of the S1 site is required for the propagation of the allosteric signal for the intracellular gating mechanism. Similarly, despite evidence of stoichiometric Ala binding to the S1 site (FIG. 14A), no increase in intracellular gating dynamics was observed when the S2 site was disrupted by the L400S mutation (FIG. 14C-D). Consistent with the notion that substrate occupancy in the S2 site is critical to the allosteric mechanism that controls intracellular gate opening and the transport mechanism (Shi, L. et al., Mol. Cell 30, 667-677 (2008)), these data demonstrate that substrate binding to the S1 site alone is insufficient to trigger intracellular gating dynamics. Thus, substrate binding at both S1 and S2 sites is necessary to trigger intracellular gating.

In order to probe whether Ala binding to the S1 and S2 sites is also sufficient to promote intracellular gating and transport, experiments were performed in the presence of Li$^+$ in place of Na$^+$. In the presence of saturating Li$^+$ concentrations (>150 mM) the inventors found that Ala binds LeuT at a 2:1 stoichiometry consistent with both S1 and S2 site occupancy (FIG. 14A). However, in the presence of Li$^+$, Ala failed to accelerate intracellular gating dynamics and substrate transport was not observed (FIG. 14B). Instead, the inward-closed conformation of LeuT was modestly stabilized (~2-fold reduction in the rate of gate opening, $k_{closed-open}$) (FIG. 14D). These data demonstrate that Ala binding to the S1 and S2 sites in the presence of Li$^+$ is insufficient to lower the activation barrier to intracellular gating.

Molecular Dynamics. The Li-only simulation was performed on a system prepared as described6. Briefly, the system consisting of over 77,000 atoms included the explicit membrane model, solvating water molecules, and the various ions and ligands. Here, all the Na$^+$ ions in the system were replaced with Li$^+$. The parameters for Li$^+$ were from Noskov, S. Y. et al., J. Mol. Biol. 377, 804-818 (2008), (Caplan, D. A., et al., Biophys. J. 95, 4613-4621 (2008)). All MD simulations were carried out with the NAMD program under constant temperature (310 K) and constant pressure (1 atm) (NPT) conditions. Long equilibration runs (720 ns) were performed to allow the system to transition to a new stable conformation. The inward-closed and inward-open conformations are based on the simulations described in Example 1.

Prompted by these experimental observations, computational studies were performed to investigate how both Na$^+$ and Li$^+$ can support substrate binding to LeuT, but only Na$^+$ leads to substrate-induced dynamics of the intracellular gate and to transport. These studies also served to identify local changes produced in the region of the ion binding sites and critical elements in the allosteric pathway linking the substrate binding sites and the intracellular gate region. Comparative analysis of two 720 ns molecular dynamics (MD) simulations of LeuT performed with either Na$^+$ or Li$^+$ occupying the established Na$^+$ binding sites in the absence of amino acid substrate (Na-only ((Claxton, D. P. et al., Nat Struct Mol Biol 17 (7), 822 (2010)) and Li-only, respectively) revealed significant differences in two important regions of LeuT. The first difference involves the extracellular segment of TM10 that contributes residues to the S2 site (e.g., L400). In the Li-only simulation, the backbone of residue G408 adopts a partially flipped configuration and the T409 side chain adopts an alternative rotamer state compared to the Na-only simulation, leading to a modestly distorted helical turn in TM10 in this key region of the extracellular vestibule. The second difference concerns conformational changes in the conserved aromatic cluster at the extracellular side of the S1 binding site (Claxton, D. P. et al., Nat Struct Mol Biol 17 (7), 822 (2010)), in particular the configurations of residues F252 and F253; in the presence of Li$^+$ these residues do not exhibit the same conformational changes as observed in the presence of Na$^+$ ((Claxton, D. P. et al., Nat Struct Mol Biol 17 (7), 822 (2010)). Thus, differences in the configuration of the G408-T409 pair observed in the Li$^+$-bound compared to Na$^+$-bound forms of the transporter appeared to propagate ion-specific effects through the cluster of aromatic residues linking TM6 and TM10 at the heart of the S1 binding site where they may directly affect the transport mechanism.

Although Li$^+$ in the Na1 site maintained interactions with T254 and E290 as seen for Na$^+$, Li$^+$ appeared less stably bound than Na$^+$. Consequently, the connections bridging E290, TM1 and TM6 were lost, affecting neighboring packing interactions between residues F252 and F253 within the F252-F253-F259 triad in TM6 and V412-V413 within TM10. The positions of these structural elements make them critical to the propagation of conformational changes deeper into the TM bundle towards the intracellular end of the transporter. Notably, this region includes residue E419, which was shown in the crystal structure of LeuT to participate in an interaction network with E62 in TM2, as well as the backbone of the unwound portion of TM6 (where F259 of the aromatic cluster is located), and two water molecules (Sen N, et al., Neuropharmacology 49 (6), 780 (2005)). Reconfigurations in this region of LeuT, including residue T418, upon simulated inward movement of the substrate (Shi, L. et al., Mol. Cell 30, 667-677 (2008)) were previously shown to enable the penetration of water from the intracellular side of LeuT as a result of an opening at IL1 (Shi, L. et al., Mol. Cell 30, 667-677 (2008)).

Dissociation of IL1 from interactions with R5 and D369 and destabilization of this network of intracellular interactions is associated with the outward movement of TM1a, which is essential for release of substrate to the inside. Due to the differential effects of Li$^+$ and Na$^+$, Ala binding in both the S1 and S2 sites in the presence of Li$^+$ would not engender the ordered series of local conformational rearrangements (expected in the presence of Na$^+$) that originate in the S2 site. These rearrangements are propagated through the Na1 binding site and enable water penetration from the cytoplasmic side of LeuT, and the movement of TM1a. As a result of this difference between the effects of Na$^+$ and Li$^+$, substrate-induced acceleration of gating dynamics was not observed in the presence of Li$^+$. The inventors note that the residues found to participate in this signal propagation pathway correspond to residues that were shown in mutational studies of the cognate serotonin transporter (SERT) to affect functional and allosteric properties in a manner consistent with the present findings (e.g., cysteine substitutions of T503 or E508, which correspond to F414 and E419 in LeuT (Keller, P. C. et al., Biochemistry 43 (26), 8510 (2004)), and the mutation of the SERT TM10 sequence A505 to I507 (corresponding in LeuT to G416 to T418), which disrupted the effects of allosteric modulators in SERT (Zhong et al 2009; Neubauer, H. A. et al., Mol Pharmacol 69 (4), 1242 (2006)).

$Na^+$ binding, which stabilizes the inward-closed state, does not hasten gate closure but, instead, slightly stabilizes the inward-open state as well, by raising the energy barrier to the conformational transition. In contrast, Ala binding to LeuT shortens not only the inward-closed but also the inward-open lifetime (FIG. 12). Thus, bound Ala facilitates intracellular gate closure and its opening by reducing the activation barrier for this conformational transition through the type of propagation mechanism revealed by the simulations. The most succinct description of such a molecular mechanism is that binding of S2 triggers opening of the intracellular gate and release of S1 to the cytoplasm but then, in the absence of S1 and bound $Na^+$, S2 facilitates intracellular gate closure. It is possible that in the presence of extracellular $Na^+$, S2 would move to the S1 site with high efficiency due to the very high local concentration, facilitating a subsequent transport cycle.

Collectively, the observations made here support the notion that the observed movements of TM1a and its environment are associated with LeuT intracellular gating (Zhao, Y. et al., Nature 465 (7295), 188 (2010)) in a manner that is directly linked to the $Na^+$-driven transport mechanism. Thus, results obtained with the slowly transported substrate, Leu, and the relatively fast substrate, Ala, in the absence and presence of the transport inhibitor CMI, directly correlate rates of intracellular gating with substrate transport. The role of substrate binding at the S2 site in the process of allostery and molecular recognition is further highlighted by the comparative effects of CMI and Ala binding to this site in the presence of $Na^+$. The former stabilizes a closed intracellular gate conformation while the later substantially lowers the activation barrier to gate opening, thereby allowing the energy of the $Na^+$ gradient to drive the transport mechanism.

Example 3

Tyt1 and $Glt_{Ph}$

Protein expression and purification. $Glt_{Ph}$ and single cysteine mutants of the gene ($Glt_{Ph}$-V355C and $Glt_{Ph}$-G357C) was cloned into pBAD24 and over-expressed in *E. coli* Top10® cells. Proteins were purified by metal chelating chromatography on Ni-NTA resin. Protein purity and structural integrity were assessed by SDS PAGE analysis and by size exclusion chromatography (SEC), respectively. Purification and analysis of *L. lactis*-expressed Tyt1 (Quick, M., et al., J. Biol. Chem. 281, 26444 (2006)) was performed by similar strategies.

Fluorescent labeling of the transporters. Mutant proteins containing one or more cysteine residues were derivatized using maleimide-coupled Cy3 and Cy5 fluorophores (GE Healthcare). The single native cysteine in $Glt_{Ph}$, and the two native cysteines in Tyt1, were removed by mutation to create cysteine-less transporters with normal expression and function (Quick, M., et al., J. Biol. Chem. 281, 26444 (2006); Quick, M. et al., Proc. Natl Acad. Sci. USA 106, 5563-5568 (2009)). For the preparation of donor and acceptor-labeled transporters, proteins were labeled with a 1:1 mixture of Cy3 (GE) and Cy5 (GE) dyes. Proteins were purified away from unreacted dye by Ni-NTA chromatography and analyzed by SDS PAGE. Prior to smFRET experiments, Cy3/C5 labeled proteins were also generally purified by size exclusion chromatography.

Figure 16E:
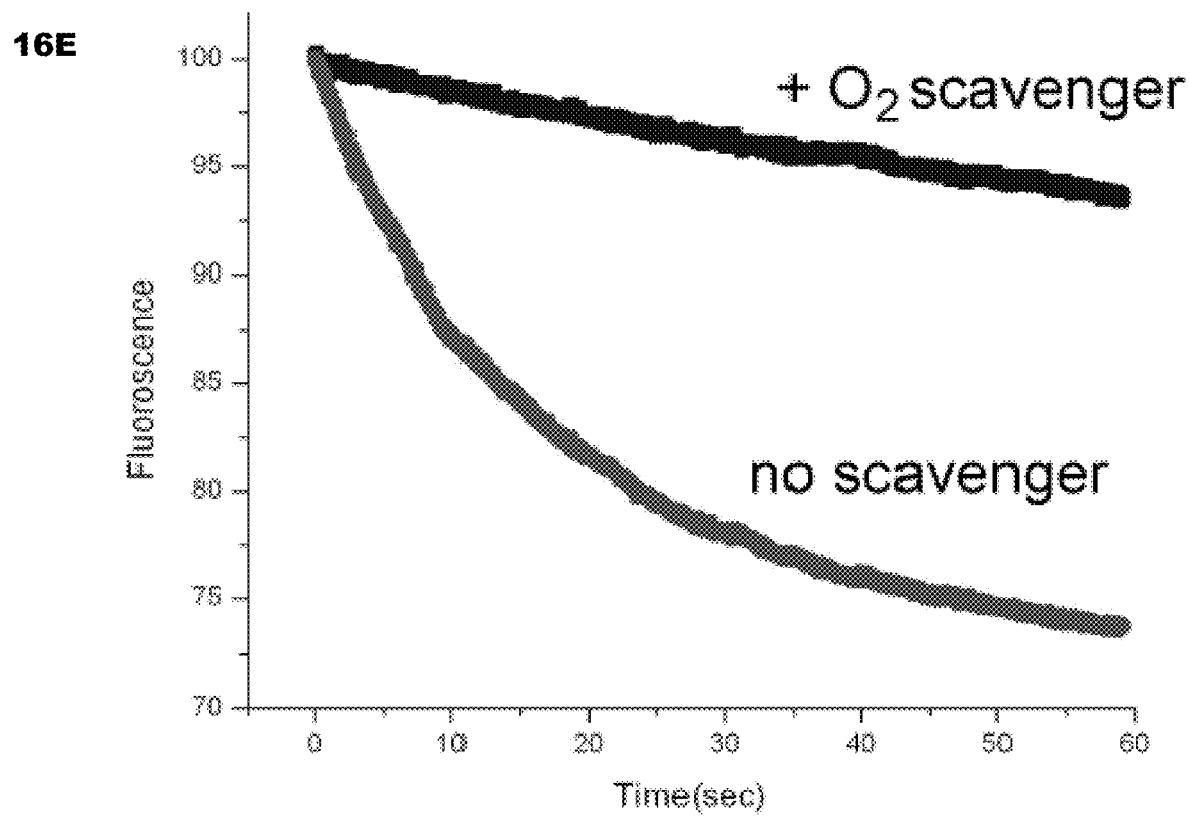

Surface attachment of liposomes for single-molecule fluorophore detection. Liposomes, ~100-400 nm in diameter, were prepared using a mixture of *E. coli* polar lipids and egg lecithin, with or without the addition of Biotinyl-PE (Avanti Polar Lipids). Proteoliposomes were loaded with dye-labeled material and/or the enzyme coupled reaction components via freeze-thaw cycles, or other strategies, followed by extrusion through the appropriately sized filters. Liposomes were attached to the microscope slide via a biotin/streptavidin bridge (FIG. 16C). Importantly, liposomes alone do not have significant background fluorescence. Discrete photobleaching steps, a signature of single fluorophores, provided an accounting tool for determining how many dye molecules were trapped within each surface-attached liposome (FIG. 16D). Through such experiments the inventors observed that liposome-embedded Tyt1 is a monomer. Surface-attached liposomes were stable over several minutes and oxygen scavenging methods and other specific protocols were used to significantly extend the lifetime of dye molecules (FIG. 16E).

Observations of FRET in Cy3/Cy5-labeled transporters. Labeled proteins, reconstituted into 100 nm biotinylated lipid vesicles at a ratio of approximately 1 protein per vesicle, showed clear indications of dynamic FRET. For $Glt_{Ph}$ and Tyt1, at least three distinct FRET levels were clearly identified in the ensemble of imaged molecules (FIG. 17).

---

What is claimed is:

1. A method of conducting dynamic single-molecule fluorescence studies on a transmembrane protein comprising:
   a) obtaining a transmembrane protein which is labeled with fluorophore at one or more sites and is placed in a membrane protein carrier, wherein the one or more sites have solvent accessibility and none of the labeling sites faces the bilayer of the membrane protein carrier;
   b) immobilizing said transmembrane protein onto a solid surface;
   c) imaging the immobilized transmembrane protein to acquire fluorescence data over a period of time; and
   d) correlating the fluorescence data with conformational changes in said transmembrane protein.

2. The method of claim 1, wherein the dynamic single-molecule fluorescence studies are dynamic single-molecule fluorescence resonance energy transfer (smFRET) studies.

3. The method of claim 2, wherein at least two mutations have been introduced into said transmembrane protein to permit affixation of a donor fluorophore and an acceptor fluorophore.

4. The method of claim 3, wherein the two mutations are introduced into sites that increase or decrease in distance from each other depending on the conformation of said transmembrane protein.

5. The method of claim 4, wherein the two mutations are introduced into amino acid positions that are separated from one another in the protein tertiary structure by a distance approximating the $R_0$ for the donor fluorophore and acceptor fluorophore.

6. The method of claim 3, wherein the two mutations are introduced into sites that show low conservation between members of the family of proteins of which said transmembrane protein is a member.

7. The method of claim 3, wherein the mutations are introduced into sites that are outside of the activity domains of said transmembrane protein and do not affect ligand binding or transport activity of said membrane protein.

8. The method of claim 3, wherein at least one additional mutation is introduced to a site within an activity domain of said membrane protein to generate a gain-of-function or loss-of-function mutant protein.

9. The method of claim 3, wherein the mutations are cysteine substitutions.

10. The method of claim 9, wherein the fluorophores are maleimide dyes.

11. The method of claim 1, wherein said carrier is selected from the group consisting of: detergents, lipids, nanoparticles, micelles, liposomes, and cells.

12. The method of claim 1, wherein said transmembrane protein is biotinylated and immobilized by the biotin-streptavidin interaction to said solid surface.

13. The method of claim 2, wherein fluorescence data is acquired for an extended imaging time period sufficient to observe multiple conformations of said membrane proteins and transitions therebetween.

14. The method of claim 13, wherein the acquired data permits the identification of distinct conformations.

15. The method of claim 14, wherein the acquired data permits determination of the FRET value for each conformation, the dwell time for each conformation, the transition time from one conformation to another, and the distribution among different conformations.

16. The method of claim 1, wherein the membrane protein carrier is n-dodecyl-β-d-maltopyranoside (DDM).

17. The method of claim 1, wherein the membrane protein carrier is biotinylated and immobilized by the biotin-streptavidin interaction to said solid surface.

18. The method of claim 17, wherein the membrane protein carrier is n-dodecyl-β-d-maltopyranoside (DDM).

19. The method of claim 12, wherein the membrane protein carrier is n-dodecyl-β-d-maltopyranoside (DDM).

20. The method of claim 1, wherein the imaging is performed in the presence of an oxygen scavenger.

21. The method of claim 1, wherein the imaging is performed in the presence of a triple state quencher (TSQ) selected from the group consisting of Cyclooctatetraene, Trolox and nitro benzyl alcohol (NBA).

22. The method of claim 21, wherein the TSQ is attached adjacent to or directly to the fluorophore.

* * * * *